(12) United States Patent
Lehrer et al.

(10) Patent No.: US 10,262,103 B2
(45) Date of Patent: Apr. 16, 2019

(54) INDIVIDUALIZED CANCER TREATMENT

(76) Inventors: Raphael Lehrer, Rockville, MD (US); Robert Coopersmith, Chestnut Hill, MA (US)

( * ) Notice: Subject to any disclaimer, the term of this patent is extended or adjusted under 35 U.S.C. 154(b) by 1529 days.

(21) Appl. No.: 12/621,408

(22) Filed: Nov. 18, 2009

(65) Prior Publication Data

US 2010/0130527 A1 May 27, 2010

Related U.S. Application Data

(60) Provisional application No. 61/115,898, filed on Nov. 18, 2008.

(51) Int. Cl.
*A61K 31/436* (2006.01)
*G06F 19/20* (2011.01)
*G06F 19/18* (2011.01)

(52) U.S. Cl.
CPC .............. *G06F 19/20* (2013.01); *G06F 19/18* (2013.01)

(58) Field of Classification Search
None
See application file for complete search history.

(56) References Cited

U.S. PATENT DOCUMENTS

| 5,436,142 | A  | * | 7/1995  | Wigler et al. | 435/91.2 |
| 2003/0224464 | A1 | * | 12/2003 | Thompson | 435/7.23 |
| 2004/0197774 | A1 | * | 10/2004 | Wigler et al. | 435/6 |
| 2007/0172844 | A1 | * | 7/2007 | Lancaster et al. | 435/6 |

OTHER PUBLICATIONS

Krauthammer et al. Molecular triangulation: Bridging linkage and molecular-network information for identifying candidate genes in Alzheimer's disease. PNAS, 2004 vol. 101 No. 42, p. 15148-15153.*
Draghici et al. Genome Res. 2007 17: 1537-1545, Sep. 4, 2007.*
Dressman et al. J Clin Oncol 25:517-525, 2007.*
Sparks et al. Cancer Research, 58,1130-1134, 1998.*
Barra, Computer Methods and Programs in Biomedicine (2006) 81:174-180.
International Search Report and Written Opinion for PCT/US2009/065011, dated Mar. 5, 2010, 7 pages.
Wulfkuhle et al., European Journal of Cancer (2004) 40:2623-2632.
Dahiya et al., PLoS ONE (2008) 3(6):e2436.

* cited by examiner

*Primary Examiner* — Michael L Borin

(57) ABSTRACT

Methods to formulate treatments for individual cancer patients by assessing genomic and/or phenotypic differences between cancer and normal tissues and integrating the results to identify dysfunctional pathways are described.

13 Claims, 25 Drawing Sheets

B-Raf Signaling

*Melanoma Mechanisms Pathway Including PTEN Down-Regulation*

INDIVIDUALIZED CANCER TREATMENT

CROSS-REFERENCE TO RELATED APPLICATION

This application claims benefit of U.S. Ser. No. 61/115,898 filed 18 Nov. 2008, the contents of which are incorporated herein by reference.

TECHNICAL FIELD

The invention relates to analysis of tumor tissue of individual patients to determine irregularities in gene expression that leads to identifying suitable treatments. Because each patient is individually analyzed for expression abnormalities, tailoring treatment protocols to the particular malignant tissue present in the patient is possible.

BACKGROUND ART

There is a plethora of known drugs sometimes used singly, but mostly in combination, for treating solid and blood tumors in humans. Chemotherapeutic approaches using small molecules such a vincristine, gemcitabine, 5-fluorouracil, and a litany of others (such as Gleevec®) which are used mostly in combination therapies, is widespread. In addition, biologicals such as Rituxan®, Erbitux™, and Herceptin® have also been used. With the exception of Herceptin®, and Gleevec® which targets an abnormal BCR-ABL protein found in patients with chronic myelogenous leukemia and a few others, these treatments are generally applied to individual patients based on guesswork rather than analysis. The heterogeneity of tumor types, even within a given organ such as breast or prostate, makes it difficult to ascertain in advance whether an individual patient's malignancy will, or will not, be responsive to any particular protocol. To applicants' knowledge, at least until recently, only the administration of Herceptin® was systematically based on the results of a companion diagnostic on an individual patient for an indication of whether (or not) the tumor will respond. More recently, other attempts to individualize treatment have been implemented, including chemosensitivity screening and tests for an individual target (e.g., KRAS mutations) which are used by some doctors. Estrogen receptor screening is often done routinely before administration of tamoxifen.

Studies have been done, however, with respect to tumor types in pools of many patient samples derived from a given organ or of cancers of a particular type to identify, in general, which metabolic or signal transduction/biological pathways are dysregulated in tumors of various types and which genes are over-expressed- or under-expressed. For example, studies of micro-RNA production patterns in ovarian cancer have been conducted by Dahiya, N., et al., *PLoS ONE* (2008) 18:e2436. Attempting to find such patterns on an individual basis has been limited to the recently reported sequencing of the entire genome of tumor cells from an individual patient at the cost of over $1 million, and as the patient had died before the project began, it too was not aimed at treatment of the patient herself. As the costs of sequencing have come down dramatically, a number of groups are conducting studies which attempt to sequence at least all of the open reading frames of genomes in cancer patients, comparing the sequences derived from tumor to those from normal tissue. The results of these studies are, at this point, unclear.

It would be extremely helpful to be able to formulate a treatment protocol for an individual patient based on the vulnerability of tumor cells in this patient to such a protocol as determined by the pathway-based irregularities which appear to be associated with the tumor. The present invention offers just such an opportunity.

DISCLOSURE OF THE INVENTION

The invention solves the problem of tailoring treatment protocols to individual cancer patients in a rational way by assessing the abnormalities effecting malignant growth in the tumor cells of the individual. By ascertaining the abnormalities in tumor cells as opposed to normal cells in the same individual, these abnormalities can be targeted in view of the availability of the many drugs whose target sites are already known.

Thus, in one aspect, the invention is directed to a method to identify a treatment target protocol in an individual cancer patient, which method comprises:

(a) ascertaining characteristics of the genome and/or characteristics of the molecular phenotype in a biopsy of the cancer afflicting said patient to obtain one or more first data sets and in normal tissue of said patient to obtain one or more second data sets;

(b) identifying differentiated characteristics in said one or more first data sets which differ from those in said one or more second data sets;

(c) ascertaining one or more pathways associated with said identified differentiated characteristics; and (d) identifying at least one therapeutic target associated with said one or more pathways.

The method may further include designing a treatment protocol using drugs and/or biologics that interact with said at least one target.

The invention may further include administering the formulated treatment protocol to the patient and repeating the process after administration to determine whether the treatment had an impact and/or caused redundant pathways to operate. In addition, the treatment protocol formulated according to the method of the invention, may, in cooperation with the identified differentiated characteristics, be applied to discover further therapeutic and diagnostic methods appropriate for additional subjects.

In determining data sets related to the genome, among those characteristics that will be assessed are: presence of single nucleotide polymorphisms (SNPs), loss of heterozygosity (LOH), copy number variants (CNVs) and gene methylation, and sequence (full genome, full exome, or targeted). Multiple polymorphisms would, of course, also be included.

Characteristics which provide datasets for molecular phenotypes include overexpression or underexpression of open reading frames assessed either by RNA level or protein levels, and proteomic and activity analyses.

It is advantageous to diminish the misleading effects of noise in a single type of dataset by triangulating multiple data points to identify a biologically significant pattern (e.g., a pattern of over- and under-expressed genes consistent with the dysregulation of a specific pathway). It is often possible, as well, to extrapolate the results to characteristics that are not themselves measured, as illustrated below.

While it is possible to perform the method of the invention using only one type of characteristic or data set, such as over/underexpression of open reading frames, it is highly advantageous to use multiple types of data sets so that integration analyses can be performed taking advantage of redundancy of indications. Thus, using combinations of, for example, overexpression/underexpression with CNV/LOH databases not only provides an increased level of confidence in the results, but also allows correlations to come to light leading to hypothesize pathways that might not otherwise be seen.

MODES OF CARRYING OUT THE INVENTION

Figure 1:
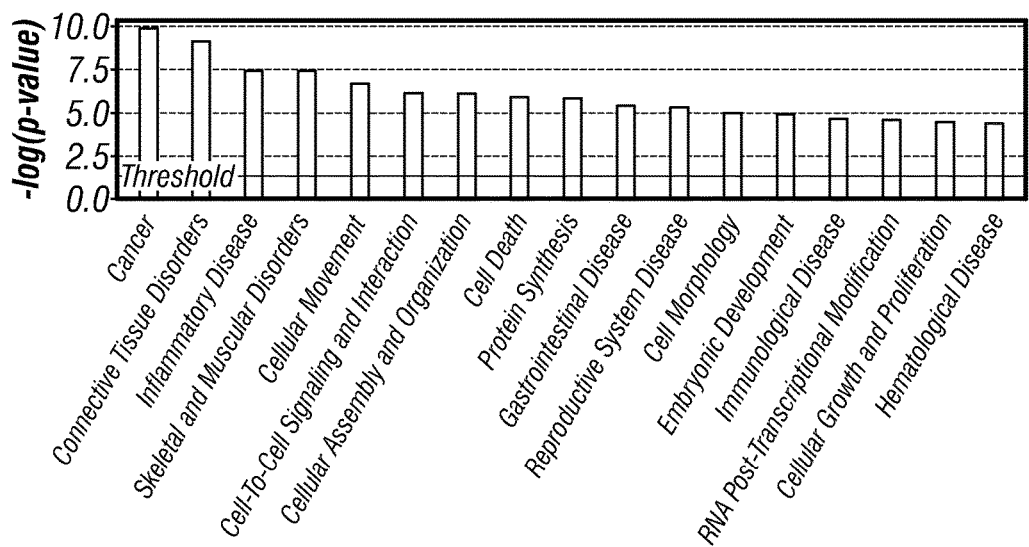
FIG. 1 is a graph showing cellular functions enriched in regulated genes from primary colon tumor sample.
Figure 1:
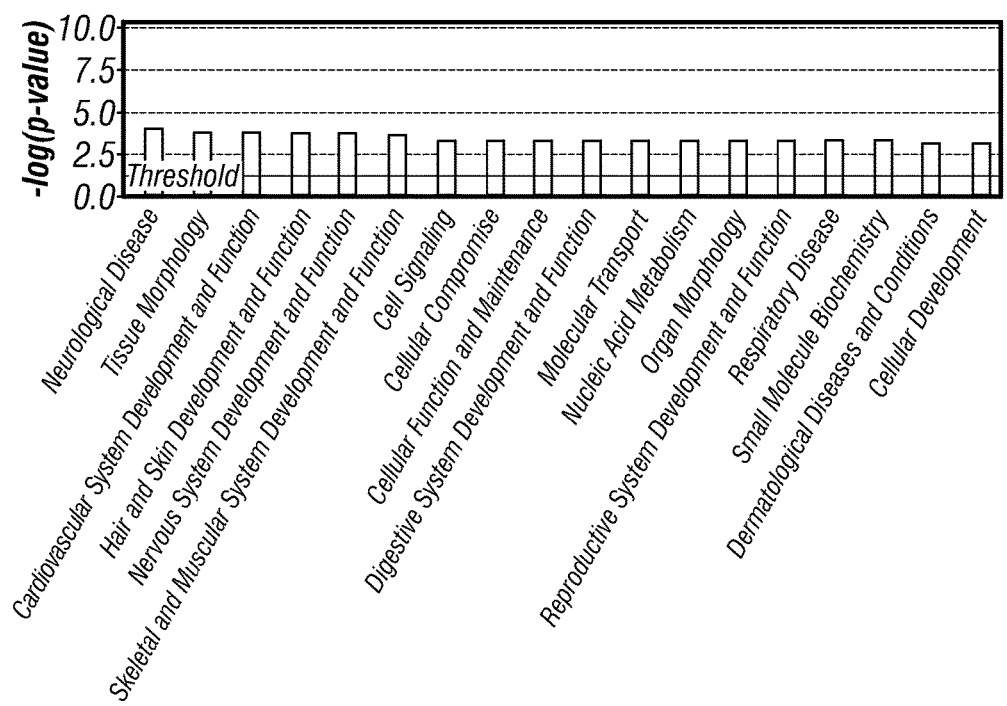

The method of the invention takes advantage of the exponential growth of knowledge related to gene expression, metabolic pathways, signal transduction pathways, the nature of drug targets, and cell regulation systems that has accumulated over the past half century, as well as techniques for organizing this information, and accessing multiplicities of data points in a relatively economic fashion. A number of canonical pathways are already postulated and understood in the art based on isolated findings reported in the literature, but many more pathways remain to be elucidated by assembling and evaluating these data. By virtue of obtaining and triangulating large numbers of data points for an individual patient within and across datasets, applicants are able to overcome the inherent noise from a measurement of few samples and provide a road map of the abnormalities associated with tumor cells as opposed to normal cells in the patient and thus formulate treatment regimens targeting the components of these irregularities.

The method of the invention begins by obtaining suitable biopsy samples from the patient. The biopsy is obtained using standard methodology; at least one sample, but preferably three (which allows calculation of a p-value), is obtained from tumor tissue and another sample but preferably three, is obtained from normal tissue in the same individual. The individual may have a primary solid tumor of an organ such as liver, kidney, stomach, bone, lung, pancreas, prostate, breast, ovary, bladder, eye, skin, or other specific location whereby an intact sample of small dimension can be obtained readily. Alternatively, the tumor cell may be distributed throughout the bloodstream as is the case for leukemias or lymphomas and the tumor cells are then recovered from and separated from normal cells in the blood. Tumor markers have also been found in bodily fluids in general such as saliva and serum. The primary solid tumor may also have metastasized and samples of metastatic tissue should also be obtained and assayed according to the method of the invention. In one embodiment, normal cells are obtained from similar tissues in which the primary tumor is found in the same individual who provides the tumor sample. Alternatively, normal tissue from the organ to which it has metastasized could be used as the comparative standard. If normal tissue from the same patient is not available, expression levels of various genes in normal tissues are available from databases such as GEO, maintained by the NCBI, as well as several maintained by companies (e.g., Gene Logic). One advantage of using the patient's own normal tissue is that the standard permits taking account of any drugs that may be in the system of this patient, such as chemotherapeutic drugs that have already been administered, as well as individual biological variability.

In some cases, the normal tissue may contain substantial numbers of stromal cells which are cells that support the tumor itself and which may distort the comparison. These stromal cells are connective tissue cells and are associated with a number of organs to support the functional cells in bodily organs. Stromal cells include fibroblasts, immune cells and endothelial cells, among others. In particular, if the normal tissue contains stromal cells, the methods described below to further validate the results of the method are particularly important.

The biopsy samples are preserved by methods standard in the art, such as flash-freezing or by embedding them in paraffin and fixing them with formalin.

Next, the relevant cellular components are extracted. For analysis of a molecular phenotype, expression levels may be measured using, for example, level of mRNA. The mRNA is extracted and isolated using standard techniques. The extracted mRNA is then assessed using whole genome microarrays, many of which are commercially available from Affymetrix, Illumina, or Agilent, for example, or is obtained through whole exome sequencing. The results from the microarray analysis provide data which show expression levels of a multiplicity of genes in tumor derived tissue and normal tissue.

Comparison for each gene of its level of expression in tumor and normal tissue permits an assessment of overexpression or underexpression of each gene in the tumor tissue as compared to normal. Any useable level of differentiation can be employed, for example, only genes that are expressed at a level of 10-fold, 5-fold, 3-fold or 2-fold differences may be considered. Within the same comparison, if desired, different differential standards may be employed for different groups of genes. It is not necessary to use hard cutoffs, and fadeout techniques can also be employed. Differing levels of p-values may also be employed to filter the gene list, depending on the context.

For metastasized tissue, the normal control may include either the primary organ or the organ which is the location of the metastasis; both can be employed if desired. Further, if there are multiple metastases, each one may have a different pattern.

In addition to assessing expression levels using mRNA as an index, the levels of protein present may be assessed using, for example, standard proteomic techniques or immunoassays. The activity of various proteins may also be assessed using standard techniques. The nature of the analysis of molecular phenotype is not critical—any method to obtain information about aspects of the phenotypic characteristics that may be relevant to the cancer could be used.

For determination of genomic characteristics, chromosomal tissue is extracted from the biopsy samples and analyzed, for example, for the presence of SNPs that are characteristic of the tumor tissue as compared to normal. The analysis also involves microarrays, and microarrays for SNP analysis are also available commercially. There may also be multiple copies of the certain genes and the commercially available SNP arrays are able to provide information concerning copy number (CNV), as well as the presence of the SNP itself. This information can also be obtained through full-genome sequencing, or other designed sequencing approaches.

The identification of one or more SNPs in the tumor tissue as compared to normal tissue, and the copy number thereof, as well as loss of heterozygosity (LOH) or methylation patterns also provide information as to the pathway irregularities that might be found in the tumor tissue. Multiplicities of SNPs provide further information along these lines. In one embodiment, information regarding copy number of genes in tumor tissue may be combined with the data on overexpressed and underexpressed genes to result in additional data points that add to the accuracy of the analysis. Thus, since a single patient is being evaluated, the availability of more data points provides an opportunity to distinguish signal from noise, by noting convergent results. Using, for example, the combination just of SNP data and expression data, there may be 20-50 or more data points supporting a given therapeutic hypothesis (pathway members×SNP/CNV).

As illustrated below, the data obtained are used as a basis for determining which pathways in the tumor cell are abnormal. The pathways may be metabolic pathways or signal transduction pathways or any other group of interacting proteins which may affect cellular functioning. The pathways may either be those already known and described in textbooks, or may be assembled from curating the primary literature. This curatorial activity and assembly into putative pathways has already been accomplished in many instances and algorithms for fitting aberrant genes, such as overexpressed and underexpressed genes, into such pathways are available from, for example, Ingenuity, GeneGo, and Pathway Assist. These algorithms are only available for expression data, so other types of data (copy number, mutation, etc.) are inserted into Ingenuity with a specific fold change—e.g., 1,000—used as a "flag" to identify them. The resultant data are then used for visualization purposes to identify pathway hypotheses, and are later removed and adjusted to be denoted by other means for the purpose of elucidating the pathways/discussing them. These tools may be supplemented by curatorial activities practiced by the diagnostician and assembled in the diagnostician's own database. This latter possibility is particularly important since SNPs occurring in tumors may not necessarily be represented in commercially available microarrays.

Clearly, the complexity of the correlations and algorithms required for determining relevant pathways requires the use of software and computer manipulations.

The dysregulated pathways identified using these techniques are assessed by several criteria, including
1. whether the pathway contains a sufficient number of independent data points to overcome the statistical limitations of having few samples;
2. whether the pathway exhibits a coherent pattern, for example, if gene products involved are consistently upregulated or downregulated in accordance with the performance of the pathway itself;
3. whether the pathway is plausibly disease-relevant—e.g., whether there are reports in the literature that the pathway may be somehow linked to malignancy;
4. whether the pathway contains targets that correspond to approved or investigational drugs or biologics that can be used to mitigate the irregularity in the pathway; and
5. whether the pathway is validated by confirmatory evidence from data obtained from several types of characteristics.

Of course, not every one of the above five criteria need be met. However, if a protocol is to be formulated, there must be known or investigational drugs or biologics that can target the components of the pathways identified.

A single type of data, such as overexpression/underexpression may be employed when necessary, but it is beneficial when possible to combine information concerning differential characteristics obtained according to these criteria with differentiated characteristics obtained using genomic information such as SNPs or CNV or both, or with other types of data sets, to that integration techniques can be employed.

The integration of more than one type of data is illustrated below in Examples 4 and 5. By integrating data from more than one type of determination (e.g., expression levels and genomic data) targets and treatments are suggested that would not have been evident by the use of one data set alone.

This latter confirmatory data employs analysis of either the function of the individual genes identified in the pathway or the genes that are simply on the list. If these genes are known to provide functions that are reasonably related to cell proliferation of abnormal growth, this further confirms the validity of the list and the projected pathway. If the pathway contains genes that exhibit SNPs in the tumor tissue and altered copy number, this further validates the relevance of the pathway.

Triangulation and Integration

As noted above, because multiple observations are obtained, their collective implications will permit deduction of the existence of characteristics that have not been directly measured. This can be considered as one manifestation of "triangulation" and/or "integration" which permits such inferences to be drawn.

For instance, where copy number and expression data indicate possible enhanced EGFR activity and thus hyper-phosphorylation, this is inferred by data showing that the AT1R pathway was dysregulated. It is known that AT1R transactivates EGFR. It is inferred from an indication that EGFR is being degraded at a slower rate than normal, and the receptor not being desensitized as much as it would ordinarily be because p38 is downregulated, and one of its functions is to desensitize and degrade EGFR.

Thus, by correlating the results of multiple data points and multiple types of analysis, greater assurance is provided that the measured parameters are significant (as discussed further below) and further leads to additional conclusions that could not be drawn simply from the actual measured data points.

In addition, the noise level is managed by triangulation methods (as discussed in further detail below).

The term "triangulation" as used in the present application refers to assembling multiple individual items of data into meaningful compilations based on the known interrelationships of the components for which each data point is obtained. Thus, data with respect to individual members of a known pathway, for example, are assembled so that mutually supportive inferences enhance the probability that the pathway itself is aberrant or not aberrant in a tumor sample. By virtue of assembling these data in an orderly fashion, the significance level of the conclusion suggested by the data is enhanced. This is essentially a way to obtain meaningful results against a noisy background, as discussed further in the following paragraph and in the algorithms described below.

Management of the noise problem has traditionally been done by using a large cohort of patients/data/samples, and averaging them. While one may not trust every gene of every sample, the average is much more trustworthy. For example, when using microarrays, a significance value of $p<0.05$ for an individual gene is not particularly valuable. The reason is that there are 40,000 genes on the chip, so one would expect that $40,000 \times 0.05 = 2,000$ genes that would show as $p<0.05$ purely on a random basis. Typically a correction factor is used, multiplying the p value by the number of genes ("false discovery" or Bonferroni correction), so that one would need a $p<0.00001$ on a specific gene to have a 5% overall chance that the data are correct. Current technology does not provide such sensitivity for a specific sample, so the usual approach is to average over numerous data sets, to lower the p value to this threshold, as well as often to predefine a limited set of genes (e.g., a few hundred) that one is interested in to reduce the magnitude of the correction and lower the p-value. Even then it is hard to achieve significance, which means that further validation studies that focus on the single gene of interest are necessary to establish significance for it.

In another example, for microarray data with 20,000 known genes, to be certain that a given gene is statistically significant to the $p=0.05$ level requires a p-value on the individual genes of $p=2 \times 10^{-6}$. Obtaining $p=0.05$ on the single gene would require $1 \times 10^{13}$ samples. One approach is to restrict the sample to a set of candidate genes, for example, to only 100 out of the 20,000. This would mean a p-value of only $p=0.0005$ for each gene corresponding to 10,000 samples. These calculations use the Bonferroni correction of $p\_adj=Np$, where N is the number of genes being examined, and the standard error of the mean formula, $p\_mean=p/\sqrt{n}$ where n is the number of samples.

The approach in the prior art is to use a set of samples for discovery of the gene, and then a set of samples used for validation, focused only on the gene of interest. As many genes will "appear" attractive on the training set, the odds of them validating in the validation set are low. Thus, these approaches work with larger databases, but not with only a few samples.

When working with a single patient, however, this cannot be done—the data are limited to a very small number of samples (e.g., 3 replicates), much too small to use this approach. Previous attempts to overcome this required a great deal of experimental/wetlab work to validate results for every gene of interest, and require use of a single platform. Changing arrays, or using FFPE samples instead of flash frozen, would require repeating all of these experiments.

The present invention achieves these goals by examining dysregulation at the functional/pathway level. If only the gene level is examined, it is important to know whether or not that gene is really overexpressed. At the pathway level, if there is activity among a set of 10-15 different genes, it matters less whether any one gene is really overexpressed. For example, in validating the results by IHC, IHC would not be needed on each of the specific genes that were upregulated to see if they, one by one, were upregulated. Rather, IHC is done on as few or as many elements of the pathway as desired/practicable, to see if a significant number of them were affected. Even if they were different pathway elements, the conclusion—that this pathway is activated—would be the same (provided, of course, that the data are broadly consistent—i.e., inhibition vs. activation should be the same).

This approach lowers the possible number of "discoveries" from the number of genes on the chip to the number of pathways that are possibly dysregulated leading to a possible treatment—a few hundred, instead of tens of thousands. One could ask questions like: if there is a pathway consisting of q elements, how many would have to be dysregulated at the $p<0.05$ level to have a $p<0.05$ that the pathway is activated? Algorithms that answer this question are discussed further below and are one of the ways (but only one) by which hypotheses are judged.

For example, to establish with 95% confidence that a pathway was activated by looking at several genes simultaneously, with only 3 samples, if the pathway had 10 elements only 5 of those would need to have 95% confidence; with 20 elements in the pathway, only 7; and with 40 elements, only 9. This calculation assumes approximately 283 different possible pathways (the number of canonical pathways in Ingenuity); as calculated by the statistical algorithm described below. Thus, by looking at pathways rather than individual genes one greatly reduces the number of possible discoveries, and therefore the multiple correction factor; this method requires several genes to be expressed simultaneously. The math works very similarly when triangulating with different technologies.

This method basically devalues the contribution of any one gene, so that inability to establish significance based on a single gene is not fatal. As shown by the statistical algorithm below—a single gene with an incredibly low p value or a large set of genes with moderately low p-values could both yield a significant result, but these are not needed for the invention methods to succeed. Instead of getting large amounts of data by looking at the same gene across a cohort, the present method provides data by looking at related genes within the same patient to achieve significance.

Three different algorithms have been developed to evaluate the significance of an identified pathway hypothesized on the basis of the analyzed data to furnish a target for a therapeutic to analyze them in 3 different ways. Modifications of these to account for any negative data are described as well.

Algorithm 1 is used, independent of the p values of specific data, to determine how many pathway elements must be dysregulated at the 95% confidence level (for instance) to have an overall 95% confidence that the pathway is active.

Algorithm 2 inputs the pathway data—the exact p-values of the various elements—and calculates a p-value of the overall pathway.

Algorithm 3 introduces the concept of "privileged data." For instance, to conclude that the angiotensin pathway is activated, dysregulation of all pathway elements is helpful, but specifically dysregulation of angiotensin and its receptor are more helpful than other components, and this can be reflected in the statistics.

Algorithms 1 and 2 are focused on measuring strength of the hypothesis that the pathway is involved, while algorithm 3 adds biological reasoning that might be useful in identifying hypotheses that are likely to yield fruit in the real world. Additional elements of biological reasoning (such as the "privileged" element concept) can be added incrementally to determine whether they can reproduce the conclusions of a more subtle/sophisticated human interpreter, and if they don't, how further to augment them. Each refinement will add a tunable parameter, which will have to be determined experimentally, and so the more complicated the reasoning, the more data will be required to test/tune the parameter. Algorithms 1 and 2 have no tunable parameters (merely measuring), and algorithm 3 has one tunable parameter (beyond measurement, to prediction).

$$\Pi=1-\{1-[\Sigma_{k=n}^{q}(q|k)(1-p)^{(q-k)}p^{k}]\}^{N} \quad \text{Algorithm 1a}$$

Where $\Pi$=probability that pathway is not noise, p is the threshold probability for a single gene (usually 0.05), n is the number of pathway elements that are dysregulated/amplified/mutated in a manner consistent with the hypothesis, q is the total number of elements in the pathway, N is the total number of possible pathways that might be considered, and (q|k) is q!/k!(q−k)!

Example of utility: If there are, say, 200 possible pathways to consider, then to get a 95% confidence level associated with the pathway activation (after correcting for multiple pathways) a pathway of 10 elements would require 6 of those elements be significant to p=0.05, a pathway of 20 elements would require 7, a pathway of 40 elements would require 9, etc.

Proof: We define $\Pi$ as the probability that, for any one of N pathways, at least n elements out of a possible q have probability <p.

Let $\Pi'$ be the same as $\Pi$ but with respect to a single pathway. Then:

$$\Pi=1-\{1-\Pi'\}^{N}$$

which reduces to the normal Bonferroni correction for small $\Pi'$.

The probability of exactly k elements out of q being dysregulated with probability <p is given by the binomial expansion $$(q|k)(1-p)^{(q-k)}p^{k}$$

and so $\Pi'$ is given as $$\Pi'=\Sigma_{k=n}^{q}(q|k)(1-p)^{(q-k)}p^{k}$$

leading to algorithm 1.

$$\Pi=1-\{1-(q|n)(1-p_{T})^{(q-n)}\Pi_{k=1}^{n}p_{k}\}^{N} \quad \text{Algorithm 2a}$$

Where $\Pi$=probability that pathway is not noise, $p_T$ is the threshold probability for a single gene (usually 0.05), $p_k$ is the p-value for a given gene k, where the genes are ordered from lowest p-value to highest p-value, n is the number of pathway elements that are dysregulated/amplified/mutated, q is the total number of elements in the pathway, N is the total number of possible pathways that might be considered, and (q|n) is q!/n!(q−n)!

Example of utility: The previous formula just considers the case of p=0.05. However, if we have one or more genes with specific p-values that are much smaller, fewer genes may be required to conclude significance.

Proof: We define $\Pi$ as the probability that the probability of a given gene <p for the specific n elements 1, . . . n, with probabilities $p_1, \ldots p_n$.

As in algorithm 1a, let $\Pi'$ be the same as $\Pi$ but with respect to a single pathway. Then:

$$\Pi=1-\{1-\Pi'\}^{N}$$

Here, $\Pi'$ is the probability of exactly n elements out of q being dysregulated with the specific probabilities $p_1, \ldots p_n$, all $<p_T$ while the other q−n elements have $p>p_T$. This is given by $$\Pi'=(q|n)(1-p_{T})^{(q-n)}\Pi_{k=1}^{n}p_{k}$$

where the factor (q|n) derives from the fact that the n significant genes and the q−n non-significant genes could be reordered arbitrarily without changing the result.

Putting these two equations together leads to algorithm 2a.

$$\Pi=1-\{1-[(q+\mu|n+\tau)(1-p_{T})^{(q-n)}\Pi_{k=1}^{n}p_{k}/(\mu|\tau)]^{(1-\beta)}$$
$$[(\mu|\tau)(1-p_{T})^{(\mu-\tau)}\Pi_{r=1}^{\tau}p_{r}]\}^{N} \quad \text{Algorithm 3a}$$

Where $\Pi$=probability that pathway is activated, $p_T$ is the threshold probability for a single gene (usually 0.05), there are $\mu$ privileged elements, of which $\tau$ have $p<p_T$ and there are q non-privileged elements, of which n have $p<p_T$. $p_k$ is the p-value for a non-privileged gene k, and similarly $p_r$ is the p-value for a privileged gene r. $\beta$ is the degree of privilege, with $0 \leq \beta \leq 1$, with $\beta=0$ meaning that there is no privilege (i.e., the elements $\mu$ have the same importance as the elements q), and conversely $\beta=1$ means that the privilege is complete, i.e., the q elements are essentially irrelevant to concluding whether the pathway is activated. N is the total number of possible pathways that might be considered, and (q|n) is q!/n!(q−n)!

Example of utility: In cases where the VEGF pathway appears to be activated (in the sense that the data is inconsistent with the null hypothesis of the data being noise) as determined by algorithms 1a and/or 2a. Biologically, however, a hypothesis in which the VEGF ligand and receptor are specifically dysregulated will carry more weight than those where more ancillary genes are dysregulated, though the ancillary genes are still important to concluding the relevance of the pathway. In this case, $\mu=2$ (the two privileged genes) and $\beta$ represents the magnitude of the relative importance of these genes over the others.

Rationale: Using similar logic as for algorithm 2a, we can define the probability that the patterns seen in the privileged genes are noise by $$[(\mu|\tau)(1-p_{T})^{(\mu-\tau)}\Pi_{r=1}^{\tau}p_{r}]$$

which should be the result for $\beta=1$ (only privileged genes matter), where for $\beta=0$ (privileged genes and non-privileged are of equal importance), the result should reduce to:

$$(q+\mu|n+\tau)(1-p_{T})^{(q+\mu-n-\tau)}\Pi_{k=1}^{n}p_{k}\Pi_{r=1}^{\tau}p_{r}$$

i.e., the same result as if we had never selected out the privileged subgroup μ. The algorithm above reduces to these two extreme cases directly and has other critical properties such as decreasing the contribution of the non-privileged genes monotonically as β increases, being a continuous function of β, etc. Since "degree of privilege" has no independent definition between 0 and 1, any other formula that has these properties can be made equivalent to this one by reparametrizing β. Since the "correct" value for β will have to be measured experimentally in order to most closely reproduce human judgment about the importance of this privilege, all parametrizations of β are of equal value and therefore the formula above represents a correct approach to capturing this level of judgment. This particular parametrization has the property that the log of the probability is a linear function of β, interpolating between the two extremal results.

Even a formula that is non-monotonic in β would technically still be acceptable if β is tuned experimentally, but the results would be more difficult to interpret/understand on an intuitive level.

In the event that there are negative data (i.e., contradictory data that meet the standard of significance, usually 0.05), these algorithms are modified to take this into account, as set forth in algorithms 1b, 2b, and 3b.

To account for negative data, the above algorithms should be modified to $$\Pi = 1 - \{1 - \Pi_+/(\Pi_+ + \Pi_- - \Pi_+ \Pi_-)\}^N$$

where, $\Pi_+$ and $\Pi_-$ are defined in the following algorithm-specific ways:

$$\Pi_+ = [\Sigma_{k=n'}^q (q|k)(1-p)^{(q-k)} p^k] \text{ and } \Pi_- = [\Sigma_{k=n'}^q (q|k)(1-p)^{(q-k)} p^k]$$

Algorithm 1b where n' is the number of statistically significant aberrant genes that are evidence against the hypothesis and all other definitions are as in Algorithm 1a.

$$\Pi_+ = (q|n)(1-p_T)^{(q-n)} \Pi_{k=1}^n p_k \text{ and } \Pi_- = (q|n')(1-p_T)^{(q-n')} \Pi_{k=q-n'}^q p_k$$

Algorithm 2b where n' is defined as in Algorithm 1b, all other definitions are as in Algorithm 2a, and the genes are ordered so that the first n genes are those statistically that are statistically significant in support of the hypothesis, the next q−n−n' genes that have no statistically significant measurement are next, and finally the n' genes that have evidence against the hypothesis are listed.

$$\Pi_+ = [(q+\mu|n+\tau)(1-p_T)^{(q-n)} \Pi_{k=1}^n p_k/(\mu|\tau)]^{(1-\beta)} [(\mu|\tau)(1-p_T)^{(\mu-\tau)} \Pi_{r=1}^\tau p_r] \text{ and}$$

$$\Pi_- = [(q+\mu|n+\tau')(1-p_T)^{(q-n')} \Pi_{k=1}^{n'} p_k/(\mu|\tau')]^{(1-\beta)} [(\mu|\tau')(1-p_T)^{(\mu-\tau')} \Pi_{r=1}^{\tau'} p_r]$$

Algorithm 3b where n' the number of negative data points among the non-privileged genes, τ' is the number of negative data points among the privileged genes, and all other definitions are as in Algorithm 3a.

Proof:

In the case of each of these three algorithms, $\Pi_+$ represents the probability of the hypothesis being false (ignoring the negative data points) while $\Pi_-$ represents the probability of the opposite hypothesis being false (ignoring the positive data points), as per the proofs in each of the 3 previous cases. $H_+$ and $H_-$ are defined as the probabilities of the hypothesis being true and the opposite hypothesis being true, respectively. There are four hypotheses that capture the possible space:

$H_1$: $H_+$ is true and $H_-$ is false
$H_2$: $H_+$ is false and $H_-$ is true
$H_3$: $H_+$ and $H_-$ are both false
$H_4$: $H_+$ and $H_-$ are both true By Bayes' rule, the probability of each hypothesis being true, given the data observed, is $$P(H_i|\text{data}) = P(\text{data}|H_i)P(H_i)/Z, \text{ where } Z = \Sigma_{j=1}^4 P(\text{data}|H_j)P(H_j).$$

Under the null hypothesis (that the data are simply noise), the data sets are independent, so we have $$P(H_1) = (1-\Pi_+)\Pi_-$$

$$P(H_2) = \Pi_+(1-\Pi_-)$$

$$P(H_3) = \Pi_+\Pi_-$$

$$P(H_4) = (1-\Pi_+)(1-\Pi_-)$$

Usually, $P(\text{data}|H_i) = 1$, because the data were observed, in which case the Bayes' rule above reduces to the tautology $$P(H_i|\text{data}) = P(H_i)/Z, \text{ where } Z = \Sigma_{j=1}^4 P(H_i) = 1.$$

However, since $H_4$ is not internally consistent (two hypotheses contradicting each other cannot formally be true), $$P(\text{data}|H_4) = 0.$$

Then Bayes' rule reduces to:

$$P(H_i|\text{data}) = P(H_i)/Z, \text{ where } Z = \Sigma_{j=1}^3 P(H_j) \text{ for } i=1, 2, \text{ or } 3, \text{ and } P(H_4|\text{data}) = 0$$

or specifically, for i=1, plugging in the above gives:

$$P(H_1) = (1-\Pi_+)\Pi_-/(\Pi_+ + \Pi_- - \Pi_+\Pi_-).$$

Since the p-value sought is the probability that $H_1$ is false, before correcting for multiple pathways this is $$1 - P(H_1) = \Pi_+/(\Pi_+ + \Pi_- - \Pi_+\Pi_-).$$

Applying the correction for multiple pathways as in the previous proofs yields the algorithm.

In addition to validating the pathway hypothesized by triangulation as determined using the algorithms above, "integration" also allows more meaningful appreciation of real results against a noisy background, but rather than applying the algorithms to a coherent data set, combines data from multiple technologies, that aren't necessarily used to "playing together", so that they can be viewed and considered simultaneously within the functional biology. For example, the formats for the CNV data are very different from those of the expression data; mutation data are yet different from either. To conclude, "the expression says this, the copy number says that, and they are or are not consistent," is straightforward. It is more difficult to perceive that "Here is something that wouldn't have caught my attention if I were looking individually at either of the data sets, but when looking at them together in the same picture, I see it clearly." For one patient, for instance, before the data were integrated, no hypotheses were found. After building the tools (such as assigning arbitrary values for results in one data set into calculations designed for another data set as described in paragraph [0042]) to integrate them, three good hypotheses emerged. Integration thus has a technical (IT) component and a strategic component to it.

Results

The data and results obtained from an individual patient reveal the relevant disease biology, ties the biology to drugs, and these drugs are tested in the patient. For drugs that work in the individual patient, other patients who suffer that cancer or other cancers, and have the same critical elements are likely to respond the same way to the therapy. A validation study is done to confirm this.

Thus, drugs may include small molecules—e.g., conventional drugs such as Gleevec®, doxorubicin, carboplatin and the like, including investigational drugs. Biologics such as antibodies, therapeutic proteins, gene therapy systems, stem cell therapy systems, and the like, including those in investigational studies may also be used. Use of antibody therapy in tumor treatment is becoming conventional, as is treatment with cytokines and other proteins. Our approach has the ability to exploit the entire pharmacopeia of ~2500 approved drugs as well as investigational agents currently in trials. to engineer an effective customized treatment.

Using the dysregulated pathway information, treatment protocols using drugs or biologics are then proposed and formulated. A database of compounds/biologics/therapies is maintained together with known and suspected targets so that these can be compared to the pathways to determine which protocols are most effective. This is particularly useful in proposing combination therapies, as multiple components of the pathway may be targeted by a multiplicity of components of the protocol.

By utilizing the analysis described herein, the probability of success in treating an individual patient is greatly improved, and the formulated protocol may then be administered to the patient. Routine optimization will determine mode of administration, timing, dosage levels and other parameters relevant to the particular treatment.

In some cases, additional validation studies may be suggested to provide further evidence for the explicated hypotheses. These may include, but not be limited to, studies to assess phosphorylation or other mode of activation of cellular proteins, assessment of mutation status of individual genes, screening of drugs against tumor-derived cells, or various other cell or molecular biology-based assays.

While intuitively it would seem better to analyze a database to look for appropriate targets, that may not be the case. As there are often hundreds of subtypes within a given cancer type, and the search on the database will generally only give information either on the most prevalent subtypes or will give "high level" information. The methods of the present invention give information on rare subtypes, and very "fine-grained" information.

Patients on whom the invention methods are conducted may be those who have failed multiple lines of therapies that have been approved based on results in trials—which by definition focus on the prevalent subtypes, and thus are likely to have rare subtypes. Diagnostics relevant to a rare subtype can be as valuable as those relevant to a common subtype; for example, cKIT mutation in melanoma is only present in 3% of melanomas, but when it is present, Gleevec® is highly effective, so all melanoma patients should be tested for cKIT despite its relative rarity.

The distinction between "high level" vs. "fine grained" information can best be understood by the following example. One distinction among colon cancer patients is whether they have a mutated or wild-type EGFR. This was a test originally used to predict responsiveness to Erbitux™ (two "subtypes"). Later studies revealed that a mutated KRAS predicted a poor responsiveness to Erbitux™ whether or not EGFR is mutated. Both tests are now used in combination (or KRAS alone) to determine susceptibility to Erbitux™. Two subtypes have thus now been split into more. 70% of patients with EGFR mutant, KRAS wild-type, respond to EGFR inhibitors. So there is yet another reason why this is not 100% to be discovered in the future. This will split this subtype into 2 (or more) again where one is yet further enriched for EGFR inhibition response. So, there may be 100 subtypes, with this representing 10 of them, for illustration. The present method, nucleating around a single case rather than a database search, is more likely to distinguish a single subtype from the other 99 rather than a higher-level grouping. In principle, our approach can be used to discover clinically significant subtypes, such as EGFR mutant cancers with mutated KRAS, in a single individual. If validated in other patients, these new subtypes can become valuable additions to the high level databases and standard panels of point mutations used to stratify patients.

The following examples are offered to illustrate but not to limit the invention.

EXAMPLE 1

Formulation of Treatment for Colon Cancer in a Patient

Colon tumor tissue and colon normal tissue, as well as tissue from a liver metastasis from an individual patient were biopsied and subjected to Affymetrix transcription profiling. Ratios of gene expression (mRNA levels) from the primary colon tumor and liver metastasis samples, both relative to normal colon tissue samples were determined. Genes with an expression ratio threshold of 1.8-fold up- or down-regulation, and a significance P-value of 0.05 in malignant relative to normal cells were identified as 288 genes from the colon tumor and 348 genes from the liver metastasis.

Using a tool provided by Ingenuity Systems, the identified genes were subjected to an algorithm which finds highly interconnected networks of interacting genes (and their corresponding proteins). Ingenuity's algorithm for constructing a network graph is based on hand-curating protein/protein interactions (as defined by physical and/or functional interactions) directly from the research literature. In each individual analysis, the Ingenuity algorithm compares the regulated genes to this underlying master network and clusters of proteins that have multiple mutual interactions are identified and presented as smaller sub-networks. The resulting pathways can be directly supported by references to the literature both within the Ingenuity tool, and independently. [Similar algorithms are in use by other tools (e.g., those by GeneGo, and one in the public domain); we use Ingenuity because their database of curated literature is currently the most comprehensive, but the work is not conditioned on them specifically.] These findings were then further analyzed independently of the Ingenuity tool, to find particularly relevant pathways which could provide potential therapeutic targets.

An initial analysis was done to confirm that the global gene expression from the tumor sample was generally consistent with a priori expectations for neoplasms of this type. The networks that were assembled by the protein interaction algorithm from the list of up- or down-regulated genes were analyzed with respect to the cellular and organismal functions of their individual component genes. From the primary colon tumor sample, the four top-scoring networks (with respect to the interconnectedness of their component genes) were greatly enriched in the following functions:

| | |
|---|---|
| Cancer | Cellular Movement |
| Cell Morphology | Neurological Disease |
| Protein Synthesis | Connective Tissue Disorders |
| Gastrointestinal Disease | Cell Signaling |
| Carbohydrate Metabolism | Molecular Transport |
| Small Molecule Biochemistry | |

From the liver metastasis sample, the four top-scoring networks (with respect to the interconnectedness of their component genes) were greatly enriched in the following functions:

| | |
|---|---|
| Genetic Disorder | Hematological Disease |
| Ophthalmic Disease | Lipid Metabolism |
| Small Molecule Biochemistry | Protein Synthesis |
| Hematological System Development and Function | Organismal Functions |
| Infectious Disease | Post-Translational Modification |
| Protein Folding | Cancer |

This overall pattern is consistent with what one might expect from the global gene expression of a tumor sample, as compared to normal tissue. This helps to confirm that the differently expressed genes are from the tumor sample and that the integrity of the gene expression milieu has been maintained. The entire list of networks and their associated functions, from both samples, is set forth at the end of this Example.

Both entire lists of differently expressed genes were scored for associated cellular functions. In the primary tumor, the highest scoring category was cancer. (FIG. 1)

Figure 2:
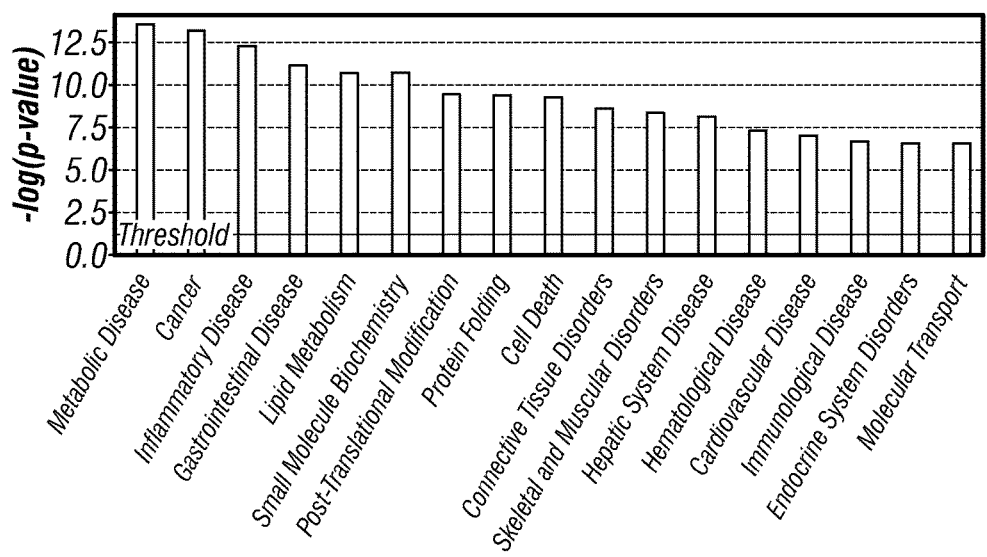
FIG. 2 is a graph showing the cellular functions enriched in regulated genes from a liver metastasis sample derived from the same patient whose colon cancer is diagrammed in FIG. 1.
Figure 2:
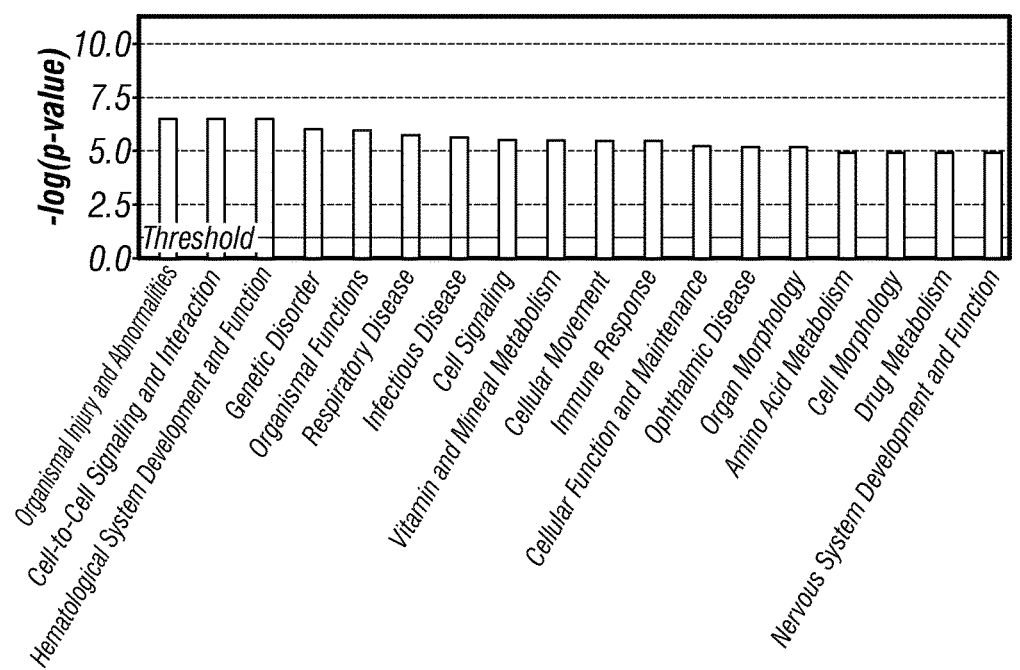

A similar analysis of the cellular functions associated with the individual dysregulated genes from the liver metastasis is shown below (FIG. 2). Genes were highly enriched in cancer-related functions, similar to the primary tumor, but there was also much dysregulation of metabolic disease and lipid-metabolic genes. This may either represent some normal liver contamination of the sample, or less likely some hepatic-like differentiation of the metastatic tissue.

Figure 3A:
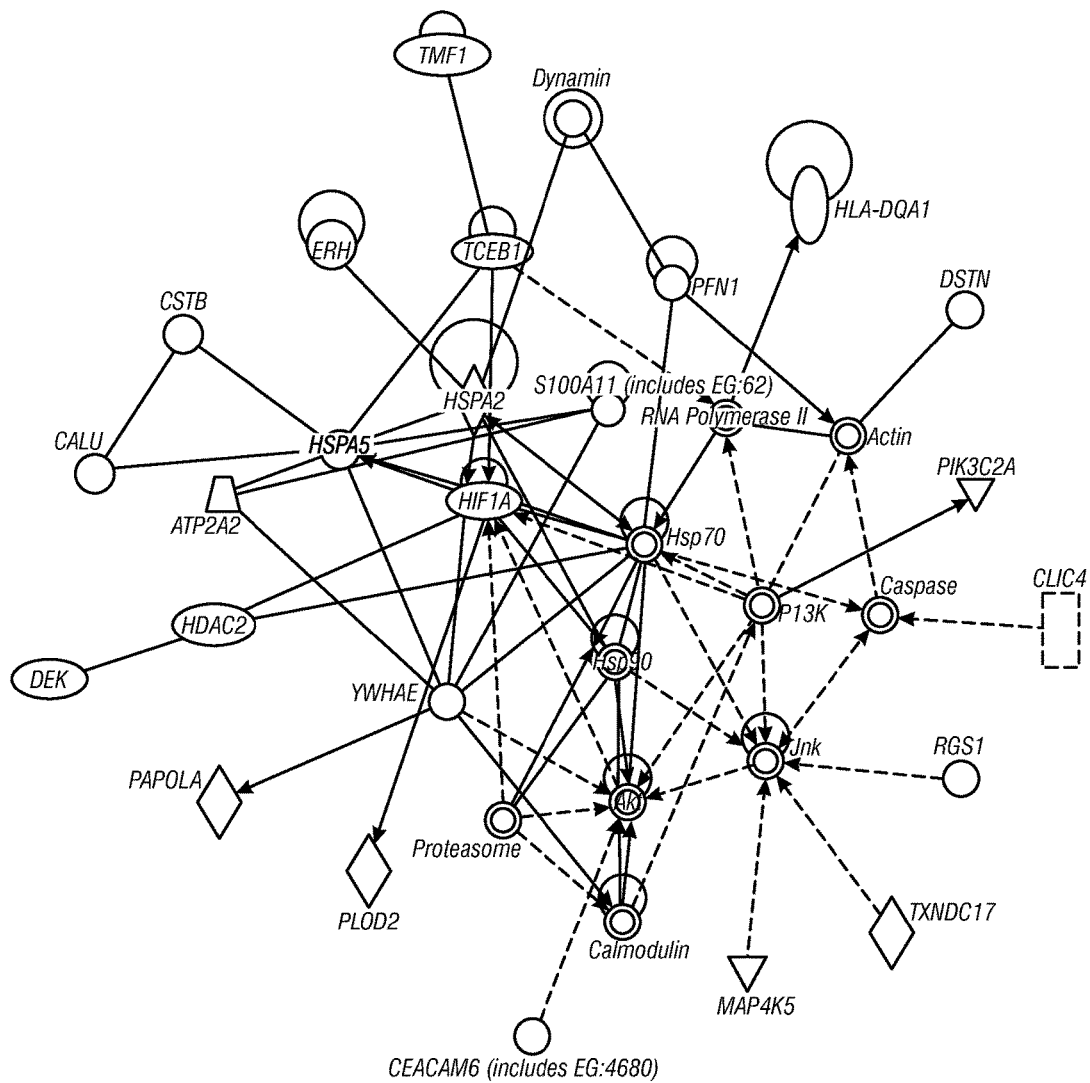
FIGS. 3A-3B show a diagrams of protein interaction networks deduced by the method of the invention from (FIG. 3A) primary colon tumor and (FIG. 3B) liver metastasis.
Figure 3B:
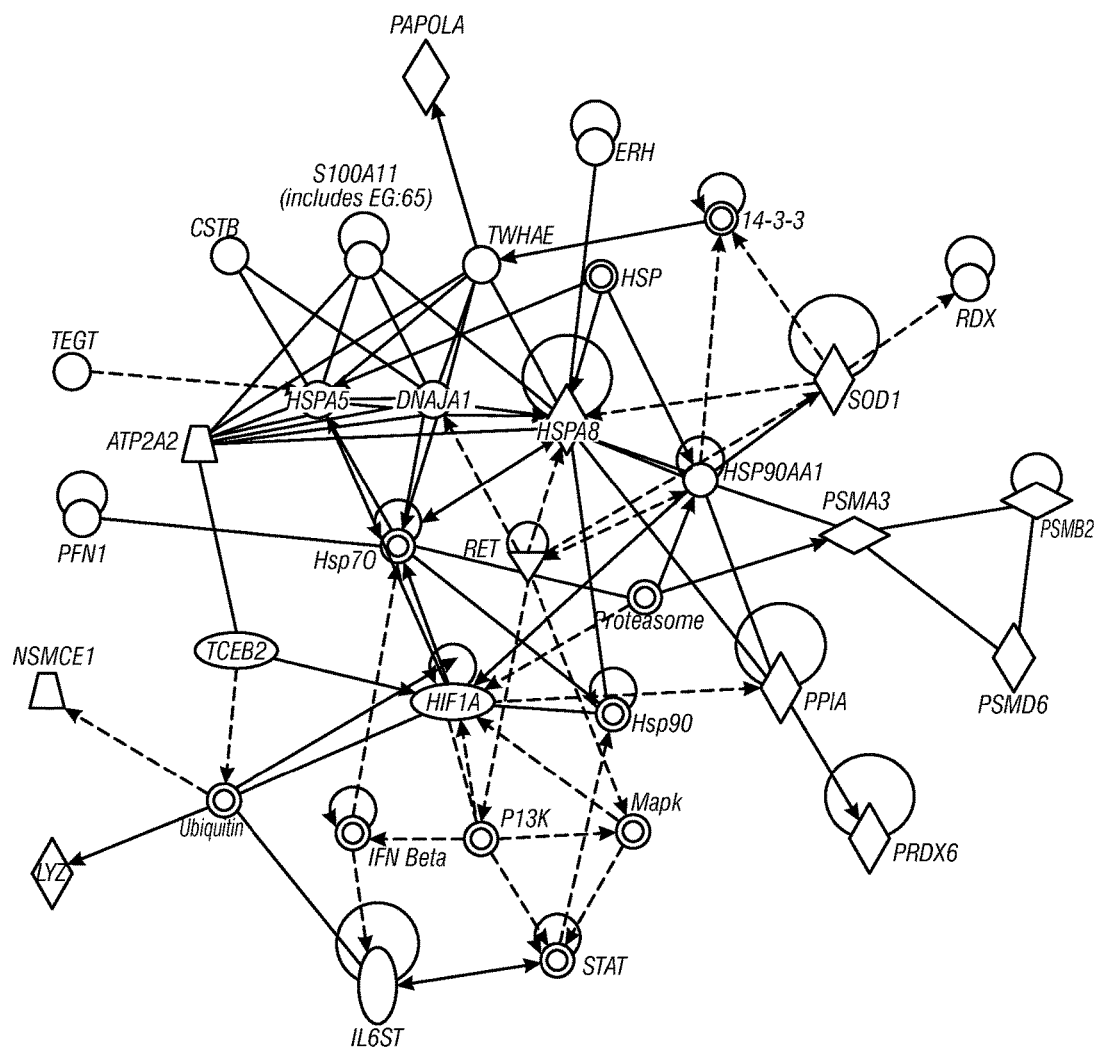

The network analysis yielded several findings of note. A first attempt was made to find pathways that were dysregulated in both the primary tumor and the liver metastasis in the hopes of targeting both sites. Following this strategy, two networks with similar features in both tumors were identified (FIGS. 3A and 3B). While there were differences in several individual genes in the two networks, commonalities included up-regulation of HIF1A, a transcription factor involved in tumor adaptation to, and survival in, hypoxic conditions. Also, in this network in both tumor sites, several members of the heat-shock protein (Hsp) family were present. Hsp family members have been appreciated as playing a role in tumorigenesis and maintenance (Xiang, T. X., et al., *Tumori*. (2008) 94:593-550, Yi, F., et al., *ACS Chem. Biol.* (2008) 46:181-191). Upon further examination of the individual Hsp family members up-regulated at the two sites, there was no individual member common to both sites that would be targeted by an approved, marketed drug, although there are investigational drugs against these targets.

Figure 4:
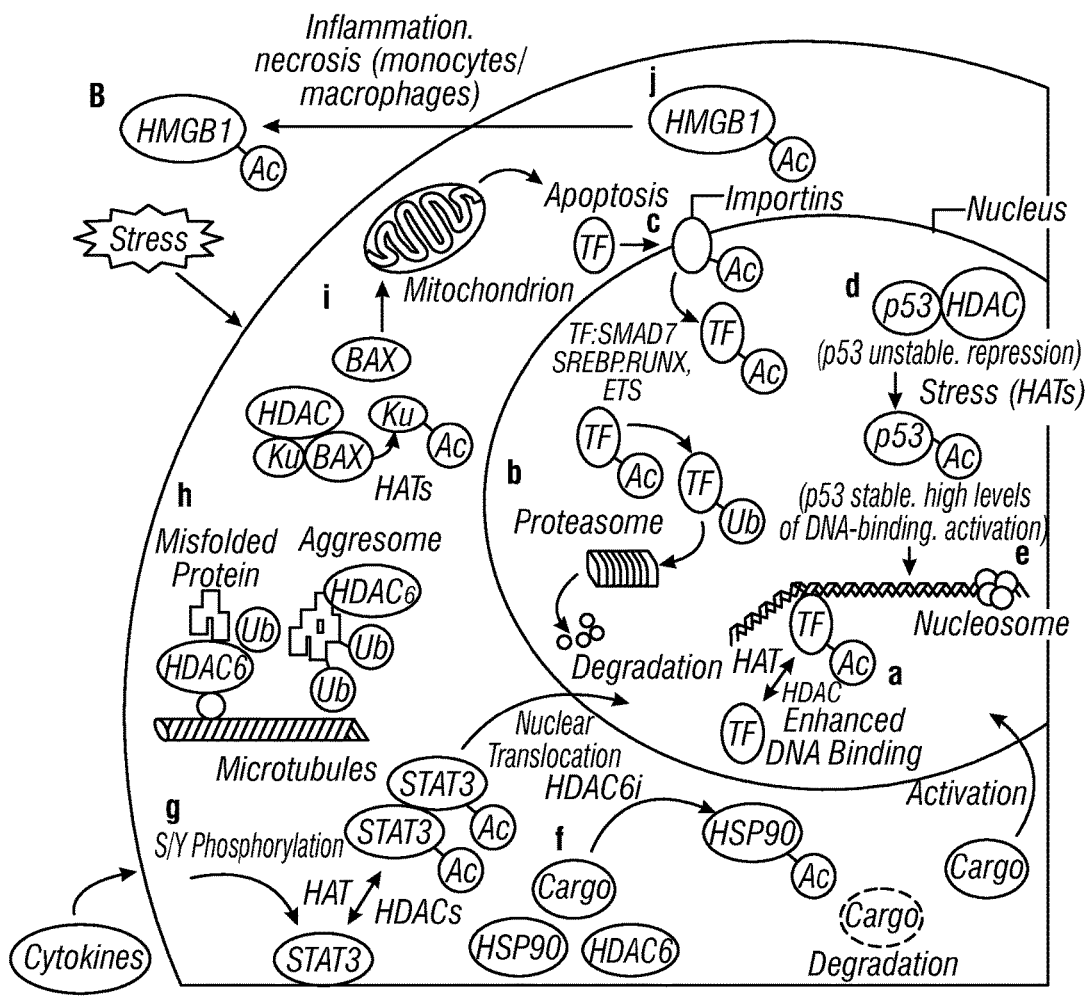
FIG. 4 is a diagram of HDAC-Hsp cellular interactions as described in the art.

However, it may be possible to indirectly target the Hsp pathways by inhibiting a family of proteins that interacts with them, the histone deacetylases (HDACs). HDACs were first identified as enzymes which deacetylated histone proteins, but more recently have been shown to have a wider array of substrates. One member, HDAC2 is up-regulated in the primary tumor and expressed in the liver metastasis. Other family members, including HDAC6 are expressed in both the primary tumor and the metastasis sample. It has been shown in the literature that HDAC inhibition is pro-apoptotic and has anti-tumor properties, through several mechanisms. One of these mechanisms is via hyperacetylation, and hence deactivation, of members of the Hsp family by HDAC6. In particular, Hsp90, which is up-regulated in both primary tumor and metastasis, has been shown to be deactivated by HDAC inhibition. FIG. 4, below, illustrates HDAC-Hsp interactions. There are several drugs inhibiting HDACs, including HDAC2 and HDAC6, such as vorinostat (Zolinza®).

An additional finding was that in the liver metastasis, the receptor tyrosine kinase, RET, and its surrounding pathway, were up-regulated (see FIG. 3B). RET is a proto-oncogene which is often up-regulated in endocrine tumors, however it has also recently been associated with breast cancers and neuroblastoma (Boulay, A., et al., *Cancer Res.* (2008) 68:3743-3751, Beaudry, P., et al., *Mol. Cancer Ther.* (2008) 7:418-424). Inhibiting RET would presumably selectively target the metastases only; however this may not be an issue as the primary tumor has been resected. Additionally, Sutent® is an inhibitor of RET.

The patient might be treated by inhibiting HDAC2 which should target both the primary tumor and the liver metastasis via deactivation of Hsp and other antitumor properties of HDAC inhibition. It is also possible to target liver metastases using sunitinib Sutent® to inhibit RET.

TABLE 1

Regulated Networks from Primary Colon Tumor Sample

| ID | Molecules in Network | Score | Focus Molecules | Top Functions |
|---|---|---|---|---|
| 1 | BHLHB2, COL1A2, ERK, GOPC, HSP90B1, IL6ST, ITGAV, LOX, LUM, LYZ, MRLC2, NEXN, Pak, PDGF BB, POSTN, PSMA3, PSMD6, RAB1A, RAD23B, RHOA, Rock, ROCK1, S100P, SFRS10, SH3PXD2A, SKIL, SNRPF, SNRPG, SPARC, SUB1, TFIIH, Tgf beta, Ubiquitin, VCAN, VIM | 50 | 28 | Cancer, Cellular Movement, Cell Morphology |
| 2 | ANXA2, C3-Cfb, CAPZA1, CD55, CFH, CFI, DAD1, DDX5, EIF3E, EIF3H, FSH, G0S2, GJB2, GTF3A, hCG, HSPH1, LDHA, LDHB, LDL, MCL1, NFkB, PAIP2, PAWR, PLC, PTP4A1, RAB2A, RPL15, RPL39, RPS3A, S100A10, SERPINB5, TCP1, TPT1 (includes EG: 7178), UBE2K, Vegf | 50 | 28 | Neurological Disease, Protein Synthesis, Connective Tissue Disorders |
| 3 | Actin, Akt, ATP2A2, Calmodulin, CALU, Caspase, CEACAM6 (includes EG: 4680), CLIC4, CSTB, DEK, DSTN, Dynamin, ERH, HDAC2, HIF1A, HLA-DQA1, Hsp70, Hsp90, HSPA5, HSPA8, Jnk, MAP4K5, PAPOLA, PFN1, PI3K, PIK3C2A, PLOD2, Proteasome, RGS1, RNA polymerase II, S100A11 (includes EG: 6282), TCEB1, TMF1, TXNDC17, YWHAE | 40 | 24 | Cancer, Gastrointestinal Disease, Cell Signaling |

TABLE 1-continued

Regulated Networks from Primary Colon Tumor Sample

| ID | Molecules in Network | Score | Focus Molecules | Top Functions |
|---|---|---|---|---|
| 4 | C15ORF15, D-glucose, EWSR1, FGA, Histone h3, HNF4A, HOOK3, KRR1, LAPTM4A, MRPL33, MRPS18C, N4BP2L2, PDE4DIP, SEC31A, SMAD4, SSBP1, TBC1D16, THYN1, TINP1, TM9SF2, USMG5, VPS29 | 28 | 16 | Carbohydrate Metabolism, Molecular Transport, Small Molecule Biochemistry |
| 5 | ACTA2 (includes EG: 59), ALP, Ap1, Arp2/3, ATP5E, BMPR2, C3ORF10, CALD1, CSNK1A1, DCN, F Actin, FN1, GJA1, Histone h3, IFI16, IK, IL12, Insulin, Interferon alpha, KIAA0265, Mapk, Mmp, NCKAP1, Nfat, P38 MAPK, Pdgf, Pka, Pkc(s), PPIC, Rac, RAC1, S100A4, Scf, SPP1, TIMP2 | 27 | 18 | Cell-To-Cell Signaling and Interaction, Cellular Assembly and Organization, Cellular Movement |
| 6 | ACTA2 (includes EG: 59), ANKH, BHLHB2, BIRC6, CCNK, CGGBP1, CHD3, COMMD6, COMMD1 (includes EG: 150684), FMR1, H2AFZ, HIPK1, MAT2A, MCL1, NFIL3, NXF1, PDGF BB, PPA1, PRPF40A, PRRX2, RELA, RFFL, RNF25, SFRS10, SON, THOC7, TP53, TTC3, UBE2A, UBE2B, UBE2D2, UBE2D3, UBQLN2, UBR3, WBP5 | 27 | 18 | Protein Degradation, Protein Synthesis, Viral Function |
| 7 | ACTA2 (includes EG: 59), BET1, CCDC90B, CDK5RAP3 (includes EG: 80279), CISD1, COPB2, COPZ1, COX7A2, CREBL1, CSDE1, HNF4A, HSPA4L, MCF2, MITD1, NFYB, PHF5A, PI4KB, PRDX5, PRKAB1, RAB10, RAB11A, RTCD1, SCFD1, SF3B1, SF3B4, SF3B14, SYTL3, TAX1BP1, TBC1D17, TMEM93, TSNAX, UBE2D3, UFM1, USP5, YKT6 | 25 | 17 | Cellular Assembly and Organization, Cell Morphology, Connective Tissue Development and Function |
| 8 | ATL3, ATP6V1B2, CLK4, CPNE1, CSNK1A1, CTGF, DDX1, DHX15, EIF5B, FAP, GCC2, HAT1, HEBP2, ITGA1, ITGA3, ITGAE, KITLG (includes EG: 4254), L-1-tyrosine, LOC100128060, MIA, MYCN, PDCD6, RELN, retinoic acid, RPL19, RPS19, RPS23, RPS17 (includes EG: 6218), SLC38A2, SNAI2, SPARC, TBC1D8, TGFBI, VEGFA, YWHAZ | 23 | 16 | Cell-To-Cell Signaling and Interaction, Cancer, Cellular Growth and Proliferation |
| 9 | BTF3 (includes EG: 689), C12ORF35, Ck2, DDX17, DICER1, HMGN1, HNRNPA1, HNRNPA2B1, HNRNPC, LSM2, LSM3, LSM4, LSM5, LSM7, LSM8, LSM6 (includes EG: 11157), MED21, NAP1L1, NONO, NOP5/NOP58, PICALM, PRPF8, RPL37, SAFB, SART3, SFRS3, SFRS12, SIP1, SMN2, SNRPA1, SNRPD1, SNRPD2, SNRPD3, SNRPE, SSB | 21 | 15 | RNA Post-Transcriptional Modification, Cellular Assembly and Organization, Cellular Compromise |
| 10 | BCAS1, beta-estradiol, BNIP3 (includes EG: 664), CCNA1, CCNF, CDR1, CHMP2B, CKS1B, DYNLL1, ERBB2, GLB1, HTRA1, hydrogen peroxide, IRF6, KRT81 (includes EG: 3887), LARP5, NUCKS1, PIK3C2A, PKIA, PKIB, PRDX5, PRDX6, PRSS23, PTP4A2, RAB9A, S100A2, SKP1, SPARC, SSR1, SSR3, TERT, thiobarbituric acid reactive substances, WWC1, ZBTB7A, ZNF638 | 21 | 15 | Cancer, Cellular Growth and Proliferation, Reproductive System Disease |
| 11 | ANXA4, ASPN, CCL18, CCL19, CD40LG, chondroitin sulfate, CNN3, CSDA, CTSH, CXCL2, DDX5, EEA1, EGLN1, FSCN1, HLA-DQA1, IFNG, ITGB7, KDELR2, KIF2A, LOX, MARCKSL1, METAP2 (includes EG: 10988), MMP11, MYC, NAPG, NEDD9, NSF, PLS3, POMP, RPS15A, SAMD9, SERINC3, TGFB1, WISP1, YME1L1 | 21 | 15 | Cell-To-Cell Signaling and Interaction, Hematological System Development and Function, Immune and Lymphatic System Development and Function |
| 12 | ARHGEF18, BRCA1, BTF3 (includes EG: 689), CMTM6, CSDE1, CUL2, E3 RING, FSCN1, GH1, MCC, MRPL36, NOVA1, NPEPPS, PDCD5, RHPN2, RNF126, RPL35, SEC62, SEC63, SEC61A1, SEC61B, SEC61G, SEPT2, SEPT7, SEPT9, SEPT11, SF3B14, TAGLN2, TBCA, TMCO1, TMED2, TRAF6, TXNDC1, UBE2D3, VHL | 21 | 15 | Protein Synthesis, Post-Translational Modification, Cellular Assembly and Organization |
| 13 | 4-phenylbutyric acid, ANGPT2, ARNT2, ATIC, C14ORF156, CD247, CD3E, CDV3, COL12A1, COL4A5, Cpla2, CUL2, CYBA, DEF6, EDIL3, FCGR2C, GAB2, HNRPDL, KCNK3, LRRFIP1, MAT2A, NASP, OAZ1, SEPP1, SIRPA, SNRP70, spermine, TAX1BP1, TNF, TNFRSF9, TRA2A, TRAF6, UACA, YPEL5, ZAP70 | 17 | 13 | Cell Signaling, Molecular Transport, Vitamin and Mineral Metabolism |

TABLE 1-continued

Regulated Networks from Primary Colon Tumor Sample

| ID | Molecules in Network | Score | Focus Molecules | Top Functions |
|----|---------------------|-------|-----------------|---------------|
| 14 | AATF, ATN1, CCDC99, CDKN1A, CTCF, CYP27B1, E2F1, E2F6, EFEMP1, EIF1, EPC1, FBLN2, FEN1, HIST2H2AA3, IL2, ITM2B, KRAS, MEGF8, NAB1, NAB2, PCSK5, PTPRJ, PTRH2, REEP5, RERE, RPA3, RYBP, S100A4, Scf, SNF8, SP2, TFDP2, TSG101, VPS36, ZBED5 | 15 | 12 | Gene Expression, Cell Cycle, Connective Tissue Development and Function |
| 15 | C7ORF43, TMEM50A | 2 | 1 | |
| 16 | GPI, PARP14 | 2 | 1 | Cancer, Cell Morphology, Cell-To-Cell Signaling and Interaction |
| 17 | ENY2, MCM3AP | 2 | 1 | Gene Expression, DNA Replication, Recombination, and Repair, Molecular Transport |
| 18 | C1GALT1, Glycoprotein-N-acetylgalactosamine 3-beta-galactosyltransferase | 2 | 1 | Cardiovascular System Development and Function, Cell-To-Cell Signaling and Interaction, Connective Tissue Development and Function |
| 19 | C21ORF66, GRIN1 | 2 | 1 | Cardiovascular Disease, Cell Death, Cell-To-Cell Signaling and Interaction |
| 20 | DUB, USP34 | 2 | 1 | |
| 21 | DNAJC, DNAJC15, Hsp22/Hsp40/Hsp90 | 2 | 1 | Carbohydrate Metabolism, Drug Metabolism, Molecular Transport |
| 22 | NADH2 dehydrogenase, NADH2 dehydrogenase (ubiquinone), NDUFC2 | 2 | 1 | Cancer, Gastrointestinal Disease |

TABLE 2

Regulated Networks from Liver Metastasis Sample

| ID | Molecules in Network | Score | Focus Molecules | Top Functions |
|----|---------------------|-------|-----------------|---------------|
| 1 | ABCA6, APCS, APOC1, APOC3, C3-Cfb, CFB, CFH, CFI, CP, CPB2, CTSL1, ERK, FG, FGA, FGB, FGG, Fibrin, FTL, GDI2, HP, HRG, HSBP1, Mmp, NAMPT, NTN4, QDPR, RAB1A, RAB8A, S100P, SAA4, SERPIND1, SSBP1, Stat3-Stat3, TFF2, TTR | 47 | 29 | Genetic Disorder, Hematological Disease, Ophthalmic Disease |
| 2 | ABCD3, AKR1C4, C14ORF156, Ck2, CREBL2, DYNLL1, E2f, EIF5, EIF3H, EIF3J, FSH, Histone h3, HLA-DQA1, HNRNPA1, HNRNPA2B1, HSPC152, IFITM2, IFITM3, IL12, Interferon alpha, ITM2B, KIAA0265, LDHA, MHC Class II, MT1G, NONO, PARP9, PGRMC1, PHYH, PTP4A1, RNA polymerase II, SC4MOL, SFRS5, SLC27A2, TFF1 | 45 | 27 | Lipid Metabolism, Small Molecule Biochemistry, Protein Synthesis |
| 3 | APOA2, APOB, APOF, B2M, C5, C6, C7, C1q, C1R, C5-C6-C7, C5-C6-C7-C8, C8B, CALR, Complement component 1, CXCL16, DAD1, F5, F9, G0S2, HAMP, HDL, HSP90B1, IgG, LMAN1, MHC Class I, NFkB, P4HB, PDIA3, PRDX4, PROS1, SAA@, SERPINC1, SERPING1, TFPI, WTAP | 41 | 26 | Hematological System Development and Function, Organismal Functions, Infectious Disease |
| 4 | 14-3-3, ATP2A2, CSTB, DNAJA1, ERH, HIF1A, HSP, Hsp70, Hsp90, HSP90AA1, HSPA5, HSPA8, IFN Beta, IL6ST, LYZ, Mapk, NSMCE1, PAPOLA, PFN1, PI3K, PPIA, PRDX6, Proteasome, PSMA3, PSMB2, PSMD6, RDX, RET, S100A11 (includes EG: 6282), SOD1, STAT, TCEB2, TEGT, Ubiquitin, YWHAE | 40 | 25 | Post-Translational Modification, Protein Folding, Cancer |
| 5 | ACADM, ACAT1, Akt, ALB, ALDOB, AMPK, ANGPTL3, APOH, ATP5E, ATP5J2, ATP5L, COX5A, COX6C, COX7B, COX7C, CYB5A, Cytochrome c oxidase, H+-transporting two-sector ATPase, Hnf3, Insulin, LEPR, NADH dehydrogenase, NADH2 dehydrogenase, NADH2 dehydrogenase (ubiquinone), NDUFA1, NDUFA2, NDUFA4, NDUFAB1, NDUFB6, SCD, SLC2A2, TAT, Tcf 1/3/4, TMBIM4, Vegf | 38 | 24 | Energy Production, Nucleic Acid Metabolism, Small Molecule Biochemistry |

TABLE 2-continued

Regulated Networks from Liver Metastasis Sample

| ID | Molecules in Network | Score | Focus Molecules | Top Functions |
|---|---|---|---|---|
| 6 | A2M, ADFP, ALDH1A1, BNIP3 (includes EG: 664), CAR ligand-CAR-Retinoic acid-RXR&alpha, CAT, CD14, CYP2B6 (includes EG: 1555), CYP2C8, CYP2C19, CYP2E1, CYP3A5, FABP1, GST, GSTO1, HSPE1, IGFBP1, Jnk, MGST2, MT1F, NADPH oxidase, Ncoa-Nr1i2-Rxra, Ncoa-Nr1i3-Rxra, P38 MAPK, PDGF BB, PXR ligand-PXR-Retinoic acid-RXR&alpha, Rxr, SAT1, SERPINA2, SNRPG, Trypsin, TXNDC17, UGT2B4, Unspecific monooxygenase, VitaminD3-VDR-RXR | 33 | 22 | Small Molecule Biochemistry, Drug Metabolism, Endocrine System Development and Function |
| 7 | C12ORF62, CEBPB, CWC15, HNF1A, HNF4A, HSDL2, LAPTM4A, MRP63, MRPL33, MRPL51, MRPS28, MT1X, N4BP2L2, ONECUT1, SEC11C, SLC38A4, TINP1, TM4SF4, TMEM123, TMEM176A | 27 | 16 | Gene Expression, Cellular Development, Hepatic System Development and Function |
| 8 | ALB, AOX1, ATXN2, BNIP3 (includes EG: 664), CYC1, CYTB, DAD1, FGF2, FTH1, Gsk3, hemin, iron, ITM2B, KRAS, LCP1, LRAT, MAPK9, MYCN, PLS3, retinoic acid, RPS7, SERPINA7, SLC38A2, SPINK1 (includes EG: 6690), TMED2, Ubiquinol-cytochrome-c reductase, UQCR, UQCRB, UQCRC2, UQCRFS1, UQCRFSL1, UQCRH, UQCRQ, VHL | 24 | 17 | Cellular Assembly and Organization, Lipid Metabolism, Molecular Transport |
| 9 | ANXA2, Ap1, ARHGEF12, Calpain, Cpla2, F2, F Actin, Filamin, FN1, GJB2, hCG, IL1, LAMP2, LDL, MT2A, PAH, Pak, Pdgf, Pkc(s), PLC, Pld, PP2A, Rap1, Ras homolog, RHOA, Rock, S100A10, SAR1B, SMARCA1, SPP1, ST6GAL1, SUB1, Tgf beta, TIMP1, UBE2K | 23 | 17 | Cell-To-Cell Signaling and Interaction, Cellular Assembly and Organization, Cancer |
| 10 | ACAA2, AIP, AKR1C4, BAAT, BET1, BRD4, C6ORF203, CCDC45, CLDN1, CLDN3, FOXA2, GJB1, GOT1, HAO1, HNF4A, HSD17B4, INADL (includes EG: 10207), LSM3, LSM4, LSM5, LSM10, MAL2, NR5A2, PBLD, SART3, SCFD1, SH3BGRL2, SHFM1, SNRPD2, SNRPD3, SNRPE, STRAP, TDO2, VPS29, YKT6 | 23 | 17 | Lipid Metabolism, Small Molecule Biochemistry, Endocrine System Disorders |
| 11 | 3-alpha,17-beta-androstanediol, 3-beta,17-beta-androstanediol, ALB, beta-estradiol, C11ORF10, CDH5, CFHR4, cholesterol, COMMD6, CPS1, CYB5A, CYP3A4, DDR1, Gsk3, HSD17B6, IDH1, IL12B, IRS2, ITGAM, LEAP2, LEP, MAPK9, MMP12, MYBL1, PCSK1, PIK3C2A, PON3, RELA, RPL36AL, SC4MOL, SC5DL, TBC1D8, TTPA, UGP2, VEGFA | 23 | 17 | Endocrine System Development and Function, Small Molecule Biochemistry, Metabolic Disease |
| 12 | AADAC, ACADSB, ACTA2 (includes EG: 59), ADH4, ALB, AMBP, ANXA2, ASPN, BMP2, CDH11, CHRDL2, CTNNB1, CTSS, CYC1, F13A1, FGF6, GDF10, HNF1A, HRAS, ITGAE, KDELR2, LEO1, LGALS3, MAPK9, NR5A2, NUCB2, PCCA, PCSK6, phosphate, PZP, RPL37, RPS17 (includes EG: 6218), TBCA, TGFB1, TTC1 | 20 | 15 | Cell-To-Cell Signaling and Interaction, Skeletal and Muscular System Development and Function, Tissue Development |
| 13 | ACTA2 (includes EG: 59), AFM, ALB, APP, AUH, CD4, CD40LG, CFHR5, Cu2+, CUGBP2, DECR1, F12, GATM, hemin, heparin, HIST1H2BK, HPR, IFNG, IL4, IL13RA1, ITIH2, MAPK9, NFYB, POMP, RNASE3, RRAGA, RRAGD, SEPP1, SERPINA5, SERPINA6, SON, TFCP2, TMEM93, TNFAIP2, UHRF1 | 20 | 15 | Organismal Injury and Abnormalities, Tissue Morphology, Cell-To-Cell Signaling and Interaction |
| 14 | ACTA2 (includes EG: 59), ALB, ARG1, ARRDC3, butyric acid, CARHSP1, CCL18, CD4, CDH11, CTSF, DDR1, DDT, G0S2, GC, Gsk3, GTF3A, HLA-DRA, IFNGR2, IK, IL15, IL18R1, MAPK9, MMP12, NNMT, NUP85, PAIP2, PIAS4, PRKRIR, PTP4A1, SYAP1, SYNPO, TNF, TNFAIP2, TP53, Vegf | 18 | 14 | Inflammatory Disease, Immunological Disease, Viral Function |
| 15 | Actin, C5, C6, C7, C8, C9, C21ORF66, C5-C6-C7-C8, C5-C6-C7-C8-C9, C8A, C8B, C8G, Calmodulin, CAMK2B, Caspase, CCL13, CD59, CIAO1, Cyp2b, CYP2B7P1, Cytochrome c, dihydrotestosterone, FAM96A, GRIN1, ICAM1, IFNA1, IRS2, MYO1B, pyridine, RGN, RPS29, SEPP1 | 16 | 13 | Cell Death, Hematological Disease, Organismal Injury and Abnormalities |

TABLE 2-continued

Regulated Networks from Liver Metastasis Sample

| ID | Molecules in Network | Score | Focus Molecules | Top Functions |
|---|---|---|---|---|
| 16 | amino acids, ARL6IP1, ATM, CDC2L1 (includes EG: 984), CDC45L, CDKN1A, CHD2, CTCF, CTDP1, CTSK, E2F1, EIF1, GLUD1, GNPNAT1, Gsk3, HGF, IL2, ITM2B, KIAA0999, LGALS3, MAP3K1, MAPK9, MYC, PTRH2, Ras, RPL38 (includes EG: 6169), RPS13 (includes EG: 6207), RPS15A, RPS27L, Scf, TGFA, TPT1 (includes EG: 7178), UBE2S, VCP, ZBED5 | 16 | 13 | Cancer, Cell Death, Hematological Disease |
| 17 | 3-hydroxyisobutyryl-CoA hydrolase, HIBCH | 2 | 1 | |
| 18 | ENY2, MCM3AP | 2 | 1 | Gene Expression, DNA Replication, Recombination, and Repair, Molecular Transport |
| 19 | PCSK6, PRG4 (includes EG: 10216) | 2 | 1 | Cancer, Cell Morphology, Cellular Development |
| 20 | BHMT2, TAL1 | 2 | 1 | Cardiovascular System Development and Function, Embryonic Development, Hematological System Development and Function |
| 21 | IMP3, LPXN, MPHOSPH10 | 1 | 1 | RNA Post-Transcriptional Modification, Post-Translational Modification, Protein Synthesis |
| 22 | E2F6, EPC1, REEP5 | 1 | 1 | Gene Expression, Cellular Growth and Proliferation, Cancer |
| 23 | DNAJC, DNAJC15, Hsp22/Hsp40/Hsp90 | 1 | 1 | Carbohydrate Metabolism, Drug Metabolism, Molecular Transport |
| 24 | CIC, RHOJ, SEC62, SEC63 | 1 | 1 | Cancer, Hepatic System Disease, Protein Synthesis |

Additional References

Mariadason, J. M., et al., *Epigenetics* (2008) 3:28-37. HDACs and HDAC inhibitors in colon cancer.

Yang, R, et al., *Cancer Res.* (2008) 68:4833-4842. Role of acetylation and extracellular location of heat shock protein 90alpha in tumor cell invasion.

EXAMPLE 2

Formulation of Treatment for Patient with Lung Cancer

Biopsy samples from the patient's tumor and normal tissue were assayed for mRNA levels using Affymetrix transcription profiling. Genes with an expression ratio threshold of 3-fold up- or down-regulation, and a significance P-value of 0.05 yielded 4,519 unique genes.

Using a tool provided by Ingenuity Systems, the 4,519 genes were subjected to an algorithm which finds highly interconnected networks of interacting genes (and their corresponding proteins). Protein/protein interaction is determined directly from the research literature and is incorporated into the algorithm. These findings were then further analyzed to find particularly relevant pathways which could provide potential therapeutic targets or, if possible, clusters of interacting proteins which potentially could be targeted in combination for therapeutic benefit.

An initial analysis was done to confirm that the global gene expression from the tumor sample was generally consistent with a priori expectations for a neoplasm of this type. This serves as a crude measure of quality control for tissue handling and microarray processing methodology. The networks that were assembled by the protein interaction algorithm from the filtered list of up- or down-regulated genes were analyzed with respect to the cellular and organismal functions of their individual component genes. The three top-scoring networks (with respect to the interconnectedness of their component genes) were greatly enriched in the following functions:

| | |
|---|---|
| Cancer | Cellular Assembly and Organization |
| Cellular Function and Maintenance | RNA Post-Transcriptional Modification |
| Embryonic Development | Cell Cycle |

This overall pattern is consistent with what one might expect from the global gene expression of a tumor sample, as compared to normal tissue, and help to confirm that the data are from the tumor sample and that the integrity of the gene expression milieu has been maintained. The entire list of networks and their associated functions is set forth at the end of this example.

Figure 5:
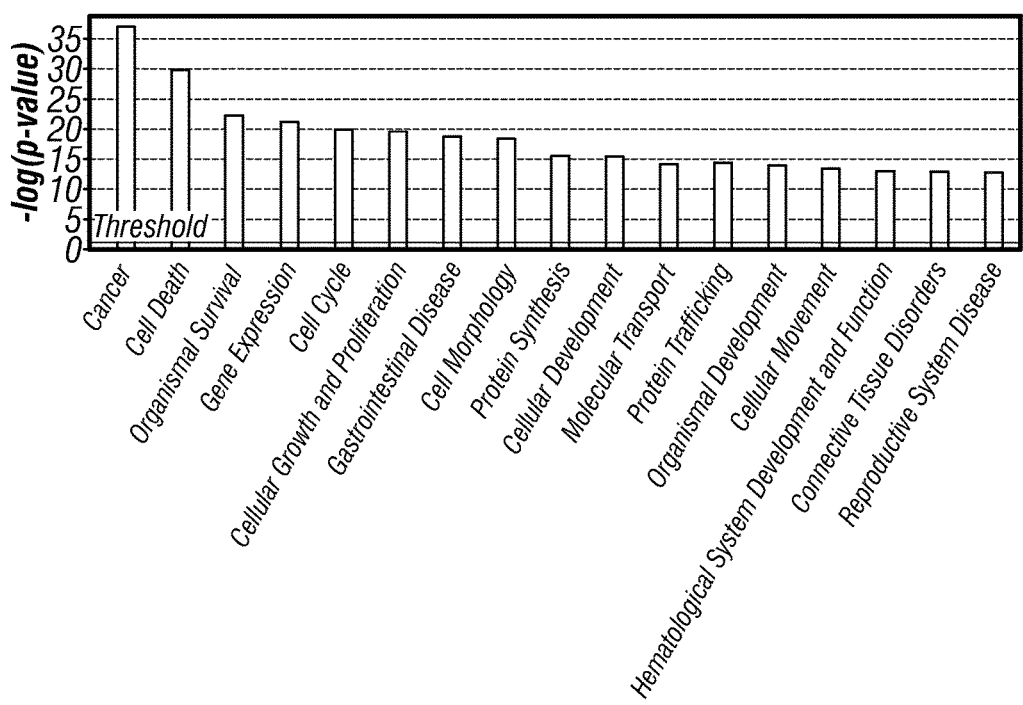
FIG. 5 shows the cellular functions of the regulated genes in the tumor sample from a patient with lung cancer.
Figure 5:
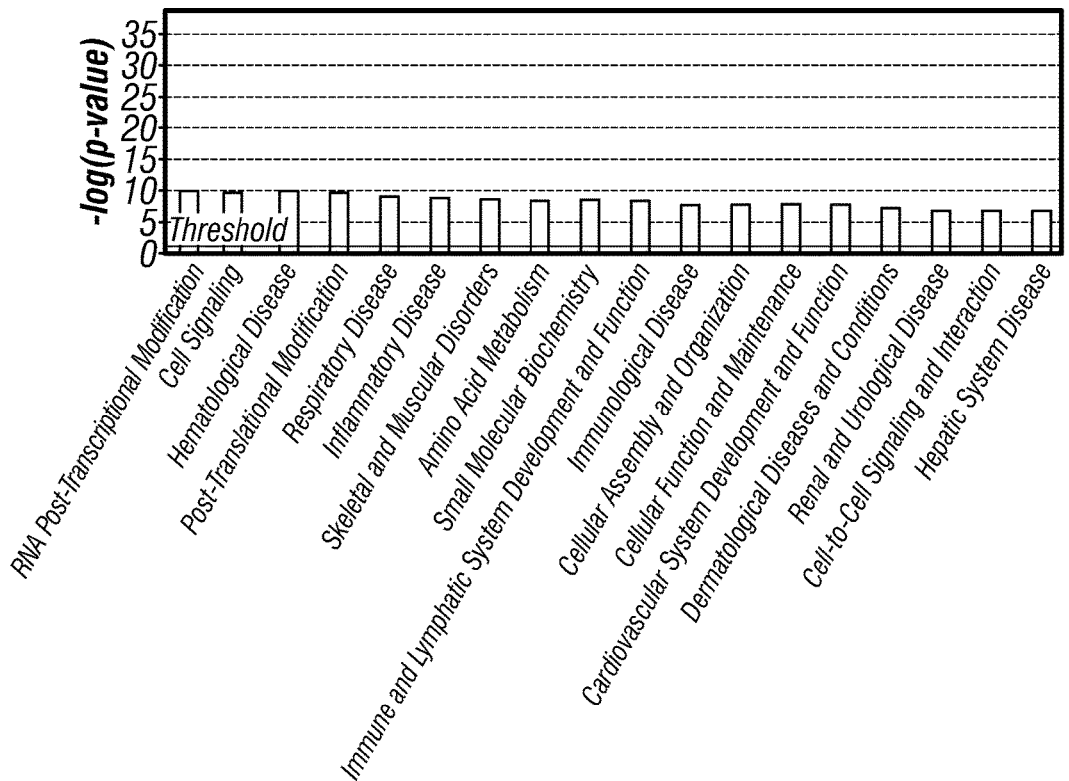

The differentially expressed genes were also scored for associated cellular functions. The highest scoring category was Cancer. (FIG. 5) Note also the high scoring of cell proliferative gene functions: Cell Cycle, Cellular Growth and Proliferation, Gene Expression.

Network analysis of the Affymetrix data revealed up-regulation of many components of the PDGF pathway. Most notably, the receptor PDGFRα and two of its ligands, PDGFα and PDGFC were over-expressed. Notably, several downstream effectors of PDGFα/PDGFRα, specifically, STAT3 and PI3K, are also up-regulated, indicating dysregulation of this signaling pathway that is implicated in carcinogenesis (Andrae, J., et al., *Genes & Dev.* (2008)

Figure 6:
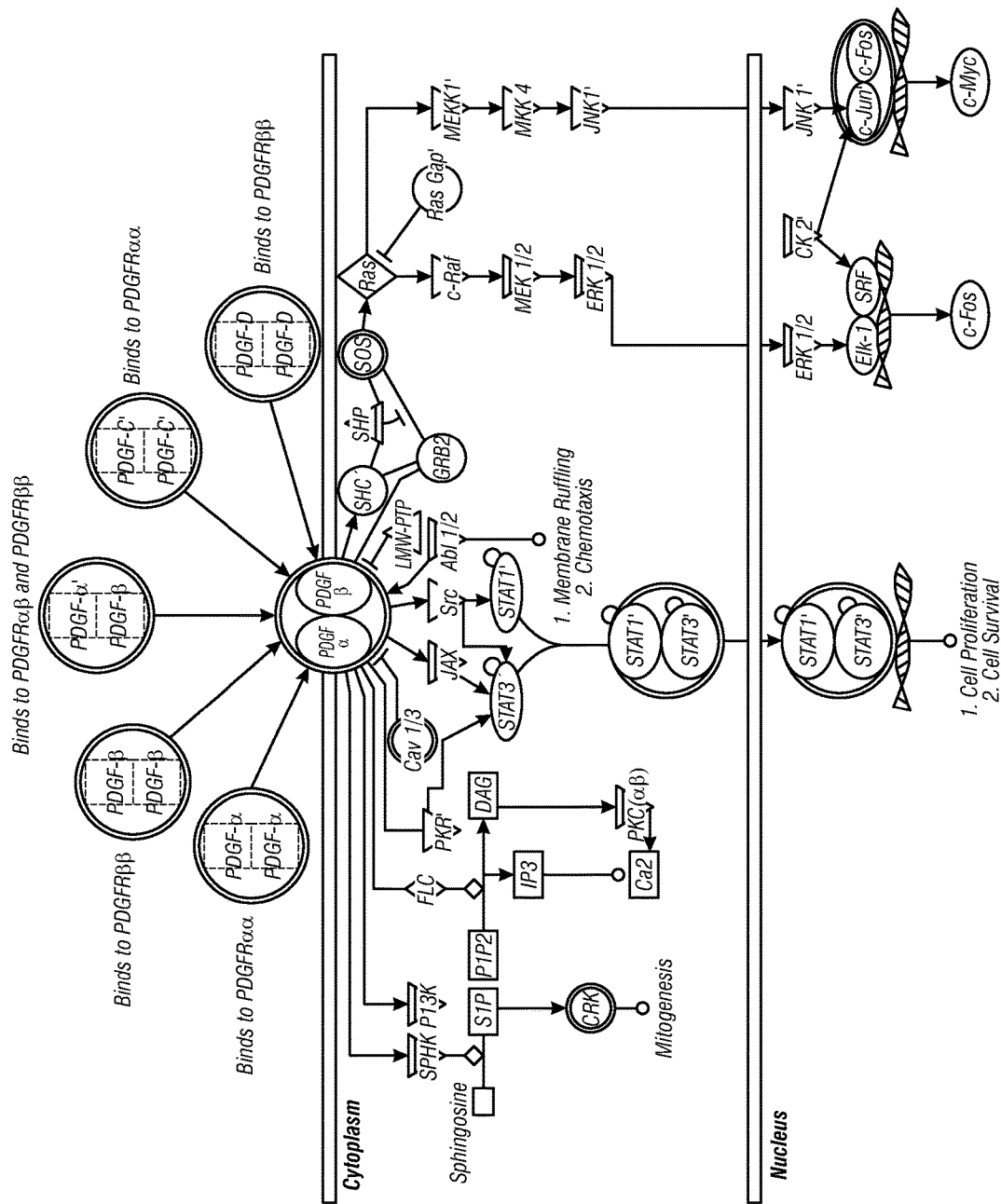
FIG. 6 is a diagram of the PDGF pathway known in the art but with superimposed gene expression data. The upper line represents the cell membrane and the lower horizontal line represents the barrier between the cytoplasm and the nucleus. The genes with darker shading are up-regulated and those with lighter shading are down-regulated in the tumor sample.

22:1276). Increased PDGF signaling has been observed in several neoplastic conditions (Dai, C., et al., *Genes & Dev.* (2001) 15:1913-1925; Smith, J. S., et al., *J. Neuropathol. Exp. Neurol.* (2000) 59:495-503; Arai, H., supra; Zhao, J., et al., *Genes Chromosomes Cancer* (2002) 34:48-57). This may represent an attractive intervention target, as inhibition of the tyrosine kinase activity could dampen downstream activity in the pathway and possibly lessen the stimulatory effects of the pathway on cell proliferation and survival. See FIG. 6.

The tyrosine kinase domain of PDGFRα is inhibited by imatinib (Gleevec®) and by sunitinib (Sutent®), which also targets VEGF. While the primary target of imatinib is the receptor tyrosine kinase c-ABL, it is also known to act at other targets including c-KIT and PDGFR (e.g., Wolf, D., et al., *Curr. Cancer Drug Targets* (2007) 7:251-258). Thus, regardless of the mutational status of c-KIT or c-ABL in this tumor, inhibition of PDGFRα may be considered by virtue of its potentially inhibitory effects on the up-regulated PDGF pathway.

Figure 7:
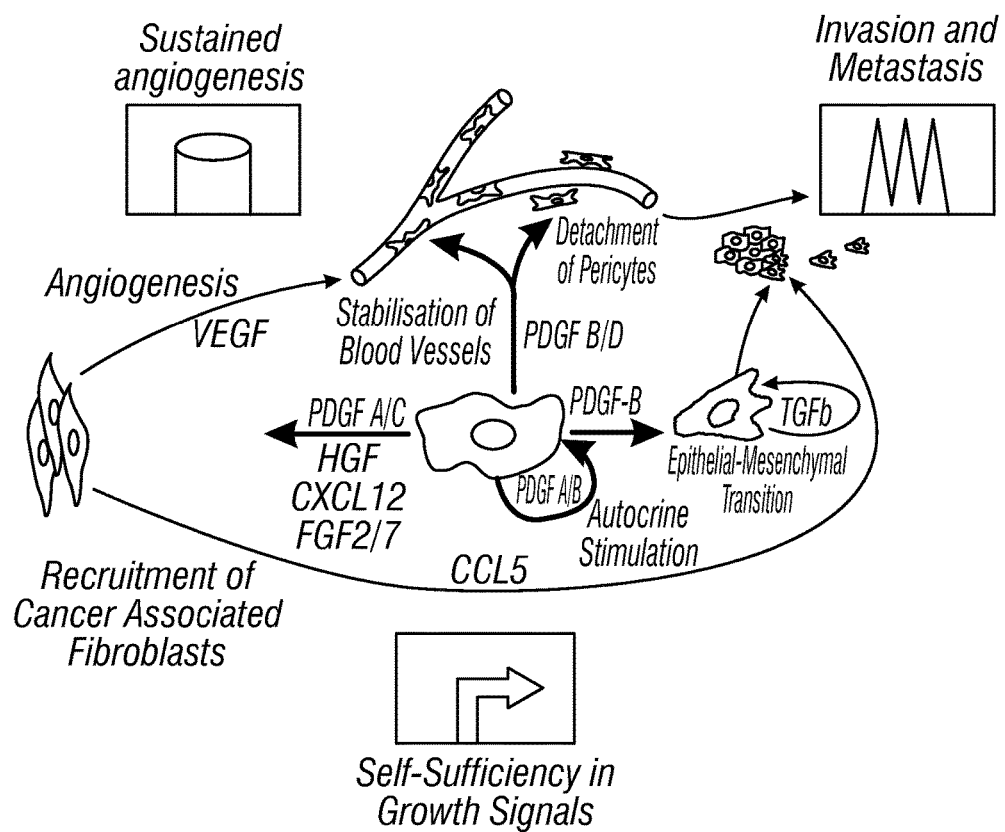
FIG. 7 is a diagram of the prior art knowledge of the role of PDGF pathways in tumor biology.

The potential cellular mechanisms by which the PDGF pathway may promote tumor growth are manifold. As shown in FIG. 7, below, PDGF may act directly on tumor cells in an autocrine or paracrine manner to enhance proliferation, or may act indirectly via recruited fibroblasts and pericytes to influence angiogenesis and/or invasion and metastasis. (Andrae, J., et al., *Genes & Dev.* (2008) 22:1276.)

Figure 8:
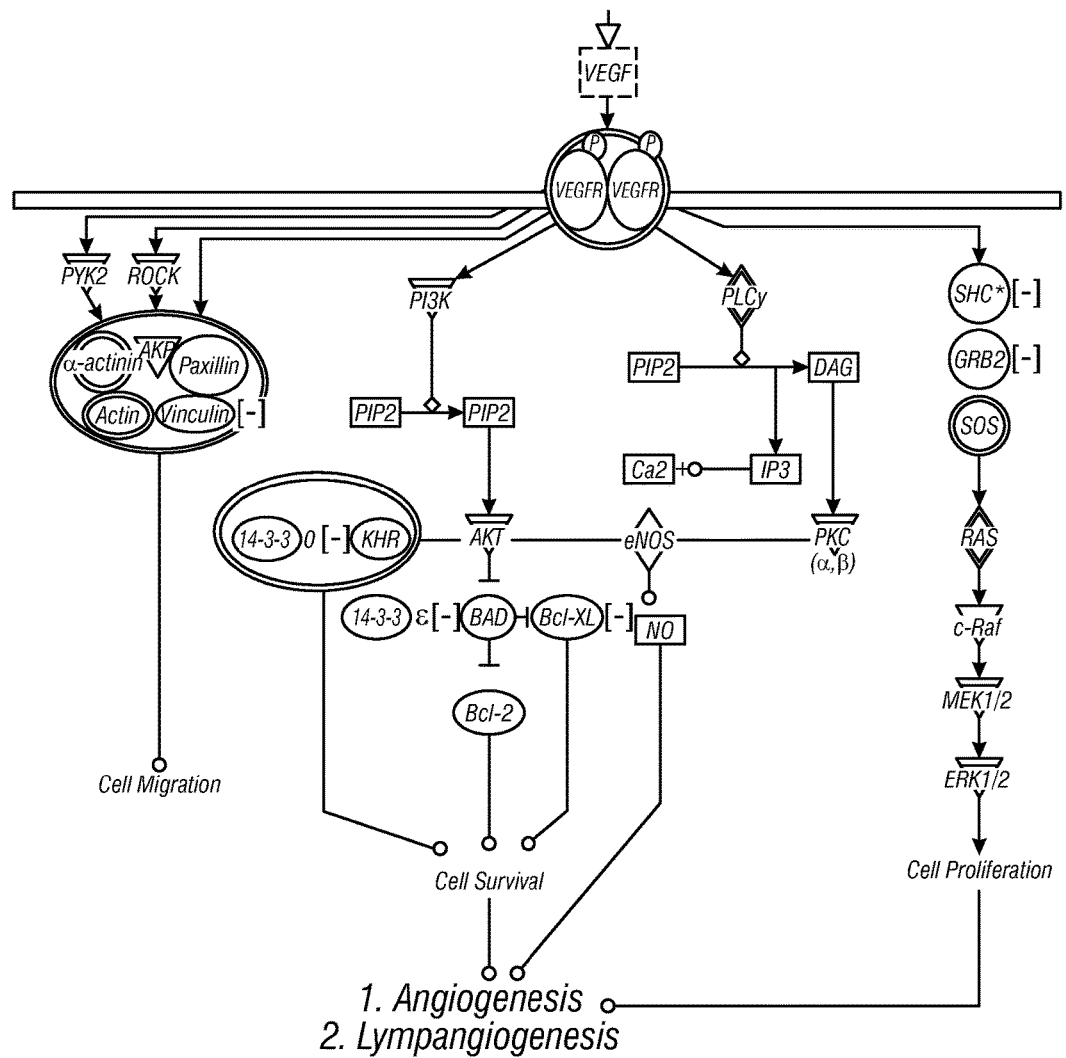
FIG. 8 is a diagram of what is known in the prior art of the VEGF pathway and its role in angiogenesis.

Also of note, VEGF was highly up-regulated (111-fold). To a lesser extent, its receptor and downstream effectors were up-regulated as well (FIG. 8). While this finding may have already been addressed by previous antiangiogenic therapy that is exhibiting response, it is significant to discuss here, as Sutent® has activity against VEGF in addition to inhibiting PDGFR. If weighing the relative merits of Gleevec® versus Sutent®, this may become relevant.

Our network analysis revealed that the PDGF pathway is strongly activated in the patient's samples, and has been shown in the literature to activate several mechanisms which directly and indirectly support tumor biology. Furthermore, there are FDA-approved therapies known to impact the PDGF pathway: imatinib (Gleevec®) and sunitinib (Sutent®).

Since there are negative data, algorithm 1b is applied to take account of two data points that are inconsistent with the hypothesis, the calculated probability of the pattern being produced only by chance ($\Pi$) is $4\times10^{-7}$.

In this case, the total pathway elements (q)=15, which are 4 ligands (PDGF α, β, C, and D); 2 receptors (PDGFR α, β; 2 receptor inhibitors (Oav 1/3, GRB 2); 5 intermediaries before STAT (PKR, JAK1, JAK2, JAK3, SRC); and 2 STATs (STAT1, STAT3).

The total aberrant genes consistent with hypothesis (n) is 10, which are 2 ligands (PDGF α and C); 1 receptor (PDGFR α); 5 intermediaries before STAT (PKR, JAK1, JAK2, JAK3, SRC); and 2 STATs (STAT1, STAT3). The total aberrant genes inconsistent with the hypothesis (n') is 2: 2 receptor inhibitors (Oav 1/3, GRB 2). The total number of possible pathways (N) is 283 canonical pathways in Ingenuity, the cut-off probability (p) is 0.05.

Then $\Pi_+=2\times10^{-10}$, $\Pi_-=0.2$ (these represent the "raw" probabilities of the hypothesis being false and the reverse hypothesis being false, respectively), leading to $\Pi'=1\times10^{-9}$ and further to $\Pi=4\times10^{-7}$ after the multiple pathway correction.

In algorithm 2b, inputting the specific p-values associated with the positive genes (ranging from 0.04 to $5\times10^{-4}$) and those for the negative genes (0.01 and $1\times10^{-4}$) leads to: $\Pi_+=2\times10^{-19}$, $\Pi_-=7\times10^{-5}$, $\Pi'=4\times10^{-15}$ and further to $\Pi=1\times10^{-12}$ after the multiple pathway correction that probability of pattern being produced by chance ($\Pi$) is $1\times10^{-12}$.

Using algorithm 3b, the privileged pathway elements (μ) is 6 which are 4 ligands, 2 receptors. The consistent aberrant privileged genes (τ) is 3, which are 2 ligands, 1 receptor. The inconsistent aberrant privileged genes (τ') is 0; non-privileged pathway elements (q) is 9; consistent aberrant non-privileged genes (n) is 7; and inconsistent aberrant non-privileged genes (n') is 2.

Inputting these values gives a probability of pattern being produced by chance ranges depending on the value of β from $6\times10^{-5}$ for β=1 to $1\times10^{-12}$ for β=0.

Our results showed that while EGFR was upregulated, there did not appear to be any activity in the rest of its pathways, so it was concluded that this upregulation was not clinically significant—i.e., that regardless of its upregulated state, it did not appear to be an important driver of malignancy in this tumor. It was then learned that the patient had been previously treated by Tarceva in response to a (positive) test for mutations in EGFR, and had shown no response on this therapy. Subsequent administration of Avastin as part of "trial and error" did show a partial response—Avastin targets VEGF. Our results indicated VEGF as a target.

As there are 6 aberrant genes inconsistent with the VEGF pathway, algorithm 1b is applied, and it yields a probability of pattern being produced by chance ($\Pi$) is $2\times10^{-10}$.

In this case, the total pathway elements (q) is 47, which are 2 ligands (VEGF A, B); 2 receptors (KDR, FLT-1, both in the VEGFR family); 12 PI3K members (Cα, Cβ, Cγ, Cδ, C2α, C2β, C2γ, C3, R1, R2, R3, R5); 2 PLCγ forms (PLCγ1, PLCγ2); 3 AKT forms (AKT1, AKT2, AKT3); 2 PKC forms (PKCα, PKCβ); 6 additional in survival branch (14-3-3σ, 14-3-3ε,FKHR, eNOS, BAD, Bcl XL, Bcl 2); 2 SOS forms (SOS 1, SOS2); 6 RAS forms (HRAS, KRAS, MRAS, NRAS, RRAS, RRAS2); 2 MEK forms (MEK1, MEK2); 5 ERK forms (MAPK1, MAPK3, MAPK6, MAPK7, MAPK12); and 3 additional in proliferative branch (SHC, GRB2, c-Raf).

The total aberrant genes consistent with hypothesis (n) is 20, which are 1 ligand (VEGF A); 1 receptor (KDR); 5 PI3K members (Cα, Cβ, C2α, C3, R1); 1 PLCγ form (PLCγ2); 3 AKT forms (AKT1, AKT2, AKT3); 1 PKC form (PKCα); 1 additional in survival branch (14-3-3ε); 1 SOS form (SOS1); 1 RAS form (KRAS); 1 MEK form (MEK1); 2 ERK forms (MAPK1, MAPK7); and 2 additional in proliferative branch (SHC, GRB2).

The total number of aberrant genes inconsistent with the hypothesis (n') is 6 which are 3 additional in survival branch (14-3-3σ, FKHR, Bcl XL); 1 SOS form (SOS2); 1 RAS form (RRAS2); and 1 MEK form (MEK2).

The total number of possible pathways (N) is 283 and the cut-off probability (p) is 0.05. Then $\Pi_+=2\times10^{-14}$, $\Pi_-=0.03$ (these represent the "raw" probabilities of the hypothesis being true and the reverse hypothesis being true, respectively), leading to $\Pi'=9\times10^{-13}$ and further to $\Pi=2\times10^{-10}$ after the multiple pathway correction.

Inputting the specific p-values associated with the positive genes (ranging from 0.04 to $1\times10^{-4}$) and those for the negative genes (ranging from 0.05 to 0.005) into algorithm 2b leads to: $\Pi_+=3\times10^{-33}$, $\Pi_-=5\times10^{-5}$, $\Pi'=7\times10^{-29}$ and further to $\Pi=2\times10^{-26}$ after the multiple pathway correction, giving a probability of pattern being produced by chance ($\Pi$) is $2\times10^{-26}$.

Applying algorithm 3b, the privileged pathway elements (μ) is 4, which are 2 ligands+2 receptors.

The consistent aberrant privileged genes (τ) is 2; inconsistent aberrant privileged genes (τ') is 0; non-privileged pathway elements (q) is 43; consistent aberrant non-privileged genes (n) is 18; and inconsistent aberrant privileged genes (n') is 6.

This provides a probability of the pattern being produced by chance, depending on the parameter β, ranging from $8 \times 10^{-6}$ for $\beta=1$ to $2 \times 10^{-26}$ for $\beta=0$.

TABLE 3

Regulated Networks from Lung Cancer Sample

| ID | Molecules in Network | Score | Focus Molecules | Top Functions |
|----|----------------------|-------|-----------------|---------------|
| 1 | ALCAM, ARL6IP5, ATP2A2, CANX, CAV1, CAV2, CD59, CEP170, CLINT1, CLTA, DOM3Z, EMP2, EPS8, FLOT1, FLOT2, GJA3, GNA11, HCCS, KPNB1, LIN7C, LRRFIP2, NGFRAP1, PCMT1, RBM4, SH3BGRL2, SLC1A1, SQRDL (includes EG: 58472), SVIL, TACSTD1, TCEB2, TENC1, TMOD3, WFS1, WSB1, XPNPEP3 | 25 | 35 | Cancer, Cellular Assembly and Organization, Cellular Function and Maintenance |
| 2 | ARHGAP18, ARMC8, BCL2L1, BECN1, BFAR, CLCN3, CLK1, CSPG5, DYNC1I2, DYNLRB1, DYNLT3, FGD2, FIP1L1, GANAB, GOPC, GRID1, HTRA2, LUC7L, MKLN1, MPHOSPH6, NKTR, RNPS1, SFRS2, SFRS4, SFRS6, SFRS8, SFRS11, SFRS2IP, SRPK1, SRPK2, STK17B, VDAC1, ZFP91, ZFR, ZRSR2 | 25 | 35 | RNA Post-Transcriptional Modification, Cellular Function and Maintenance, Embryonic Development |
| 3 | BTG3, CDK2, CDK2AP1, CIRBP, CNBP, CNOT1, CNOT2, CNOT3, CNOT6, CNOT7, CNOT8, CNOT6L, ERH, LATS1, LXN, MOBKL1B, MRPS14, PABPC1, PAIP1, PAN3, PINX1, PPM1A, PSMF1, PSPH, RBM7, RBMX, RNF126, RPL23A, RPL35A, RPS16, RPS28, RQCD1, STK38, TAGLN2, TBCA | 25 | 35 | Cancer, Cell Cycle, Skeletal and Muscular Disorders |
| 4 | ABCC4, ALG3, ASXL1, ASXL2, ASXL3, CDK10, CKS2 (includes EG: 1164), CNN3, CSRP1, CSTF3, DDX19A, DYNC1LI2, EBP, EIF4A2, EIF4G3, FAM134C, G0S2, GLTSCR2, HCN2, IDI1, IFRD1, MIF4GD, PDCD4, PHF19, PINK1, PMS2L3, PTEN, RNASEH1, RPL22, RPL39, RPS13 (includes EG: 6207), SEL1L, SHFM1 (includes EG: 7979), TRAM1, TRAPPC3 | 25 | 35 | Drug Metabolism, Molecular Transport, Nucleic Acid Metabolism |
| 5 | ATF7, C4ORF34, C6ORF203, CLNS1A, CSDE1, EBF1, FBXL11, FLJ20254, GEMIN7, GPRC5C, ITSN2, KCTD3, LSM1, LSM4, LSM5, LSM8, MAP2K1, NARS, OLA1, PCDH9, PLEKHA5, PPAP2B, PRIC285, PRMT5, SNRPD2, SNRPD3, SNRPE, SNRPG, SPTLC2 (includes EG: 9517), ST7, STRAP, TBL1XR1, THUMPD3, TRAF3IP3, ZNF706 | 25 | 35 | RNA Post-Transcriptional Modification, Cellular Development, Connective Tissue Development and Function |
| 6 | BRD2, BRP44, C11ORF61, C20ORF24, CIDEB, CRBN, DFFA, DMXL2, DPM1, EFTUD2, GCN1L1, HEATR1, KIAA0406, KIAA1967, MED1, MLSTD2, MRPL41, NUP54, NUP188, OPA1, PDXDC1, PRKD3, PTP4A3, RAB3GAP1, SATB1, SSR1, SSR3, STRN4, TMEM33, TMEM41B, TOMM22, TOMM70A, UBE4A, USMG5, ZNF294 | 25 | 35 | Cancer, Immunological Disease, Lipid Metabolism |
| 7 | ADNP, ARID2, ARID1A, ARID1B, ATG7, ATG10, ATG12, C19ORF2, C20ORF67, CCNK, CEP76, COL14A1, DHFR, DIDO1, EPB41L5, HELZ, HTATSF1, KCNRG, KIAA1279, MLLT10, PAICS, POLR2A, SF1, SF3A1, SF3A2, SF3B1, SF3B3, SMARCA2, SMARCB1, SMARCC1, SRGAP3, SUPT6H, TCERG1, WWP2, ZNF638 | 25 | 35 | Gene Expression, Cellular Assembly and Organization, Cellular Compromise |
| 8 | AFF4, AHCTF1, CCAR1, CDC2L6, CHD9, CROP, DDX50, DDX52, DIMT1L, EIF4A1, ELL2, GCOM1, IKZF5, KIAA1310, KPNA4, MED8, MED13, MED16, MED19, MED23, MED24, MED25, MED26, MED13L, MED7 (includes EG: 9443), NOP5/NOP58, POLR2J, POLR2K, PUM2, RBM39, RECQL, TARDBP, WDTC1, ZCCHC10, ZNF281 | 25 | 35 | Gene Expression, Cell Signaling, Cell Cycle |
| 9 | AFTPH, ALOX5, AP1G1, AP1S2, AP1S3, C11ORF31, C4ORF42, CFB, CPSF3L, CREG1, DALRD3, DERL1, ERLIN2, ETF1, FAM14A, GNPNAT1, HBB (includes EG: 3043), HBG2, HBZ, IGF2R, KITLG (includes EG: 4254), KLHL24, MID1IP1, PGLS, PLSCR1, PLSCR3, RANBP2, SECISBP2, SELT, SEPHS2, SPG7, TXNIP, VCP, YIPF3, ZNF207 | 25 | 35 | Hematological System Development and Function, Tissue Morphology, Cancer |

TABLE 3-continued

Regulated Networks from Lung Cancer Sample

| ID | Molecules in Network | Score | Focus Molecules | Top Functions |
|---|---|---|---|---|
| 10 | ANKRD36B, ASMTL, C11ORF58, C14ORF147, CCL11, CDIPT, DPY19L1, FABP5, FKBP3, FLJ11184, GLT8D3, JARID1B, KCTD12, KIAA0152, KLF10, LIMCH1, MCC, MT1X, MYH10, NKX3-2, NSMCE4A, OSM, PAX9, PPIA, PRDX3, PRDX6, PSD3, PSIP1, PUS7, RIPK2, RPL38 (includes EG: 6169), S100A8, SMC5, TDO2, TXNDC1 | 25 | 35 | Cellular Movement, Hematological System Development and Function, Immune Response |
| 11 | ADM, BAT2D1, BTN2A1, CALCRL, CCR1, CD209, CEL, CLIC2, COL12A1, CUGBP2, CYBB, EDNRA, GPR34, GTPBP1, HIGD1A, HOXA9, IRX3 (includes EG: 79191), ITGAM, LOC339047, LY86, MSI2, NAALAD2, NANOG, NAP1L4, NPIP, NSUN5C, OAZ1, OSBPL8, OTP, PHACTR2, RAB31, RAMP2, SIM1, SRP72, TNC | 25 | 35 | Cancer, Cell-To-Cell Signaling and Interaction, Skeletal and Muscular Disorders |
| 12 | ABCD3, API5, ASAH1, BCAP29, C1ORF142, COX4NB, DC2, FADS1, GMPPB, HMGB3, KCNH7, MAGED1, MLF2, MTHFD1L, NOVA1, PGRMC1, PJA2, PRC1, RAB23, RGS1, RPE, SFXN1, SFXN4, SRPRB, TOR1AIP2, TRIM37, TSC22D1, TSC22D4, TTC35, UBLCP1, UQCC, YY1, ZC3H7A, ZMYND10, ZNF580 | 25 | 35 | Genetic Disorder, Lipid Metabolism, Metabolic Disease |
| 13 | ATE1, Catalase, CBWD1, CMTM3, CNIH4, CSK, DUSP16, DUSP22, EFS, ILK, IMP3, ITGA9 (includes EG: 3680), KLF11, LIMS1, LPXN, MAPK1, METAP1, OTUD4, PARVA, PARVB, PHF21A, PTPN12, PTPN18, PTPN22, RGS5, RSU1, SCLT1, SEMA3F, SLC4A1, ST5, STYK1, TEX10, TGFB1I1, TPR, ZHX2 | 23 | 34 | Cell Morphology, Cellular Development, Amino Acid Metabolism |
| 14 | AIFM2, ANLN, ASPM, C14ORF106, DR4/5, EGFL6, FAM3C, GLIPR1, HMGN2, IKIP, JMJD1C, LETMD1, MBNL2, MORC3, MPV17L, MTDH, PPP4R2, PQLC3, PRODH (includes EG: 5625), RECQL4, RFFL, SCO2 (includes EG: 9997), SLC19A2, SMA4, SMG1, SNRK, STEAP3, TMED7, TMEM97, TP53, TPRKB, TULP4, UBL3, ZMAT3, ZNF84 | 23 | 34 | Cancer, Cell Cycle, Genetic Disorder |
| 15 | ATIC, ATYPICAL PROTEIN KINASE C, BHLHB2, BHLHB3, C17ORF42, CLN6, CMBL, COX5B, DVL3, ECT2, EME1, FFAR2, HNRPDL, IL29, IL10RB, IL13RA1, IL27RA, IL9R, KIF3A, KIF3B, LMO4, LMO1 (includes EG: 4004), MIRN21 (includes EG: 406991), PARD3, PARD6G, PITPNB, PRKCI, PTCRA, RAB2A, SOCS7, SPCS2, STAT3, STMN3, TMF1, ZNF148 | 23 | 34 | Cell Morphology, Nervous System Development and Function, Cancer |
| 16 | AKT1, COL4A2, FBLN1, HEYL, HIPK3, KLF15, LIMD1, MATR3, METTL1, MORC4, MTCP1, MTMR4, MUT, NDRG2, NEXN, NID1, PKC ALPHA/BETA, PLAC8, PLXDC1, POP4, PPHLN1, PPL, PSG3, RICTOR, RPP14, RPP25, SKIL, SVEP1, THAP5, TRIB2, TSC1, TSKU, TTF2, UBE4B, ZNF107 | 23 | 34 | RNA Post-Transcriptional Modification, Cell Signaling, Post-Translational Modification |
| 17 | ABI2, APBB1IP, ARF5, B4GALNT1, CCDC53, DGKA, DMN, ENAH, GART, GTF3A, GTF3C1, GTF3C2, HIF3A, HTATIP2, KIAA0368, NCOA5, NRP1, NRP2, OPTN, PCM1, PLXNA1, PLXND1, RAB11B, RAB11FIP3, RAB11FIP4, Sema3, SEMA3B, SEMA3C, SEMA6D, SNAI2, STC1, TBC1D8, TMSB10, VASH1, VEGFA | 23 | 34 | Cardiovascular System Development and Function, Embryonic Development, Organismal Development |
| 18 | AMOTL2, CASC3, DCP2, DCP1A, DCP1B, DDX6, DEK, EIF2C1, EIF2C2, EXOSC6, G3BP2, Hdac1/2, HIST1H3A, ING4, ITGB1BP1, KRIT1, MAGOHB, PDS5A, RAD21, RBM8A, RELA, SKIV2L2, SMC3, SMC1A, SRRM1, SRRM2, STAG1, STAG2, SYCP3, UPF2, UPF3A, UPF3B, WAPAL, XRN1, ZDHHC8 | 23 | 34 | RNA Damage and Repair, Viral Function, Cell Cycle |
| 19 | CHI3L1, COL16A1, COMMD1, COMMD2, COMMD3, COMMD10, DAB2, ELF1, ELF2, ELF4, ELK3, ETS, ETS2, FLT1, HIVEP2, IPO8, KARS, KPNA1, KPNA3, LMO2, LSM12, NFKB1, NFKBIL2, NNMT, NUP50, RIPK5, SLC25A6, SLC39A14, SRP19, SRP54, TRIM3, TRIP4, TUBB6, UBA3, UBE2K | 23 | 34 | Gene Expression, Cellular Development, Hematological System Development and Function |

TABLE 3-continued

Regulated Networks from Lung Cancer Sample

| ID | Molecules in Network | Score | Focus Molecules | Top Functions |
|----|---------------------|-------|-----------------|---------------|
| 20 | AMACR, ARL15, C16ORF14, CCDC90B, DBI, EIF1AD, FAM101B, FAM123A, FUNDC2 (includes EG: 65991), LAMA4, NACA, PCTK1, PEX3, PEX5, PEX10, PEX13, PEX14, PEX19, PEX26, PEX11B, PMP22, RBM17, RNF135, SAT1, SCP2, SERPINB9, SLC25A17, Soat, SOAT1, STAT1, TFG, TNFRSF10C, TNRC6A, UBR1, ZHX1 | 23 | 34 | Genetic Disorder, Metabolic Disease, Cellular Assembly and Organization |
| 21 | AZIN1, BDP1, BNC2, BRD8, C20ORF20, CDK4-Cyclin D2, EAF1, EID1, EP400, EPC1, EPC2, FLJ20309, GMPS, H1F0, ING3, INOC1, JARID1A, LACTB, LIN37, MAGEF1, MORF4L1, MORF4L2, MRFAP1, OAZ2, PHF12, PLSCR4, RB1, RBBP6 (includes EG: 5930), REEP5, RSL1D1, RUVBL2, SRPR, THOC1, THOC2, TRIM27 | 23 | 34 | Small Molecule Biochemistry, Cancer, Skeletal and Muscular Disorders |
| 22 | Ahr-aryl hydrocarbon-Arnt-Esr1, ATN1, BICC1, C9ORF86, COL15A1, CSNK1G2, CUEDC2, CXORF45, DAZ4, DECR1, DNTTIP2, DZIP1, EFEMP1, ESR1, FAM103A1, GFI1B, HAT1, HYPK, KIAA0182, LCOR, LENG8, MYST3, NELL1, PNRC2 (includes EG: 55629), QKI (includes EG: 9444), RBM9, RBPMS, RCHY1, RERE, RNF138, SLC39A8, SLIT1, TM4SF1, TRIM16, TRIM22 | 23 | 34 | DNA Replication, Recombination, and Repair, Cellular Development, Cellular Growth and Proliferation |
| 23 | ASCL2, BCLAF1, C16ORF53, CCDC123, CDC42EP3, CEBPB, CPB2, DPY30, GMCL1, Histone-lysine N-methyltransferase, LEMD3, MAP4, MLL2, MLL3, NCOA6, NFKBIZ, NSD1, PRPF3, PSPC1, RAB10, RBM14, SART3, SEPT2, SEPT6, SEPT7, SEPT8, SEPT9, SEPT11, SETD7, TFDP2, TMEM176A, TPT1 (includes EG: 7178), TUBB, UTX, WHSC1L1 | 23 | 34 | Cellular Assembly and Organization, Cellular Compromise, Protein Synthesis |
| 24 | AKAP2, BTF3 (includes EG: 689), C9ORF80, CCL18, CREBL2, ECM2, EMR2, EXT1, EXT2, FBXO9, FOXN3, HIG2, HYOU1, IRS1, KIAA0999, KLF12, LYK5, MARK3, MARK4, MRPS10, MRPS15, NOL11, NUAK1, PMPCB, PRKRA, PRPS1, PRPSAP1, PRPSAP2, Ribose-phosphate diphosphokinase, RPS29, SAAL1, SNF1LK2, SPARCL1, STK11, TUBE1 | 23 | 34 | Cancer, Genetic Disorder, Nucleic Acid Metabolism |
| 25 | ATXN3, CDC25B, CHD4, CLOCK, CREBBP, CRY1, CUX1, ERG, ETV1, EYA3, FOXM1, H3F3A, H3F3B, HMGN1, MAP3K7IP3, MBD1, NAPSA, NCOA1, NCOA2, NCOA3, NKX2-1, NPAS2, Pias, PIAS1, PIAS2, PIAS3, PLAGL1, RBCK1, SFTPB, SMARCE1, TACC2, TAGLN, TBX19, TP53BP2, TROVE2 | 23 | 34 | Gene Expression, Reproductive System Development and Function, Cell Morphology |
| 26 | ABCA1, ACTC1, ACTG1, CADPS2, CDC2L5, CENPF, DGKZ, DMD, DSTN, DTNB, EGLN1, EIF4B, ELP2, GAK, IFN ALPHA RECEPTOR, IL6ST, JAK2, MAPK8IP3, MEP1B, MTIF2, NCAPG (includes EG: 64151), NPM1 (includes EG: 4869), OS-9, OSMR, PDLIM5, PTPRK, RASGRP1, SBDS, SCN4A, SNTB2, SOCS5, SYNE2, TMSB4Y, UBASH3B, UTRN | 23 | 34 | Developmental Disorder, Genetic Disorder, Skeletal and Muscular Disorders |
| 27 | ANKRD44, DDX56, DUB, HECW1, MARCH7, MED20, UCHL1, UCHL3, UCHL5, USP1, USP3, USP4, USP6, USP7, USP10, USP12, USP14, USP15, USP18, USP28, USP31, USP32, USP33, USP34, USP37, USP42, USP45, USP46, USP47, USP48, USP53, USP54, USP9X, USP9Y, ZNF423 | 23 | 34 | Post-Translational Modification, Behavior, Cellular Function and Maintenance |
| 28 | ABHD2, AGR2, ARL4C, ARRDC3, ATP1A3, ATP1B3, ATP1B4, C19ORF12, CCNE2 (includes EG: 9134), CDH11, CLEC2B, CTSH, CUTC, DYNC1H1, FGF14, FXYD2, GMNN, HNRPUL1, HPGD, KCNJ2, LGALS3, MFGE8, MGC16121, Na-k-atpase, NADSYN1, PBRM1, PDLIM3, PGM2L1, PLEK2, PRICKLE1, REST, S100A2, SCHIP1, SMARCA4, TBX2 | 23 | 34 | Molecular Transport, Cancer, Cell Death |
| 29 | ANAPC5, BAT1, DICER1, DNA-directed RNA polymerase, DNM2, EXOC4, HNRPLL, HNRPM, HSPC152, MED31, MGC13098, MSH6, NCAPH2, NOLC1, NONO, ORAI2 (includes EG: 80228), PNN, POLR1D, POLR2C, POLR3C, POLR3F, POLR3H, PPIG, PRPF4B, PTBP1, RAVER2, RBM4B, RPL37, SFRS3, SFRS18, SMC4, SSB, STC2, TMPO, ZCCHC17 | 23 | 34 | RNA Post-Transcriptional Modification, Gene Expression, Organ Morphology |

TABLE 3-continued

Regulated Networks from Lung Cancer Sample

| ID | Molecules in Network | Score | Focus Molecules | Top Functions |
|---|---|---|---|---|
| 30 | ARIH1, BAG4, C11ORF9, CHORDC1, CKAP4, CTNNA1, DNAJB11, DOK3, EIF4E2, FANCC, FHL2, HEPH, HFE, HNRPK, HSP90AA1, HSPA8, HSPA1A, HSPA1B, IFI44L, JINK1/2, LRRC59, PHLDA1, PSPN, RET, RNF19A, S100A11 (includes EG: 6282), SFN, ST13, SYPL1, TBC1D9, TFRC, TXN, XPOT, YWHAE, YWHAQ (includes EG: 10971) | 23 | 34 | Post-Translational Modification, Protein Folding, Cancer |
| 31 | ATXN1, C14ORF139, C1ORF65, C20ORF77, C6ORF199, CADPS, CALCOCO2, DBNDD2, DZIP3, FAS, FBF1, FBXL18, FLJ10404, GABARAPL2, GBAS, LRSAM1, LUC7L2, METT11D1, MGAT4B, MTERFD2, NASP, NOL3, PEA15, PHPT1, PUM1, R3HDM1, SFRS14, SGMS1, SSFA2, TBC1D5, TNFR/Fas, TTC19, TUBGCP2, TUBGCP4, UBAP2L | 23 | 34 | Lipid Metabolism, Small Molecule Biochemistry, Molecular Transport |
| 32 | ARL5B, C12ORF35, C16ORF57, CAMTA1, CCDC59, CROT, CTSB, DEDD, EEF1A1, GFM1, GPNMB, HSPE1, KIAA1712, KIF1B, NUDT3, PAPSS1, PAPSS2, PHYH, Protein-synthesizing GTPase, PRSS1 (includes EG: 5644), RAB2B, RANBP3, RNF167, RPLP1, RSRC1, S100A10, SCN11A, SCN5A, SLC25A13, SMAD4, SOX30, THRAP3, TMPRSS3, TRIM33, WARS | 23 | 34 | Cancer, Cell Cycle, Tissue Morphology |
| 33 | CAPZA1, CAPZB, CCBL2, CCNA2, CDS2, CGGBP1, Cyclin A, EMX2OS (includes EG: 196047), FAM19A2, FAM49B, FLCN, FMR1, FXR1, HIST1H2BC, KLHL3 (includes EG: 26249), METTL9, MLL5, MSRA, MTPN, NAALADL2, NFYB, NPTX2, PITPNM2, RABIF, RIMBP2, SLC25A28, SLMAP, ST8SIA1, TBC1D22A, TM7SF3, TMEM87A, TTC3, VPS52, ZMPSTE24, ZMYM3 | 23 | 34 | Dermatological Diseases and Conditions, Genetic Disorder, Nervous System Development and Function |
| 34 | ADAMTS9, AIM2, B3GNT5, BEX1 (includes EG: 55859), CARD14, CBR3, CD14/TLR4/LY96, CHM, CXCL16, ECOP, FNTA, FNTB, HDGF, IRAK1BP1, LY96, MFHAS1, NFkB, NKIRAS1 (includes EG: 28512), NOL14, PAK1IP1, PNKD, PTP4A2, RAB7A, RABGGTB, RAP2A, RASSF4, RNF19B, SLC11A2, STK10, SUMO1, TNFAIP8, TNFSF18, TRIM69, UNC5CL, WTAP | 21 | 33 | Amino Acid Metabolism, Post-Translational Modification, Small Molecule Biochemistry |
| 35 | Akt, AKTIP, ARMCX3, ARS2, ASAH2, BRD7, C11ORF79, C1ORF103, C1ORF174, CEACAM6 (includes EG: 4680), DEXI, EIF3J, FKHR, GOLM1, IMMT, KBTBD7, KIAA1377, MAL2, MCAM, MRPL44, NIPSNAP3A, PCTK2, PHIP, PPT1, RER1, RPL13A, SEC14L2, SLC40A1, SOCS4, TACC1, TPD52, TPD52L1, TXNDC9, UXS1, ZFAND3 | 21 | 33 | Lipid Metabolism, Small Molecule Biochemistry, Post-Translational Modification |
| 36 | ADI1, ANP32A, ANP32B, APEX1, CDKN1A, DDX17, DLG5, DSE, ELAVL1, ERO1L, FBXO38, FEN1, Foxo, HMGB2, HNRNPA2B1, KIAA0101, KIF20A, KLF7, KPNA6, NPAT, Oxidoreductase, SEPW1, SET, SETBP1, SFPQ, SFRS1, SFRS12, SLC30A5, SNRPA1, TOPORS, TTLL5, VEZT, VGLL4, WHSC2, WWOX | 21 | 33 | RNA Post-Transcriptional Modification, DNA Replication, Recombination, and Repair, Gene Expression |
| 37 | AP1GBP1, APBB2, BICD2, BZW1, BZW2, DEGS1, EDEM1, EGFR, Egfr dimer, EML4, GAS5, KDELR1, KDELR2, LRRFIP1, MAN2B1, Mannosidase Alpha, MTM1, MTMR2, MTMR12, NEK6, NEK7, NEK9, RPS25, RUSC1, SBF2, SCAMP1, SCAMP2, SERINC3, SGSM2, SH3BGRL, SLC16A1, SNX13, SURF4, TNXB, VDAC3 | 21 | 33 | Lipid Metabolism, Small Molecule Biochemistry, Cancer |
| 38 | ACTR1A, ANKHD1, ATP7B, BICD1, C14ORF166, CDC42SE1, CEP63, CHML, CLASP2, CLIP1, CRK/CRKL, DCTN2, DCTN4, DIAPH3, DISC1, DST, Dynein, ERN1 (includes EG: 2081), EXOC1, GLRX, MAPK8, MAPRE1, MDFIC, NDEL1, NIN, PAFAH1B1, RAB6A, RAB6IP1, RABGAP1, SH3BP5, SPAG9, SPTBN1, TAOK1, TEGT, TRAF3IP1 | 21 | 33 | Cell Cycle, Embryonic Development, Hair and Skin Development and Function |
| 39 | APTX, BACE1, Beta Secretase, BTBD14B, CALCOCO1, CCND1, CDK2-Cyclin D1, CHMP4A, COL4A3BP, CUL3, GGA2, GPBP1L1, GTPBP4, H2AFY, MAT2B, PAPOLA, PLEKHF2, PRR13, PTPN9, RB1CC1, RTN3, RTN4, SP2, SPEF1, SPG21, SPOP, STXBP1, SYT17, TSPYL2, UBE2Z, VAPA, XRCC4, ZEB2, ZFHX3, ZNF639 | 21 | 33 | Cancer, Dermatological Diseases and Conditions, Gene Expression |

TABLE 3-continued

Regulated Networks from Lung Cancer Sample

| ID | Molecules in Network | Score | Focus Molecules | Top Functions |
|---|---|---|---|---|
| 40 | Ap1, AP3B1, AP3D1, AP3M1, AP3S1, ARF1, BET1, BLVRA, CD58, EEA1, GOSR1, GOSR2, MARCH2, PACS1, SCARB2, SCFD1, SEC22A, SEC22B, SEC23A, SEC23IP, SEC24A, SEC24B, SEC24C, SNAP23, Snare, STX6, STX7, STX16, USO1, VAMP3, VAMP4, VAMP7, VPS11, VPS41, VPS45 | 21 | 33 | Cellular Assembly and Organization, Molecular Transport, Protein Trafficking |
| 41 | ASPN, COL11A2, COL1A2, COL3A1, DLGAP4, EPB41L1, FBLIM1, FERMT2, FN1, FYB, HTRA1, IGBP1, Integrin&alpha, Integrin&beta, ITGAE, ITGAV, ITGB5, ITGB6, LTBP1, LTBP2, LTBP3, MGP, MICAL2, MID1, MYO10, PPP6C, SAPS2, SEC23B, SEC24D, SPARC, ST6GAL1, TGFB2, TGFB3, TGFBI, TSPAN13 | 21 | 33 | Cellular Movement, Reproductive System Development and Function, Cell-To-Cell Signaling and Interaction |
| 42 | BAT3, CD99 (includes EG: 4267), COL8A1, CPSF6, E3 HECT, EFEMP2, EPDR1, ERP27, FAM127B, FMNL3, GIGYF2, HRASLS3, HUWE1, KLHDC5, KLHL12, NFKBIA, NOTCH2NL, PCDH17, PRPF40A, RAD23A, RIC8A, RPN1, RSRC2, SNRPN, STCH, STIM2, TNRC6B, UBA6, Ube3, UBE3A, UBE3B, UBQLN1, UBQLN2, UBQLN4, ZCCHC8 | 21 | 33 | Cardiovascular Disease, Cardiovascular System Development and Function, Hematological Disease |
| 43 | ADAD1, ADAR, ADARB1, ADD3, Adenosine deaminase, AKR7A2, BRAP, CCDC92 (includes EG: 80212), CCNL1, CELSR2, DCBLD2, FHL1, FXC1, GSS, KLF6, LMAN1, MCFD2, MT1E, NFAT5, OMD, PDGF BB, PHF10, PLEKHA1, RPL13, SLC6A6, SLC7A1, TIMM10, TIMM13, TIMM23, TIMM44, TIMM17A (includes EG: 10440), TIMM8A, TIMM8B, TRIOBP, ZFP36L1 | 21 | 33 | Genetic Disorder, Hematological Disease, Protein Trafficking |
| 44 | DDIT4, DDX5, DNASE1L3, ELMOD2, Esr1-Esr1-estrogen-estrogen, FAM130A1, GLCCI1, H1FOO, HNRPD, HSD17B12, ILF3, JMJD6, KHSRP, MED14, MTL5, NR3C1, PHLDA2, POGK, POLDIP2, POLR2B, PRKDC, PTMS, RNF10, RNF14, RPL34, SELENBP1, TADA2L, TIA1, TIAL1, TNFAIP1, TPST2, TRAP/Media, UNC45A, WDR37, WDR40B | 21 | 33 | Molecular Transport, Cancer, Cell Death |
| 45 | ACBD3, APPL2, AUP1, C1ORF124, C4ORF16, CDC40, CHMP1A, DAZAP2 (includes EG: 9802), DCUN1D1, EPPK1, EPS15, GAD, GGA1, GRB2, HGS, HRBL, LAPTM5, MIST, NISCH, PHKA2, RAB22A, RNF11, SHIP, SIGLEC7, SKAP2, SMURF2, STAM, STAM2, STAMBP, UNC5C, USP8, USP6NL, VPS24, VPS37C, ZFYVE9 | 21 | 33 | Cellular Function and Maintenance, Molecular Transport, Protein Trafficking |
| 46 | Adenosine-tetraphosphatase, AGRN, ANGPTL2, ARL8B, ATP5C1, ATP5D, ATP5F1, ATP5I, ATP5J, ATP5J2, ATP5L, ATP5O, ATP6V0A2, ATP6V0C, ATP6V0D1, ATP6V0D2, ATP6V0E1, ATP6V1A, ATP6V1C1, ATP6V1E1, CARS, CHMP2B, CPD, CREB1, ETV6, H+-transporting two-sector ATPase, ITIH2, ITIH4, LASS2, OPA3, PNO1, SLC18A2, SLC2A3, TCIRG1, ZNF337 | 21 | 33 | Molecular Transport, Cell-To-Cell Signaling and Interaction, Cellular Assembly and Organization |
| 47 | CAPRIN1, CCDC50, DHX9, EIF3A, EIF3B, EIF3C, EIF3E, EIF3H, Fcer1a-Fcer1g-Ms4a2, Fcgr2, FCGR2C, FYN, G3BP1, HNRNPU, HSPH1, IARS2, LUM, MDH1, NANS, PARN, RILPL2, RNMT, RPL6, RPL7, RPL10, RPL14, RPS2, RPS6, RPS3A, RPS4X, SFRS10, SON, STAU1, TUBB3, YTHDC1 | 21 | 33 | Protein Synthesis, Carbohydrate Metabolism, Small Molecule Biochemistry |
| 48 | ADH4, ADH5, ADH6, alcohol dehydrogenase, ALDH2, AQP1, DHRS2 (includes EG: 10202), EIF5A, FBXO33, IPO7, IPO9, MT1G, NR2F1, NR2F2, NUP98, NUP153, NUTF2, PAIP2, PURA, PURB, RAN, RANBP5, RPL5, RPL19, RPS7, SP3, SP4, TEAD1, TNPO1, Vegf, XPO7, YBX1, ZBTB7A, ZFPM2, ZNF197 | 21 | 33 | Molecular Transport, Protein Trafficking, Small Molecule Biochemistry |
| 49 | AZI2, CCDC47, CMTM6, COMT, COX11, COX4I1, COX4I2, COX5A, COX6A1, COX7A2, COX7B, COX7C, COX8A, Cytochrome c oxidase, DARS, GABPB2, IARS (includes EG: 3376), Isoleucine-tRNA ligase, JTV1, JUNB, KIAA0090, LARS, LITAF, LMO3, MARS (includes EG: 4141), MFN1, MTX1, NAP1L1, OXTR, RAB3GAP2, SCYE1, SGPL1, TANK, TMBIM4, TMCO1 | 21 | 33 | Gene Expression, Behavior, Cell Signaling |

TABLE 3-continued

Regulated Networks from Lung Cancer Sample

| ID | Molecules in Network | Score | Focus Molecules | Top Functions |
|---|---|---|---|---|
| 50 | AHCYL1, BCL6, BCL2L11, BCOR, BNC1, C1ORF19, CD79B, Cpsf, CPSF2, CPSF3, EMCN, FLJ12529, FOXP3, GALNAC4S-6ST, GP1BA, GSR, IGHM, IGJ, IGL@, Igm, ITPR2, LAGE3, LYN, NUDT21, OSGEP, PCF11, PIGR, PRDM1, SAMSN1, SDC1, SUMO3, SYMPK, TNFSF13, TNFSF13B, TSN | 21 | 33 | Cell Cycle, Cellular Development, Hematological System Development and Function |
| 51 | ARF6, ARMET, C15ORF29, C6ORF211, CA12, CA13, Carbonic anhydrase, CNDP2, DAP3, DDOST (includes EG: 1650), DMXL1, Dolichyl-diphosphooligosaccharide-protein glycotransferase, EPAS1, GBE1, GLS, GSPT1, HIF1A, MAGT1, MAOA, NDRG1, PCBP3, PDK1, PKIB, PLOD2, PTPRG, RAB20, RGS10, RORC, RPN2, RPS9, RPS26, SAP18, SHMT2, STT3B, TPP2 | 21 | 33 | Cell-To-Cell Signaling and Interaction, Embryonic Development, Gene Expression |
| 52 | ARMC7, BPTF, CDK4, CDK4/6, Ctbp, CTBP1, DDX3X, DNAJA2, HCFC1, HDAC2, HNRNPA1, HNRPH1, IFIT3, IKZF1, IKZF2, KCTD13, KPNA2, LPCAT1, MBD2, MLL, NBR1, OGT, PML, PTMA, RBBP4, RBBP7, RNF12, SAP30, SIN3A, SIN3B, SMARCA1, UTP18, VTA1, ZC3HAV1, ZMYND19 | 21 | 33 | Cell Cycle, Cellular Assembly and Organization, DNA Replication, Recombination, and Repair |
| 53 | 14-3-3(&beta, &gamma, &theta, &eta, ζ), ARHGAP21, C16ORF80, C22ORF9, CAMSAP1L1, CCNY, DOCK11, EHD1, EPB41L2, FRY, FRYL, GAPVD1, HECTD1, ITGB3, KIAA1598, LAPTM4A, LNX2, NUMB, OSBPL3, PHLDB2, PPFIBP1, PRPF38B, RACGAP1, RASAL2, RASSF8, SAPS3, SDHA, SDHAL1, SDHC, SMCR7L, Succinate dehydrogenase, SYNPO2, TBC1D1, YWHAB, YWHAG | 21 | 33 | Cancer, Genetic Disorder, Cell Cycle |
| 54 | C14ORF129, CD44, CDC42, CDK5RAP2, DDX58, DEF6, DKC1, DMP1, EEF1G, EPB41L3, FCGR2A, GDI1, GDI2, HNRPH3, IQGAP, IQGAP3, IQGAP1 (includes EG: 8826), LOC196549, NOLA1, OAT, PECAM1, PKN2, PRMT2, Pseudouridylate synthase, PTPRA, PTPRE, PTPRM, PTPRS, RAB4A, RAB5A, RABEP2, RPUSD4, SMYD2, STARD9, TRIM25 | 21 | 33 | Immune Response, Immune and Lymphatic System Development and Function, Cellular Assembly and Organization |
| 55 | AFG3L2, ATP11B, ATPase, CCNH, CCNT2, CHD1, CRKRS, DHX15, EBAG9, FOXC1, GTF2H1, GTF2H2, HINT1 (includes EG: 3094), KIAA1128, OFD1, PBX3, PRUNE, PSMC2, PSMC4, PSMD1, PSMD5, PSMD7, PSMD9, PSMD10, PSMD12, PSMD13, RNA polymerase II, RNF40, RSF1, SAFB, SETD2, SMYD3, SUB1, TCEA1, ZNF451 | 21 | 33 | Gene Expression, Cell-To-Cell Signaling and Interaction, Cellular Development |
| 56 | ABCC5, Actin, ARPP-19, BDH1, CAP1, ENC1, FXYD3, GAS1, GLRX5, GPC5, GSN, HNRNPC, IPP, JUN/JUNB/JUND, KIAA1274, KRAS, LIMA1, MAPRE2, MLPH, MMD, MSLN, MTRR, PFDN4, PHACTR1, RAB27A, RASGRF2, RBM41, SEC11C, SERBP1, SYTL4, TES, TPM2, TPM3, TPM4, VBP1 | 21 | 33 | Cellular Assembly and Organization, Hair and Skin Development and Function, Cellular Function and Maintenance |
| 57 | ABCC6, Alpha Actinin, ANXA1, ANXA2, ARHGAP17, BLID, Calpain, CAPN2, CAPN3, CAPN7, CAPN8, CASP9, CREBZF, DDX46, EZR, KIAA0746, LAP3, MGC29506, MRPL42 (includes EG: 28977), PCYT1A, PTPN1, RBM5, RPL17, RPL23, RPL31, RPL27A, RPS21, RPS24 (includes EG: 6229), SCYL3, SORBS2, STOM, TLN1, TTN, VAT1, VCL | 21 | 33 | Cellular Assembly and Organization, Cell Signaling, Skeletal and Muscular System Development and Function |
| 58 | 14-3-3, APC, APCDD1, BUB3, CRIPT, CRKL, DLG3, DR1, EHF, EMP1, GAB2, GAB1 (includes EG: 2549), HCFC1R1, HDLBP, KAL1 (includes EG: 3730), LPHN1, MACF1, MDM4, MDM2 (includes EG: 4193), MED28, MET, NF2, RAB40C, RAPGEF1, SLC7A11, SPSB3, STAT5a/b, SULF1, TFEB, TFEC, TMEM22, TP63, WT1, ZEB1, ZNF224 | 21 | 33 | Cancer, Cell Cycle, Respiratory Disease |
| 59 | ARID5B, ASCC3, CHD2, CXCL10, DHX30, DYNLL1, FAM120C, FAM98A, GPRIN3, HDAC3, HMGB1 (includes EG: 3146), HNRPA3, MECP2, MTA1, MTR, NCOR2, NCoR/SMRT corepressor, NUFIP2, PPP4R1, RARB, RBAK, RREB1, RSBN1, SENP6, SERPINB1, SMC6, SUMO1, TBL1Y, VitaminD3-VDR-RXR, WDR33, ZFP106, ZNF226, ZNF362, ZNF711, ZNF354A | 21 | 33 | Gene Expression, RNA Trafficking, Developmental Disorder |

TABLE 3-continued

Regulated Networks from Lung Cancer Sample

| ID | Molecules in Network | Score | Focus Molecules | Top Functions |
|---|---|---|---|---|
| 60 | adenylate kinase, AK2, AK3, AK3L1, ALKBH6, AQP3, ARL17P1, ATG2B, BMP2K (includes EG: 55589), BSDC1, C14ORF105, C16ORF61, C1ORF50, C2-C4b, CD55, CD302, COQ10B, CTDSPL2, FAM107B, GLA, GPATCH2, GPR39, HNF1A, HNMT, HSPC111, LSG1, MCCC1, MRPS18B, NRD1, PCNP, PHF2, TSC22D2, UROD, WDSOF1, ZBTB20 | 21 | 33 | Cardiovascular Disease, Cell Morphology, Genetic Disorder |
| 61 | ADAMTSL4, AGK, BCL2L14, C2ORF28, CCDC6, CREB5, DNPEP, ERK, GPER, KLB, LOXL1, LPP, MAFB, MAFF, MAFK, MPZL1, musculoaponeurotic fibrosarcoma oncogene, NFE2, NFE2L1, NFE2L3, NRF1, NTN4, PALLD, PPP2R2D, PRRX1, RP6-213H19.1, SH3GLB2, SPRED1, SPRED2, SPRY, SPRY1, SPSB1, TESK1, UBA5, WWP1 | 19 | 32 | Connective Tissue Disorders, Hematological Disease, Organismal Injury and Abnormalities |
| 62 | BMI1, Cbp/p300, CBX4, COL5A2, ERBB2IP, HIST2H2AA3, HOXA2, HOXA3 (includes EG: 3200), HOXB8, HOXB6 (includes EG: 3216), HOXD4, MAPKAPK3, MEIS1, PBX1, PBX2, PCGF2, PDZD2, PHC1, PHC2, PHC3, PKNOX1, PKP4, POU3F2, RABGEF1, RAPGEF2, Ras, RNF2, RPS6KC1, RYBP, SHOC2, Sox, SOX4, SOX11, SOX12, UBP1 | 19 | 32 | Skeletal and Muscular System Development and Function, Embryonic Development, Tissue Development |
| 63 | ARCN1, CNKSR2, COPA, COPB1, COPB2, COPG, COPG2, COPZ1, COPZ2, DOCK8, ENSA, Erm, GALNT1, GYS2, Insulin, KIAA1881, LRRC7, MCF2, MOBKL2B, MSN, NME7, NT5C2, PELO, peptide-Tap1-Tap2, PTGFRN, RDX, RHOC, RHOJ, RHOQ, SLC25A11, SLC25A12, SPN, TAPBP, TCHP, TMED9 | 19 | 32 | Cellular Assembly and Organization, Cellular Compromise, Nervous System Development and Function |
| 64 | ACO1, AMPD3, AOAH, C1q, C1QBP, C1QC, C1S, C3-Cfb, CD93, CFH, CFI, Complement component 1, CP, CR1, EGR1, FAM83C, FTH1, FTL, IGKC, IREB2, KIAA0754, KRT10, KRT6A, LECT1, MLX, MLXIP, MNT, MXD1, NAB1, NOPE, PAPPA, PNMA2, SAFB2, TNS3, ZNF292 | 19 | 32 | Cellular Function and Maintenance, Small Molecule Biochemistry, Gene Expression |
| 65 | ALAD, ARL5A, CBX1, CBX3, CBX5, DIAPH2, EEF1B2, eIF, EIF1, EIF5, EIF1AX, EIF2S3, EIF5B, EZH1, HELLS, IFITM2, INSR, IPO13, JAK1/2, LBR, METAP2 (includes EG: 10988), MKI67, MKI67IP, OGN, OLFM2, RNF13, RWDD4A, SEZ6L2, SFRS5, SP100, SURF6, Tk, TK2, ULK2, ZFAND5 | 19 | 32 | Gene Expression, DNA Replication, Recombination, and Repair, Protein Synthesis |
| 66 | 3-hydroxyacyl-CoA dehydrogenase, ACAT1, Acetyl-CoA C-acetyltransferase, CALU, CSE1L, CSTB, DNAJB1, F8A1, FAM120A, FDFT1, GCLC, GCLM, HADHA, HADHB, HSD17B4, HSP90AB1, HSPA5, IBSP, IFITM1, LDL, LMO7, NPC2, OSBP, PDCD6, PON1, PON2, RCN1, S100A9, SCARF1, SCARF2, SFXN3, SPTLC1, TMEM43, TRIP12, XPO1 | 19 | 32 | Amino Acid Metabolism, Small Molecule Biochemistry, Drug Metabolism |
| 67 | BAG5, CCT2, CCT4, CCT5, CCT8, CCT6A, CDC37L1, Chuk-Ikbkb-Ikbkg, CORO1C, FKBP4, FKBP51-TEBP-GR-HSP90-HSP70, HIST1H2BK, HIST4H4 (includes EG: 121504), HSBP1, Hsp70, HSPA4, HSPA6, HSPA9, JMJD2A, MAN2B2, MAP3K1, MAP3K3, PACRG, PDCL, PHF20L1, PTGES3, RPAP3, RPL3, RPL10A (includes EG: 4736), RPL37A, RPS11, RPS23, RPS27L, TCP1, WDR68 | 19 | 32 | Post-Translational Modification, Protein Folding, Drug Metabolism |
| 68 | BGN, CTGF, DCN, ELA2, ELN, ERBB3, ERBB4 ligand, FBN1, FCN2, Fibrin, GLB1, Igfbp, IGFBP4, IGFBP5, IGFBP7, LGMN, MMP2, MMP10, MMP17, MMP25, NPEPPS, PAPPA2, PCSK6, RECK, S100A4, SERPINA1, SERPINA3, SPOCK1, THBS1, THBS2, TIMP2, TMEFF2, TNFAIP6, VCAN, ZBTB33 | 19 | 32 | Cellular Movement, Cancer, Cell-To-Cell Signaling and Interaction |
| 69 | AKT2, Alcohol group acceptor phosphotransferase, BRAF, CCR7, CDC42BPA, CDK6, CFL1, CK1, Cofilin, CSNK1A1, CSNK1G1, CSNK1G3, DAPK1, DDX24, DPYD, DYRK1A, EIF2AK2, EIF4E, FAM98B, FOXO1, GRK6, HIPK1, LIMK2, MIB1, PA2G4, PDS5B, PRKRIP1, PRKX, RAE1, SGK1, SNX5, SSH2, TMEM9B, TPI1, TXNL4B | 19 | 32 | Amino Acid Metabolism, Post-Translational Modification, Small Molecule Biochemistry |
| 70 | APLN, COL11A1, Cyclin B, CYP2R1, DDX42, DNM3, DNM1L, Dynamin, EWSR1, HIPK2, HMGA1, HSPB8, MPHOSPH8, NFYA, NRGN, p70 S6k, PACSIN2, PDPK1, PFN1, RANBP9, RPS6KA3 (includes EG: 6197), RPS6KB1, SLC9A1, SUPT7L, TAF1, TAF2, TAF4, TAF8, TAF10, TAF11, TAF13, THRA, TP53INP1, VDR, XPO6 | 19 | 32 | Nutritional Disease, Cell Cycle, Hair and Skin Development and Function |

TABLE 3-continued

Regulated Networks from Lung Cancer Sample

| ID | Molecules in Network | Score | Focus Molecules | Top Functions |
|----|---|---|---|---|
| 71 | ATXN2L, C5ORF22, CASP2, Caspase, CENPO, DGCR8, DHPS, E2f, EIF2AK3, EIF4G2 (includes EG: 1982), FAM33A, GAS2L1, GOLT1B, Hdac, HDAC4, HDAC9, HIST1H2AB, HOPX, LRDD, MOCS2, MTCH1, NUSAP1, PSME3, RNASEN, ROCK1, RPL9 (includes EG: 6133), SNRPC, SPEN, STK24, SUMO2 (includes EG: 6613), TMEM126B, WBP4, XAF1, ZBTB1, ZNF160 | 19 | 32 | Cellular Function and Maintenance, Connective Tissue Development and Function, Viral Function |
| 72 | ARRB1, CD164, CPNE8, DDX27, DNAH3, DNAL1, GLRX2, NADH dehydrogenase, NADH2 dehydrogenase, NADH2 dehydrogenase (ubiquinone), NDUFA3, NDUFA4, NDUFA5, NDUFA6, NDUFA11, NDUFA12, NDUFAB1, NDUFB1, NDUFB2, NDUFB4, NDUFB5, NDUFB7, NDUFB8, NDUFB10, NDUFC2, NDUFS1, NDUFS5, NDUFS8, NDUFV1, NDUFV3 (includes EG: 4731), RPL7L1, RPS17 (includes EG: 6218), RTF1, SCYL2, ZRANB2 | 19 | 32 | Genetic Disorder, Neurological Disease, Cell-To-Cell Signaling and Interaction |
| 73 | ANK1, ARID4B, ATF7IP2, B4GALT1, B4GALT5, B4GALT6, B4GALT7, CCNL2, CDC2L2, CTSD, CYP7B1, Esr1-Estrogen-Sp1, FUSIP1, Galactosyltransferase beta 1,4, IFITM3, MGEA5, MIER1, MRC1, MUC5B, NFYC, PDHX, POGZ, RHAG, SFRS7, SFTPA2B, SLC11A1, SP1, SUDS3, TFAM, TFB2M, TRA2A, TXNDC12, WDFY3, ZFYVE20, ZNF587 | 19 | 33 | Gene Expression, RNA Post-Transcriptional Modification, Carbohydrate Metabolism |
| 74 | ADAMTS5, AIF1, COP1, CYSLTR1, ERAP1, FAM105B, GALNS, GNL1, IL-1R, IL-1R/TLR, IL1B, IL1R1, 1L1R2, IRAK, IRAK1, IRAK2, IRAK3, IRAK4, IRAK1/4, MYLK3, NUCB2, PELI1, PLXDC2, PTP4A1, SCUBE2, SEPP1, TICAM2, TIFA, TIRAP, TLR4, TLR8, TLR10, UAP1, UGDH, ZC3H12A | 18 | 31 | Cell Signaling, Carbohydrate Metabolism, Nucleic Acid Metabolism |
| 75 | ABCC9, AIM1, AJAP1, APOD, ARL4A, BCL9, Bcl9-Cbp/p300-Ctnnb1-Lef/Tcf, CDH9, CELSR1, CST4, CTNNB1, DKK3, GPR137B, Groucho, HES1, ID4, KCNIP4, L-lactate dehydrogenase, LDHA, LDHB, LEF1, LEF/TCF, LEO1, MGAT5, MUC6, NLK, PLS3, PTCH1, SFRP2, TAX1BP3, TCF4, TCF7L2, TLE1, TLE4, UEVLD | 18 | 31 | Gene Expression, Embryonic Development, Tissue Development |
| 76 | AHR, Ahr-aryl hydrocarbon-Arnt, C12ORF31, CAMK2N1, COL1A1, COL5A1, COL5A3, CSF1, Esr1-Estrogen, GPR68, GUCY1B3, HOOK3, IFNGR1, KLF3, LOX, MRC2, MSR1, NFIA, NFIB, NFIC, NFIX, Nuclear factor 1, P4HA1, RAB5B, RIN2, RIN3, RRAS2, SERPINH1, SKI, SLC25A5, SLC30A9, SLC35A2, SWI-SNF, TPD52L3, TRAM2 | 18 | 31 | Gene Expression, Hepatic System Disease, Dermatological Diseases and Conditions |
| 77 | C10ORF119, DNA-directed DNA polymerase, EIF2AK4, H2AFX, HUS1, IL1, LNPEP, MCM4, MCM10, Mre11, MRE11A, ORC2L, ORC3L, ORC6L, PAPD5, POLE4, POLH, POLS, RAD1, RAD17, REV1, RFC3, RPA, RPA3, TAX1BP1, TERF1, TERF2IP, TNKS, TNKS2, TNKS1BP1, TP53BP1, XAB2, XPA, XRCC5, ZBTB43 | 18 | 31 | DNA Replication, Recombination, and Repair, Cell Cycle, Gene Expression |
| 78 | ACTR1B (includes EG: 10120), ACVR1, ACVR1B, ACVR2A, ACVRL1, CUL5, FBXO3, FBXO24, FBXO34, FGD6, FOXH1, INHBC, NARG1, NAT5, PLEK, PREB, SAMD8, SAR1A, SMAD2, Smad2/3, SMURF1, SNX1, SNX2, SNX4, SNX6, TBL2, Tgf beta, TGFBR, TGFBR1, TRIM35, Type I Receptor, UHMK1, VPS29, VPS35, ZFYVE16 | 18 | 31 | Embryonic Development, Tissue Development, Organismal Development |
| 79 | Ahr-Aip-Hsp90-Ptges3-Src, ANKRD12, ATRX, CUGBP1, CXCL12, DNAJ, DNAJC, DNAJC1, DNAJC3, DNAJC7, DNAJC8, DNAJC10, DNAJC11, DNAJC14, DNAJC15, EIF2AK1, FEZ2, FUBP1, Hsp90, ICK, IFNAR2, IRF6, LATS2, LOXL2, MARCKS, MBNL1, NEK1, NLRP3, PPP5C, PRKRIR, SAV1, STK3, STK4, TXNL1, ZNF350 | 18 | 31 | Cell Morphology, Hematological System Development and Function, Immune and Lymphatic System Development and Function |
| 80 | ANKH, BTBD1, CBFB, CHST8, CK1/2, CLPP, COL4A1, CSF1R, CSNK2A1, CSNK2B, CTNNBL1, CXCL6, GALNT2, GALNT3, GALNT4, GALNT7, Glutathione peroxidase, GPX3, KYNU, LOC493869, LSAMP, LTA4H, MUC1, PCSK7, peptidase, Polypeptide N-acetylgalactosaminyltransferase, POU2F2, PRNP, PRNPIP, RUNX1, SEPHS1, SPP1, TDP1, TOP1, TRIM5 | 18 | 31 | Post-Translational Modification, Cancer, Gene Expression |

TABLE 3-continued

Regulated Networks from Lung Cancer Sample

| ID | Molecules in Network | Score | Focus Molecules | Top Functions |
|---|---|---|---|---|
| 81 | AAK1, Adaptor protein 2, AMD1, AP2A1, Arf, ARF3, ARFGEF1, ARFIP1, DLEU2, EHBP1, EHD2, Fcgr3, FCGR3A, GABAR-A, GABRB1, GABRP, GBF1, HIP1, LAMP1, LDLRAP1, PABPN1, PICALM, RIT1, RPL4, RPL11, RPL15, RPL21, RPL24, RPL27, RPL28, RPL12 (includes EG: 6136), RPLP2, SHC1, SYT6, SYT7 | 17 | 31 | Cellular Function and Maintenance, Cell Signaling, Molecular Transport |
| 82 | ANAPC1, ANTXR, ANTXR1, ANTXR2, BIRC2, BIRC6, CBL, E3 RING, PARK2, Proteasome, RNF5, SORBS1, SUGT1, TCEB1, UBE2, UBE2A, UBE2B, UBE2D1, UBE2D2, UBE2D3, UBE2E1, UBE2E2, UBE2F, UBE2G1, UBE2G2, UBE2H, UBE2I, UBE2J1, UBE2N, UBE2R2, UBE2V1, UBOX5, UBR3, XIAP, ZMYM2 | 17 | 31 | Post-Translational Modification, Protein Degradation, Protein Synthesis |
| 83 | 3alpha-hydroxysteroid dehydrogenase (A-specific), AKR1C1, AKR1C2, AKR1C3, CLSTN2, COL6A1, COL6A3, DPYSL2, DPYSL3, DPYSL4, DPYSL5, DYRK2, FAT, GOLGA3, GRIP1, IGF1, KIF5B, KLC1, KLC2, KLF9, ME1, MGA (includes EG: 23269), NCOA4, OSBPL7, SERCA, SNED1, SRA1, SRD5A1, SRR, STRBP, T3-TR-RXR, Thyroid hormone receptor, TRAK1, TRAK2, Trans-1,2-dihydrobenzene-1,2-diol dehydrogenase | 16 | 30 | Drug Metabolism, Genetic Disorder, Lipid Metabolism |
| 84 | ARF4, ARL6IP1, BRCC3, BTRC, CAND1, Cyclin D, Cyclin E, E3 co-factor, FBXW7, FBXW11, FZR1, ITCH, JUN, MEF2B (includes EG: 4207), MIA3, N4BP1, NEDD9, PXDN, Scf, SEC63, SEC61A2, SEC61B, SEC61G, SERP1, SKP1, SKP2, SLC30A1, SNAPC5, SUMF2, TAL1, TCF12, TCF20, Tcf 1/3/4, TLOC1, WEE1 | 16 | 30 | Cellular Development, Hematological System Development and Function, Immune Response |
| 85 | ALOX5AP, B2M, CD4, CD74, CD1C, CD1D, CIITA, CLEC7A, CSF2, Csf2ra-Csf2rb, CTSS, FCER1G, HLA-DMA, HLA-DOA, HLA-DPA1, HLA-DPB1, HLA-DQA1, HLA-DQB1, HLA-DQB2, HLA-DRA, HLA-DRB1, HLA-DRB4, Ifn alpha, IL12B, IL5RA, LAMP2, LYPLA3, MHC Class II, MHC II-β, Mhc2 Alpha, MOG, RBM3, RFX5, SLC39A6, SSBP1 | 16 | 30 | Immune Response, Cell-To-Cell Signaling and Interaction, Immunological Disease |
| 86 | ARHGAP1, ARHGAP5, ARHGAP6, ARHGAP8, ARHGAP9, ARHGAP15, ARHGAP29, ARHGEF2, BNIP2, CADM1, CASK, CD226, CNKSR3, DLC1, EVI5, F11R, GRLF1, INPP5A, Itgam-Itgb2, JAM, JAM2, JAM3, KIFAP3, LIN7B, MAGI, MAGI1, MLLT4, NRXN2, PVR, RAC1, Ras homolog, RhoGap, SH3BP1, SYNPO, THY1 | 16 | 30 | Cell Signaling, Cell-To-Cell Signaling and Interaction, Tissue Development |
| 87 | BRD4, CAM, CLDN1, CLDN10, CLDN11, CLDN15, DDX18, Guk, INADL (includes EG: 10207), ITGB1, LAMA2, LAMB1, LAMB3, LAMC1, MPDZ, MPP2, MPP5, Nectin, NPNT, OCLN, PLEKHA2, Pmca, PPP1R9A, PPP1R9B, RAB21, TBX5, TEAD2, TEAD3, TEAD4, TGOLN2 (includes EG: 10618), TSPAN, TSPAN3, TSPAN6, WWTR1, YAP1 | 16 | 30 | Cellular Movement, Nervous System Development and Function, Gene Expression |
| 88 | ASH1L, AURKA, CCDC71, CENTD2, CHFR, CLDND1, ERCC6, GSTA4, GTF2A1, HIST2H3D, Histone h3, JMJD2C, KIAA0265, LARP2 (includes EG: 55132), LOC26010, MAGED2, MTUS1, NAIP, NFATC2IP, NUP37, NUP43, PARP10, SAR1B, SEC13, SEC31A, SETMAR, Taf, TFIIA, TFIIE, TFIIH, TM4SF18, UBB, WDR1, ZBTB44, ZDHHC11 | 16 | 30 | Cell Morphology, Cellular Assembly and Organization, Cell Cycle |
| 89 | ANGPT2, ATP2B4, C7ORF16, Calcineurin protein(s), CBLB, CHP, CKM, CTSL2, DBN1, DLG1, FBXO32, GPI, GRIN2C, MAPK9, MARCKSL1, MEF2, MEF2A, MEF2C, MYOZ2, Nfat, NFAT complex, NFATC2, NIPBL, ODF2L, PARP14, PDDC1, Pp2b, PPP3CA, PPP3CB, PPP3CC, PRSS23, RCAN1, SOD1, TRAPPC4, XPNPEP1 | 16 | 30 | Skeletal and Muscular System Development and Function, Tissue Morphology, Dermatological Diseases and Conditions |
| 90 | AFF1, ALP, ANAPC13, ARNT, BMP, BMP7, BMP8A, C10ORF118, CDC16, CDC27, CEP135, CFDP1, CTDSP2, CXXC5, EXPH5, KIAA0256, KIAA0372, KIAA1267, MAST4, PAX8, PRDM4, Rar, RNF123, Smad, SMAD1, SMAD3, SMAD5, SMAD9, Smad1/5/8, TMEM57, ZDHHC4, ZMIZ1, ZNF83, ZNF251, ZNF557 | 16 | 30 | Cellular Development, Connective Tissue Development and Function, Cell Signaling |

TABLE 3-continued

Regulated Networks from Lung Cancer Sample

| ID | Molecules in Network | Score | Focus Molecules | Top Functions |
|---|---|---|---|---|
| 91 | ABCC1, ACTA2 (includes EG: 59), CAMLG, CCND2, CDKN2C, CDKN2D, CES2 (includes EG: 8824), Dgk, ERP29, ESD, ETS1, Fgf, FGF13, FKBP5, Glutathione transferase, GSTM2, GSTM1 (includes EG: 2944), GSTO1, IFI16, INHBA, ITGB2, MGST1, MGST2, MTHFD2, NFE2L2, PCYT1B, PMF1, PPIB, PXR ligand-PXR-Retinoic acid-RXR&alpha, Rb, RUNX2, TCF3, THRB, TYMS, ZNF302 | 16 | 30 | Tissue Morphology, Cancer, Reproductive System Disease |
| 92 | ADAM9, ADAM10, ADAM12, ADAM17, ADAM21, ADAM23, ADAM30, ADK, APBA2, APLP2, APP, BLZF1, C5ORF13, CHN1 (includes EG: 1123), ERBB4, GNRHR, GORASP2, ITM2B, Metalloprotease, NCSTN, NECAB3, Notch, PCDHGC3, PPME1, PROCR, PSEN1, Secretase gamma, SH3D19, SLC1A2, SPON1, SPPL2A, TM2D1, TMED2, TMED10, YME1L1 | 16 | 32 | Developmental Disorder, Neurological Disease, Organ Morphology |
| 93 | ANAPC10, CCNG2, EEF2, FGFR1OP, GLUL, Glycogen synthase, HSPD1 (includes EG: 3329), L-type Calcium Channel, M-RIP, MAP2K1/2, Mlcp, MPST, MYCL1, PARK7, PP1, PP1/PP2A, PPP1CB, PPP1CC, PPP1R8, PPP1R10, PPP1R11, PPP1R12A, PPP2CA, PPP2R1B, PPP2R2A, PPP2R2B, PPP2R5C, PRDX1, PTPN7, RAB18, RAB11A, RAB11FIP1, RALA, RAP1A, WDR44 | 15 | 29 | Cancer, Cell Death, Reproductive System Disease |
| 94 | AKAP, AKAP1, AKAP4, AKAP7, AKAP8, AKAP9, AKAP13, AKAP10 (includes EG: 11216), BMPR, C3ORF15, CBFA2T3, CD40, FLJ10357, GLO1, LZTS1, MYCBP, PDZK1, Pka, Pki, PRKACB, PRKAR1A, PRKAR2A, PSMC3IP, RAB13, Rap, RFX2, RPL30, SEP15, SLC30A7, sPla2, SUSD2, TYRP1, UGCGL1, XCL1, ZNF652 | 15 | 29 | Protein Synthesis, Molecular Transport, Protein Trafficking |
| 95 | AGTPBP1, ANK2, ANK3, BCL10, CASP7, CD3, CD3E, CFLAR, Ciap, CTLA4, DIABLO, ERC1, FASLG, FOXP1, IKBKB, IKK, ITPR, MALT1, MOAP1, NF-κ B, PDPN, PPFIA1, PPM1B, PTPN2, PTPRC, ROD1, SOS2, TCR, TNFAIP3, TNFRSF10A (includes EG: 8797), TNFRSF10B, TNFSF10, TNIP2, TRAF3IP2, TXNRD1 | 15 | 29 | Cell Death, Hematological Disease, Immunological Disease |
| 96 | ANKRD17, BCL3, C1ORF41, C2ORF30, CCDC82, EFR3A, ERMP1, FILIP1L, FOXO3, HBP1, Hd-perinuclear inclusions, HDAC8, HERC3, Hsp27, Ikb, KLF5, MON2, MRCL3, MYO6, Nos, NSFL1C, PHF17, RARA, RBL2, SFRS15, SMG5, SMG7, SNX3, SPG20, Tnf receptor, TNFRSF1A, TXLNA, Ubiquitin, UFC1, VHL | 15 | 29 | Inflammatory Disease, Renal Inflammation, Renal and Urological Disease |
| 97 | AK5, BMI1, BNIP3 (includes EG: 664), BTBD11, C10ORF58, CAV1, CBX4, COG5, DBT, DDEF1, FLJ38973, HIST2H2AA3, JARID1C, LOC653441, MCRS1, MEG3 (includes EG: 55384), NFX1, NUCKS1, PCGF2, PHC1, PHC2, PRKD1, PXN, RING1, RNF2, RPL7, RPL22, RYBP, TERT, TMEM70, VEGFA, XRCC5, YWHAQ (includes EG: 10971), ZNF313, ZRANB1 | 15 | 29 | Tissue Development, Cell Cycle, Cellular Development |
| 98 | ADC, ANXA4, CD244, CKS2 (includes EG: 1164), CTSB, CTSL2, EDNRA, ELK3, FARS2, FBN1, FOS, GCNT1, GNL2, heparin, HNRNPA2B1, IL15, IL1R1, KIAA1600, MGAT4A, MSLN, NUBP1, Ornithine decarboxylase, P2RY1, PCNX, PUNC, RPS18, SERPINE2, TCEA1, TFPI, THBS4, TNC, TXNRD1, VWA1, ZNF33A | 14 | 28 | Cancer, Gastrointestinal Disease, Tumor Morphology |
| 99 | ANGEL2, AP2A1, ARL1, ARMC1, BRF2, C7ORF58, C9ORF64, CCDC59, CHP, COPB2, DPM1, HNF4A, KIAA1704, MRPL3, MRPL32, MRPS21 (includes EG: 54460), PDXDC2, SF3B1, SLC44A1, SLMO2, SRPRB, SSR3, TBC1D20, TIMM23, TMEM33, TNPO3, TOE1, TXNL4B, ZNF644 | 14 | 25 | RNA Post-Transcriptional Modification, Cellular Assembly and Organization, Carbohydrate Metabolism |
| 100 | ABI1, ACTR2, ACTR3, AHNAK, Alpha actin, ARHGDIA, Arp2/3, ARPC2, ARPC3, ARPC4, ARPC5, ARPC1B, ARPC5L (includes EG: 81873), C3ORF10, C8ORF4, CACNB2, CORO1B, CTTN, F Actin, FER1L3, G-Actin, HCLS1, IQGAP2, IQUB, MAST2, NCF4, NCKAP1, PCDH24, PFN, Pkc(s), SSH1, Talin, WASF1, WASF2, WIPF1 | 14 | 28 | Cellular Assembly and Organization, Cell Signaling, Cell Morphology |

EXAMPLE 3

Formulation of Treatment for Epithelioid Hemangioendothelioma

Biopsied tumor tissue from the patient was assayed for gene expression using Agilent transcription mRNA profiling and compared to the normal expression profile obtained from a database. 7,826 Genes had expression ratio thresholds of 3-fold up- or down-regulation, and a significance P-value of 0.05.

Using a tool provided by Ingenuity Systems, the of 7,826 genes were subjected to an algorithm which finds highly interconnected networks of interacting genes (and their corresponding proteins). Protein/protein interaction is determined directly from the research literature and is incorporated into the algorithm. These findings were then further analyzed to find particularly relevant pathways which could provide potential therapeutic targets or, if possible, clusters of interacting proteins which potentially could be targeted in combination for therapeutic benefit.

An initial analysis was done to confirm that the global gene expression from the tumor sample was generally consistent with a priori expectations for a neoplasm of this type. The networks that were assembled by the protein interaction algorithm for up- or down-regulated genes were analyzed with respect to the cellular and organismal functions of their individual component genes. The four top-scoring networks (with respect to the interconnectedness of their component genes) were greatly enriched in the following functions:

| | |
|---|---|
| Cellular Growth and Proliferation | Hematological System Development and Function |
| Immune Response | Endocrine System Disorders |
| Immunological Disease | Metabolic Disease |
| Viral Function | Carbohydrate Metabolism |
| Molecular Transport | Connective Tissue Disorders |
| Organismal Injury and Abnormalities | |

This overall pattern is consistent with what one might expect from the global gene expression of an endothelial cell-derived tumor as compared to normal blood vessel, which helps to confirm that the signals are from the tumor sample and that the integrity of the gene expression milieu has been maintained. The entire list of networks and their associated functions is in the table at the end of this example.

Figure 9:
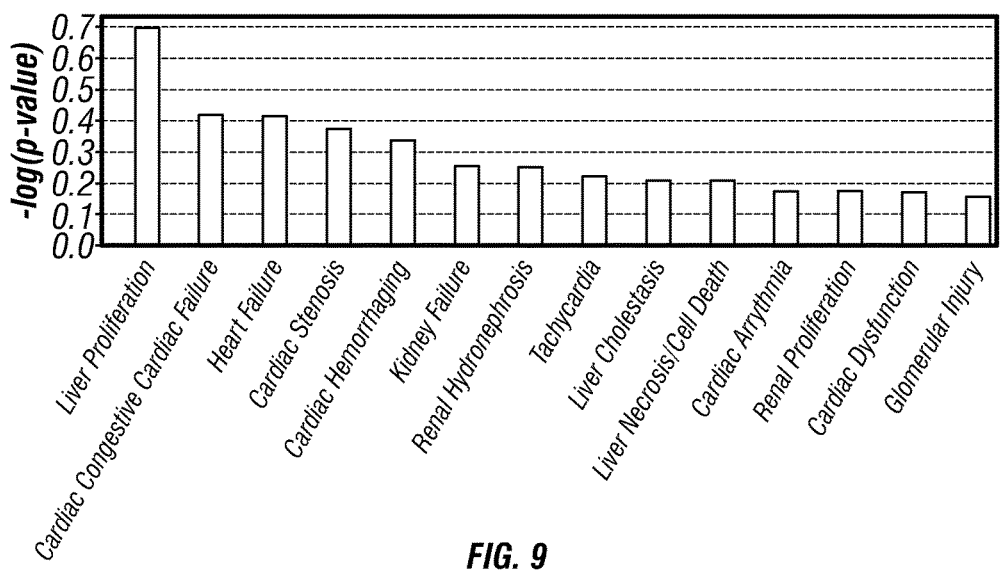
FIG. 9 is a graph showing cellular functions enriched in the regulated genes from tumor samples of a patient with liver cancer.
Figure 9:
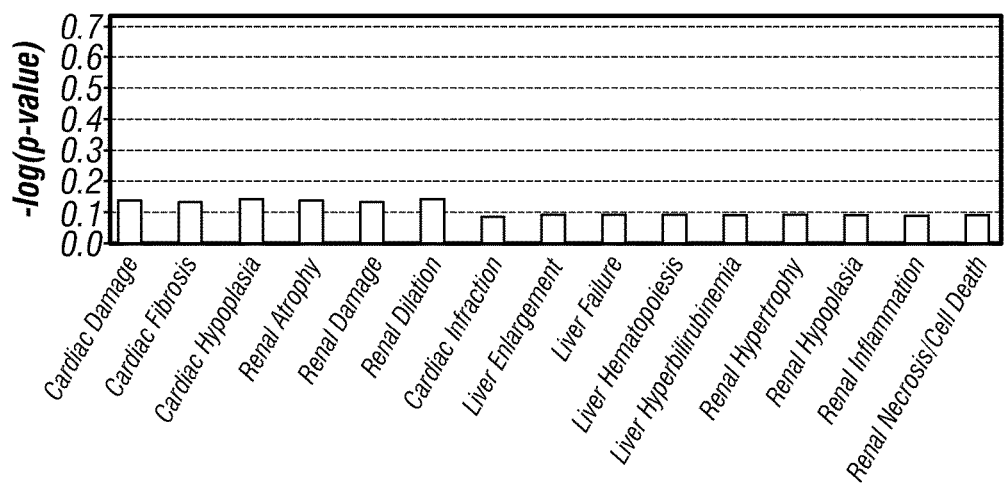

The list of over- or under-expressed genes was scored for associated negative or adverse cellular functions. The highest scoring category was liver proliferation. (FIG. 9) Several cardiovascular gene functions were also high, probably as a result of normal blood vessel tissue being used as the control, i.e., an apparent down-regulation of many genes normally expressed in blood vessels. Both of these classes of findings are consistent with global gene expression patterns of tumor tissue compared with normal blood vessel tissue.

Figure 10:
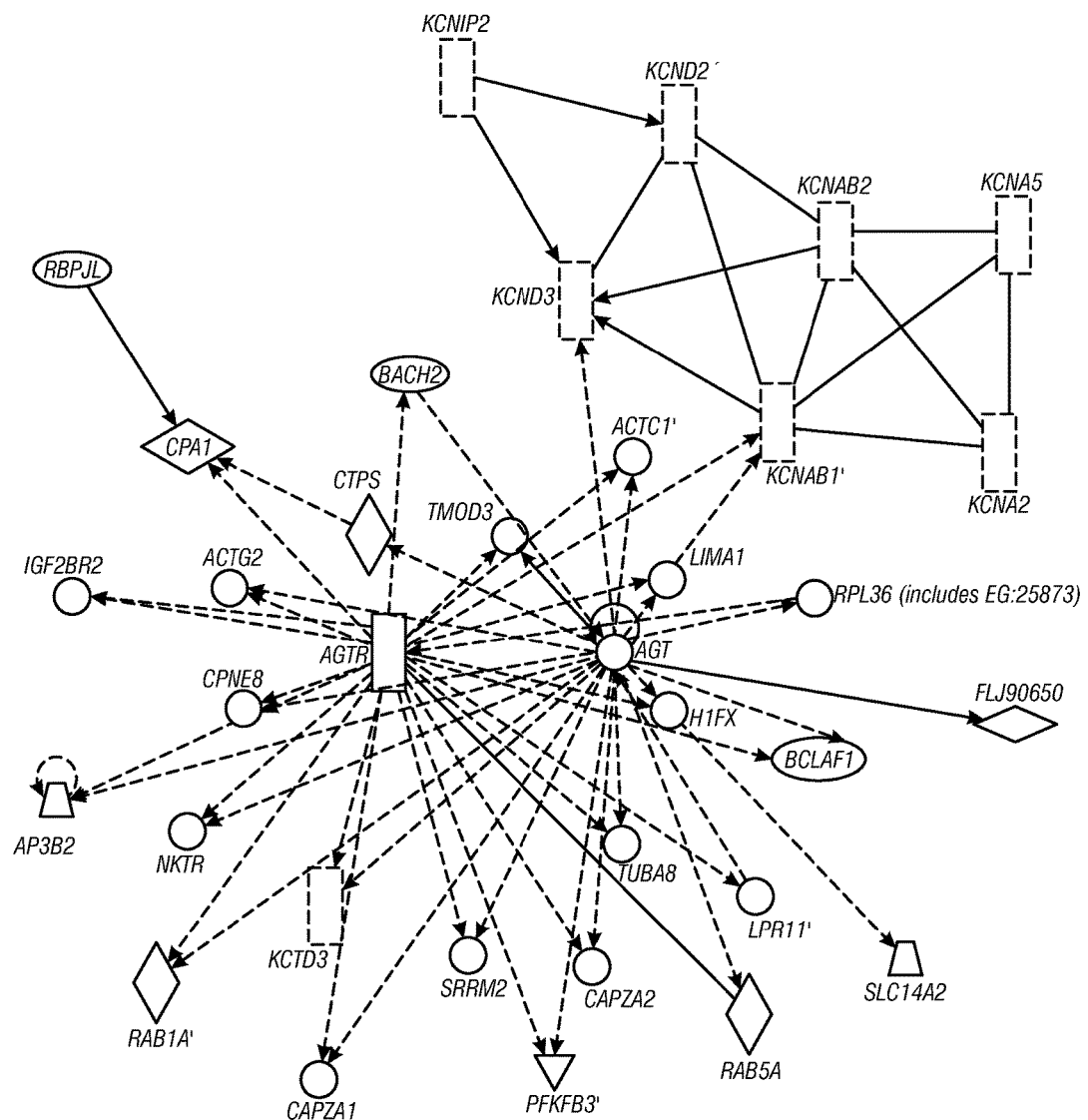
FIG. 10 shows the network containing members of the angiotensin pathway as described in the art.

Most notably, a large, highly interacting network of regulated genes was found in the tumor sample centered on the angiotensin II receptor, type 1 (AGTR1; AT1R) including pre-angiotensinogen, the gene product precursor for angiotensin II, as shown in FIG. 10.

The angiotensin pathway (or renin angiotensin system (RAS)) has a well established role in mediating blood pressure and volume, both systemically, and more recently in local organ systems. Indeed, the pathway is targeted therapeutically in the treatment of hypertension both via reduction of angiotensin II (ACE inhibitors) and by blocking AT1R receptors. More recently, however, AT1R has been implicated as a potential therapeutic target in a number of cancers, both through antimitotic and anti-vascularization mechanisms (Ino, K., et al., *British J. Cancer* (2006) 94:552-560.e; Kosugi, M., et al., *Clin. Cancer Res*. (2006) 2888-2893; Suganuma, T., et al., *Clin. Cancer Res*. (2005) 11:2686-2694), however, clinical and epidemiological results have been mixed (Deshayes, F., et al., *Trends Endocrinol Metab*. (2005) 16:293-299). It does represent an attractive target however, since there are numerous available ATR1 blockers such as the sartans, which have been widely prescribed (chronically) for hypertension.

Additionally, it is known from the literature that AT1R trans-activates the EGF receptor (EGFR) (Ushio-Fukai, M., et al., *Arterioscler Thromb Vasc Biol* (2001) 21:489-495) which is a demonstrated player in oncogenic processes and an established target for several cancer drugs (e.g., Erbitux™, Iressa®, Tarceva®). In the tumor sample, both EGFR and its family member and interacting receptor EGFR2 (Her2/Neu; erbb2) which is the target for the anti-cancer drug Herceptin®, are also significantly up-regulated. It should be noted, that another analyst found that EGFR protein, as demonstrated by immunohistochemistry (IHC) is not seen in the tumor sample. However, there is a body of literature demonstrating that the presence of the EGFR protein target, as demonstrated by IHC, is actually not a good predictor of clinical response to anti-cancer drugs that target EGFR (Chung, K. Y., et al., *J. Clin. Oncol*. (2005) 23:1803-1810.i). EGFR copy number change (which would be reflected in increased mRNA as detected by expression profiling) is a better predictor (Ciardiello, F., et al., *N. Engl. J. Med*. (2008) 358:1160-1174). A further validation study was performed using copy number which found that EGFR was indeed mutated.

Figure 11:
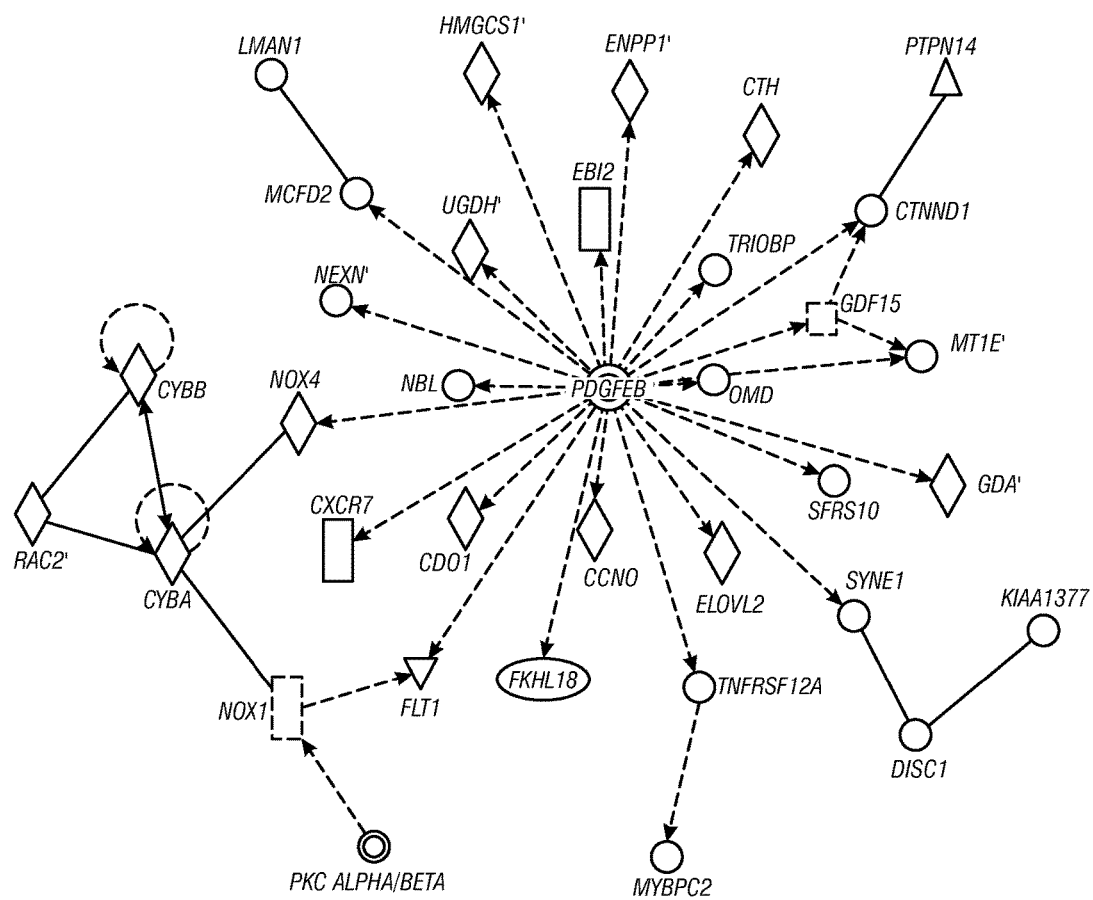
FIG. 11 shows the network containing the NOX1 gene as described in the art.

One caveat of this analysis is the possibility of "contamination" of tumor tissue with normal liver tissue, which could potentially be a confounding variable. In fact, both AT1R and EGFR are expressed in higher amounts in normal liver than in normal blood vessel, which at least in principal could explain the over-expression of these two targets. One finding, however, makes this possibility less likely: While the exact mechanism for the trans-activation of EGFR by ATR1 activation is unknown, there is evidence that a key intermediate is the gene NOX1 (Ding, G., et al., *Am. J. Physiol. Renal Physiol*. (2007) 293:1889-1897). NOX1 was highly up-regulated in the tumor sample (FIG. 11), yet is not at all highly expressed in normal liver relative to blood vessel, indicating a tumor source for the very high NOX1 signal. NOX1 itself does not represent a therapeutic target, however it may be an important marker for activation of the ATR1-EGFR interaction. Thus, this both confirms the AT1R/EGFR pathway activation, and is consistent with tumor localization of the up-regulated genes.

There is a second issue which makes the angiotensin pathway a potentially attractive target to emerge from this analysis. While the internal validation described above indicates that the tissue samples used for the gene expression study are indeed primarily tumor tissue, any profiling based on macro-dissection of tissue always has the possibility of measuring some signal from tumor stroma as opposed tumor cells per se. The angiotensin pathway, however, has been implicated in tumor biology both via a mitotic effect and a tumor vascularization effect. Angiotensin receptors localized to the stroma are thought to play a role in tumor vascularization, while tumor receptors are thought to mediate a mitotic effect. Therefore there might be a relevant to therapeutic role of decreasing activity in this pathway regardless of whether the overexpression is happening in tumor or the stroma.

The overall gene expression findings are consistent with an endothelial-derived tumor in the liver, based on global gene regulation. In addition, one particular pathway emerged from the analysis which has several potential points of therapeutic intervention that would not have been considered as part of the standard oncology approaches. In particular, the precursor angiotensin II (AGT), its receptor (AT1R; AGTR1) are both up-regulated, as well as EGFR and EGFR2 (Her2/Neu; erbb2). AGTR1 transactivates EGFR, which in turn heterodimerizes with EGFR2; the activated receptor is known to play a role in oncogenesis. Therefore, targeting AT1R, EGFR or EGFR2, possibly in combination, is suggested. Furthermore, the angiotensin pathway may represent a particularly robust target with respect to localization, as there may be benefit to blocking both tumor or stroma activity.

For the VEGF pathway, algorithm 1 gives probability of pattern being produced by chance ($\Pi$) as $1 \times 10^{-7}$.

The total pathway elements (q)=25, which are 1 ligand (VEGF), 1 receptor (VEGFR), 16 downstream in survival branch (PI3K, PLCV, PIP2, PIP3, DAG, IP3, CA2, 14-3-3σ, XHR, AKT, eNOS, PKC α/β, BAD, Bcl XL, NO, Bcl 2), 7 in proliferative branch (SHC, GRB2, SOS, Ras, c-Raf, MEK 1/2, ERK 1/2). The total aberrant genes consistent with hypothesis (n)=12; which are 1 ligand (VEGF), 1 receptor (VEGFR), 7 downstream in survival branch (PI3K, PLCV, 14-3-3σ, XHR, AKT, PKC α/β, Bcl XL), 3 in proliferative branch (SHC, GRB2, ERK 1/2). The total number of possible pathways (N): Assume ~200 based on XXX canonical pathways within Ingenuity, with a cut-off probability (p)=0.05.

EXAMPLE 4

Formulation of Treatment of Malignant Melanoma in a Patient

Tumor samples (melanoma metastases to lung) and normal tissue samples from the same patient (surrounding lung tissue) were obtained at biopsy. Affymetrix transcription profiling data (Hu 133 2.0 Plus), consisting of tumor vs. control gene expression ratios were generated using mRNA from this tissue. These data were filtered to obtain genes with an expression ratio threshold of 1.8-fold up- or down-regulation, and a significance P-value of 0.05.

In addition, DNA samples were processed using Affymetrix SNP Array 6.0 to determine genomic segments of amplification or deletion, referred to herein as Copy Number/Loss of Heterozygosity (CN/LOH) analysis. Individual genes contained in the amplified or deleted segments were determined using a genome browser.

A total of 5,165 genes from transcription profiling were passed on to network analysis. The filtered list of 5,165 genes was subjected to an algorithm (Ingenuity Systems) that finds highly interconnected networks of interacting genes (and their corresponding proteins). Proprietary software tools were used to integrate the networks with the CN/LOH data. Protein/protein interaction is determined directly from the research literature and is incorporated into the algorithm. These findings were then further analyzed to find particularly relevant pathways, which could provide potential therapeutic targets or, if possible, clusters of interacting proteins that potentially could be targeted in combination for therapeutic benefit.

In addition to the dynamic networks created on the fly from the filtered genes, expression and CN/LOH data can be superimposed onto static canonical networks curated from the literature. This is a second type of network analysis that often yields useful pathway findings.

Before looking for potential therapeutic targets, an initial analysis was done to confirm that the global gene expression from the tumor sample was generally consistent with a priori expectations for a neoplasm of this type. This serves as a crude measure of quality control for tissue handling and microarray processing methodology. The networks that were assembled by the protein interaction algorithm from the filtered list of up- or down-regulated genes were analyzed with respect to the cellular and organismal functions of their individual component genes. The three top-scoring networks (with respect to the interconnectedness of their component genes) were greatly enriched in the following functions:

| | |
|---|---|
| Molecular Transport | Cellular Development |
| Lipid Metabolism | Cancer |
| Reproductive System Development and Function | Gene Expression |
| Cell Signaling | RNA Post-Transcriptional Modification |

This overall pattern is consistent with what one might expect from the global gene expression of a tumor sample, as compared to normal tissue. These are very high-level general categories and by themselves do not point towards a therapeutic class. However they help to confirm that we are looking at signals from the tumor sample and that the integrity of the gene expression milieu has been maintained. The entire list of networks and their associated functions is set forth in Table 4.

Figure 12:
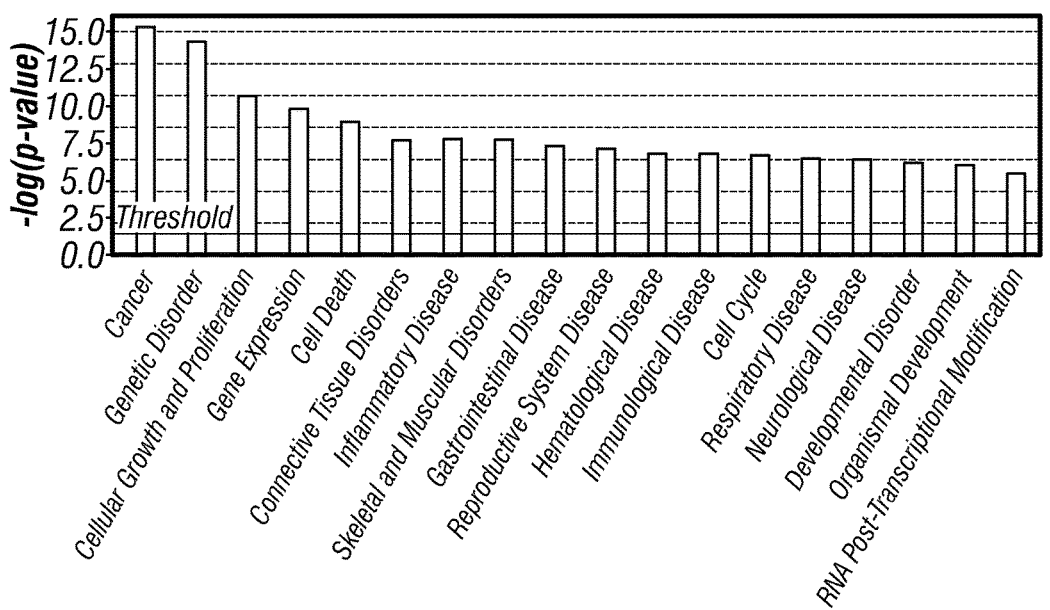
FIG. 12 is a graph showing cellular functions enriched in regulated genes from a melanoma sample.

In addition to a network analysis of the filtered list of 5165 regulated genes, the entire filtered list of genes was scored for associated cellular functions. The highest scoring category was cancer. (FIG. 12) Note also the high scoring of cell proliferative gene functions: Cell Cycle, Cellular Growth and Proliferation, Gene Expression. Both of these classes of findings are consistent with global gene expression patterns of tumor tissue compared with normal tissue.

Three major findings emerged from the analysis. They are presented below in order of the judged strengths of the emergent hypotheses. It should be noted that while the first hypothesis is scientifically stronger, the key drugs that target the pathway are still in clinical trials. An already approved drug may more easily target the pathways in the second and third hypotheses.

First Hypothesis

Figure 13:
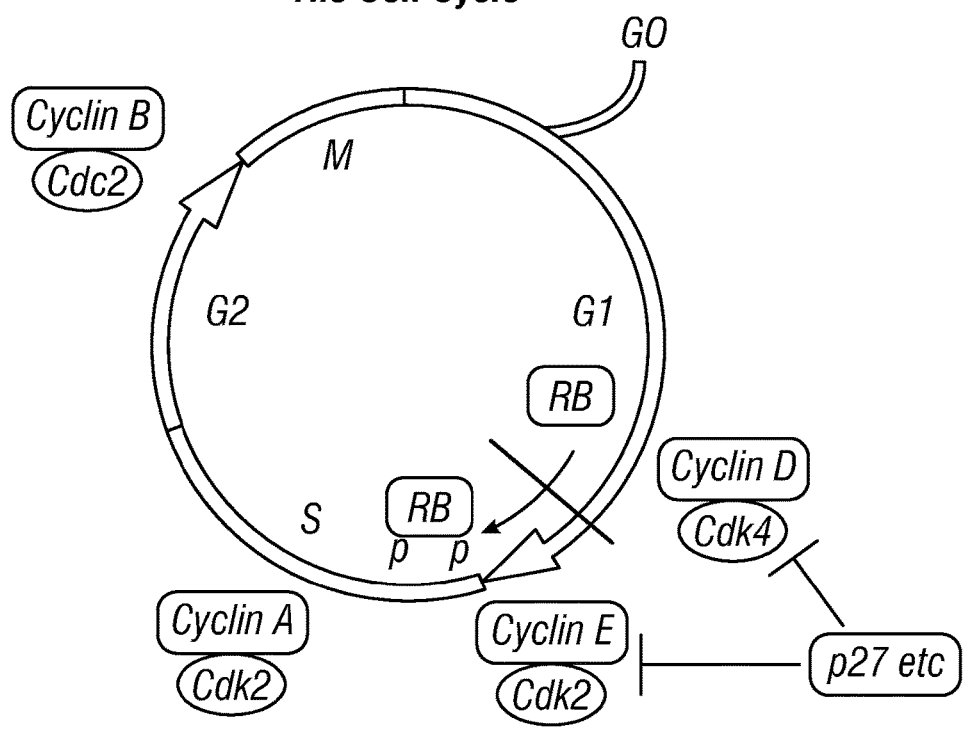
FIG. 13 is a diagram of the cell cycle and the relevance of CDK2.

Cyclin-dependent kinase 2 (CDK2) was found to be highly up-regulated (19-fold) in the tumor. CDK2 is necessary for cell cycle progression from G1 to S phase (FIG. 13). Thus, inhibition of CDK2 would be expected to arrest cells in G1 and therefore block cell division. However, when tested in cancer cells, CDK2 inhibition does not arrest cell growth, with one notable exception: melanoma cells. This has led to the notion that CDK2 is an attractive target in melanoma. The lack of effect in other cancer cells, and more importantly, in normal cells, implies that CDK2 inhibition may lead to melanoma-specific cell cycle arrest, with low toxicity (Chin, et al., 2006; Du, et al., 2004).

Figure 14:
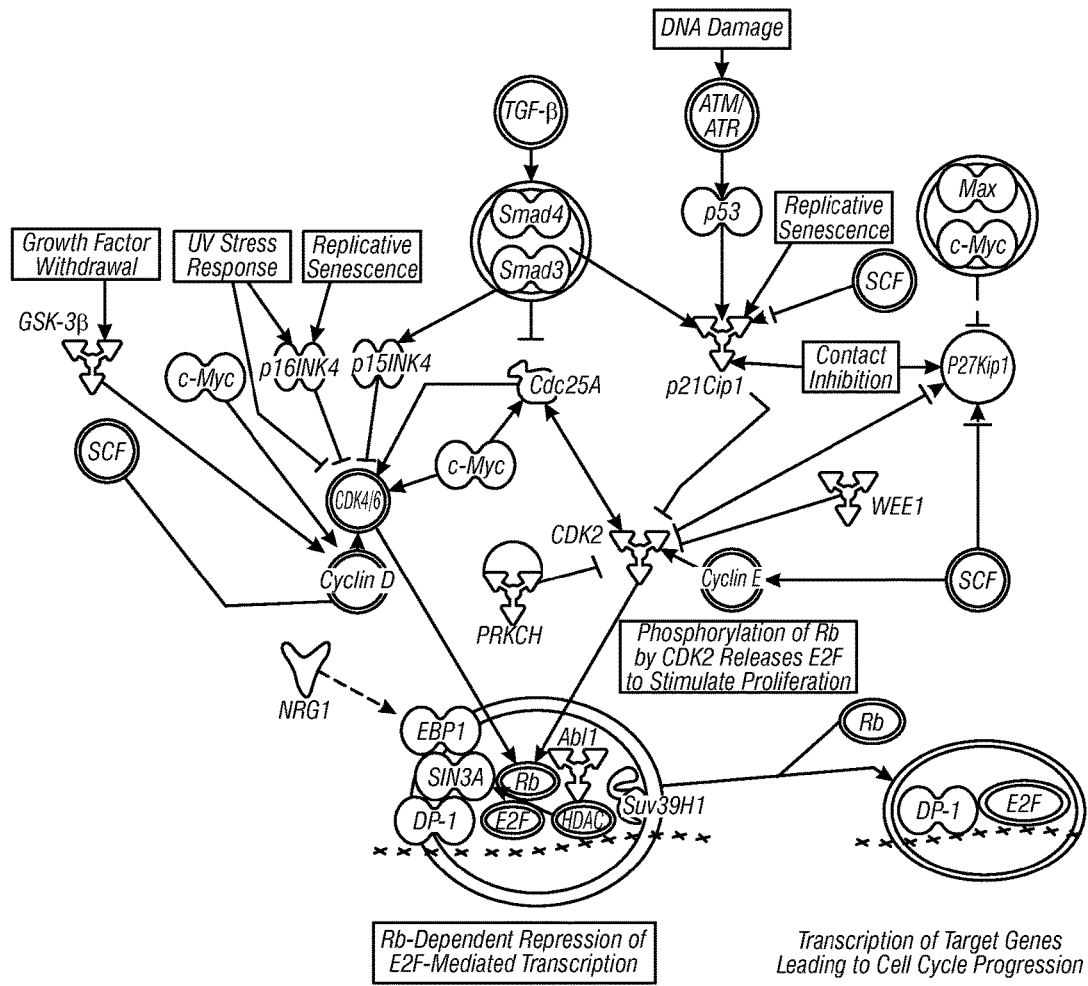
FIGS. 14 and 15 are more detailed diagrams of the cell cycle shown in FIG. 13.
Figure 15:
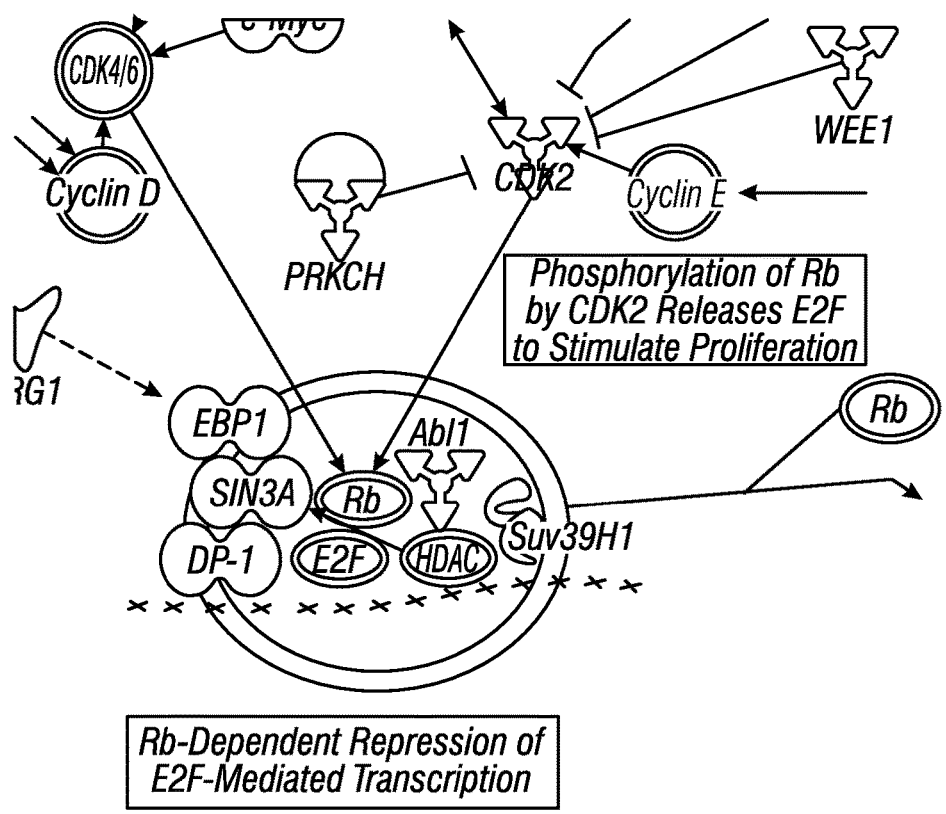

FIGS. 14 and 15, below, are more detailed views of the G1/S checkpoint pathway and the role of CDK2 in its regulation. Expression values and CN/LOH results from the tumor tissue (expressed as fold-change compared to control tissue) are overlaid in the diagram.

In this patient's tumor sample, there is an additional reason to suspect that CDK2 inhibition may be effective: CDK2 is normally deactivated by interaction with protein kinase C-eta (PKCeta; PRKCH; Kashiwagi, et al., 2000). The CN/LOH analysis of the tumor indicates that in the tumor sample PKCeta is deleted, suggesting that CDK2 may be permanently in its more active form. Thus, CDK2 is both transcriptionally up-regulated, and post-transcriptionally, is devoid of the deactivating influence of PKCeta. Thus, these data provide information that indicates the presence of CDK2 activity, a parameter not measured directly.

CDK2 activation leads to hyperproliferation via its phosphorylation of, and subsequent de-activation of retinoblastoma protein (Rb), a tumor suppressor. Active, de-phosphorylated Rb binds to the transcription factor E2F and prevents activation by E2F of genes necessary for cell cycle progression. Thus, phosphorylation of Rb by CDK2 prevents this cell cycle arrest by Rb. Although the mRNA levels of Rb and E2F are not up-regulated in the tumor sample, their activity is a function more of their phosphorylation state than transcription level. The up-regulation and chronic activation of CDK2 would produce a higher phosphorylation state and hence lower activity of Rb, and greater activity of E2F in promoting cell proliferation. As described above, in preclinical studies, melanoma cells are particularly vulnerable to CDK2 inhibition compared with normal tissues and other cancer cells (Tetsu and McCormick, 2003), which makes CDK2 a particularly attractive target. There are several CDK2 inhibitors in development, notably flavopiridol and CYC202, with trials ongoing for melanoma and other cancers.

Table 5 summarizes the evidence from the integrated expression and CN/LOH studies bearing on the hypothesis of CDK2 pathway dysregulation in the tumor. CDK2 was highly up-regulated and constitutes the strongest evidence. PRKCH is deleted, which also strongly supports the idea of CDK2 hyperactivity. We did not see up-regulation of Rb or E2F, however, we would not expect to, as these two pathway members are regulated by CDK2 at the level of protein functional activity, not transcriptionally. Thus, their expression levels are considered neutral, with respect to the CDK2 hypothesis. Indeed, we outline further studies below which could bear on the status of these proteins, and could potentially support or refute this hypothesis.

Second Hypothesis

Figure 16:
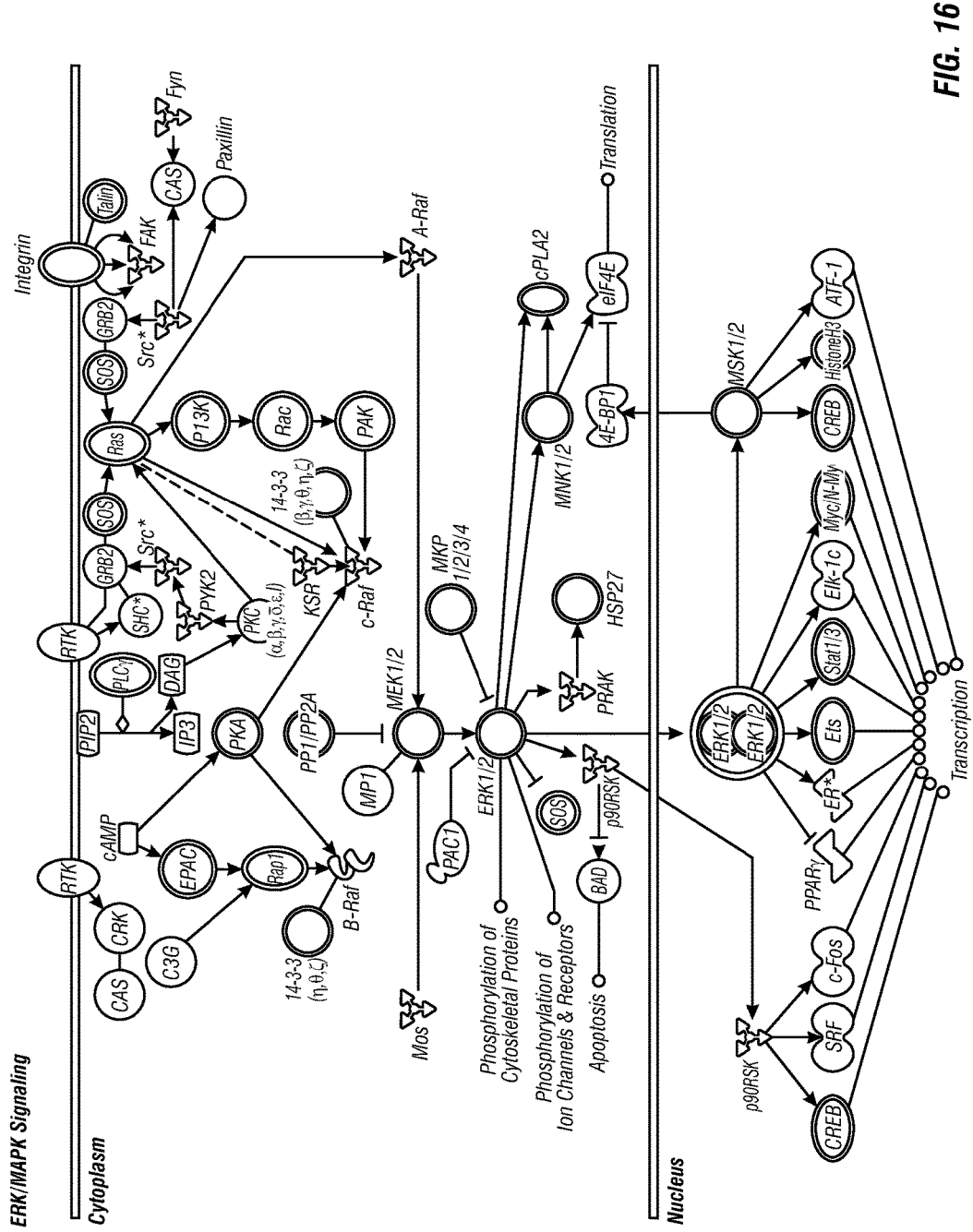
FIG. 16 is a diagram showing ERK-MAPK signaling and the role of Src.

V-src sarcoma viral oncogene homolog (SRC) a tyrosine kinase, is over-expressed in the tumor sample. SRC is a tyrosine kinase that is involved in several signaling pathways related to oncogenic processes and has been implicated in several cancers including melanoma. It plays a central role in modulating the ERK/MAPK pathway as shown below (FIG. 16), with gene expression and deletions overlaid. In this pathway, SRC potentiates the growth factor and/or integrin-mediated activation of RAS, with subsequent downstream activation of cell proliferation via the ERK/MAPK cascade (Bertotti, et al., 2006). There is a large body of literature establishing that the ERK/MAPK pathway is the major downstream effector of RAS dysregulation leading to oncogenic transformation. Thus, overexpression of SRC would be expected to amplify extracellular growth-related signals triggered by multiple growth factors or other ligands acting via receptor tyrosine kinases (RTKs), and thereby stimulate cell proliferation.

SRC is a molecular target of the drug dasatanib, which is a dual BCR-ABL kinase and Src family kinase inhibitor. It is currently approved for imatanib-resistant CML and treatment-resistant Ph+ ALL. It is also in clinical trials for metastatic melanoma.

Third Hypothesis

Figure 17:
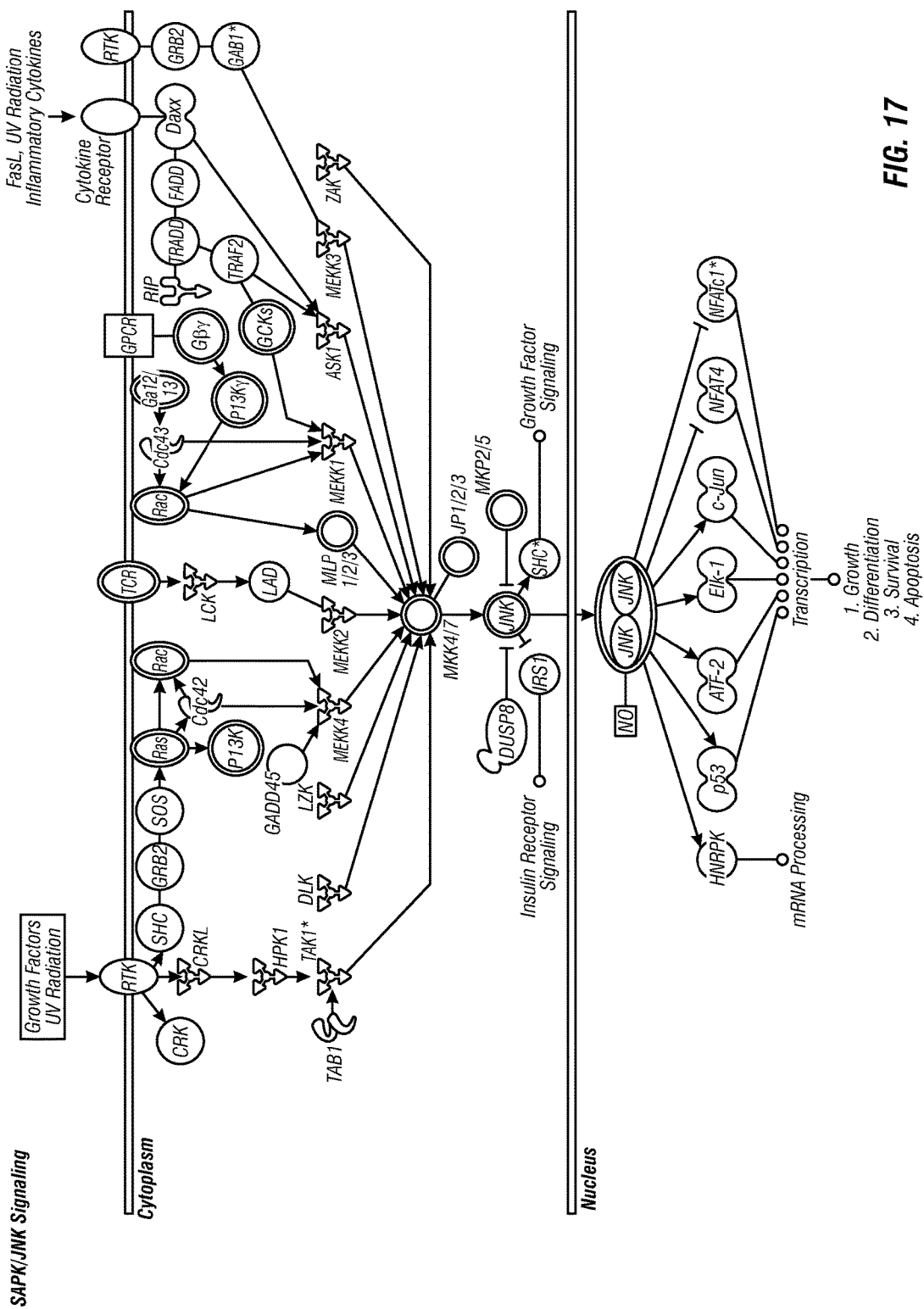
FIG. 17 is a diagram of SAPK/JNK signaling showing the role of LCK.

LCK, a member of the Src tyrosine kinase family, is normally expressed in T-lymphocytes and is a target of leukemia drugs. However, it has also been investigated as a melanoma target, and recently the inhibitor dasatanib (approved for use in CML and ALL) has been shown to induce cell cycle arrest and apoptosis, and inhibit migration and invasion of melanoma cells (Eustace, et al., 2008). The central role of LCK in the SAP/JNK pathway and the expression and deletion status of several other pathway members, indicating dysregulation of this pathway, is shown in FIG. 17. LCK activation may influence cell proliferation via activation of MEKK2, with subsequent activation of JNK. JNK has been shown to have both proliferation and pro-apoptotic effects depending on cell type and context.

For the SAP/JNK pathway, algorithm 1a gives probability of pattern being produced by chance $(\Pi)=0.02$.

The total pathway elements $(q)=11$, which are LCK, 1 upstream (TCR), 2 intermediaries before JNK (MEKK2, MKK4/7), JNK, 6 downstream of JNK (p53, AFT-2, Elk-1, c-Jun, NFAT4, NFATc1). The total aberrant genes consistent with hypothesis $(n)=5$, which are LCK, 1 upstream (TCR), 1 intermediaries before JNK (MEKK2), JNK, 1 downstream of JNK (c-Jun). The total number of possible pathways (N): Assume ~200 based on XXX canonical pathways within Ingenuity and the cut-off probability $(p)=0.05$.

Concurrent inhibition of LCK and SRC might be expected to enhanced efficacy given the over-expression of both these targets in the tumor tissue, and their involvement in different but complementary pathways involved in oncogenesis and tumor maintenance. It should be noted, however, that because of its role in T-cell activation, inhibition of LCK could possibly have an immunosuppressant effect.

Our current technology collection is relatively insensitive to the types of measures that would evaluate immunotherapy as a potential recommendation. While we address biological questions about the tumor itself, more information either about systemic immune function, or specific populations of tumor-associated T-cells would be necessary to address this option. We are currently investigating the feasibility of adding this capability at a later date.

Additional Insight

We did however note a finding which, in hindsight, may be consistent with the patient's successful response to immunotherapy. In the tumor sample, the gene for Complement factor H (CFH) is deleted. CFH is a protein that regulates complement activation and restricts complement-mediated cytotoxicity to microbial infections. There is literature demonstrating that down-regulation of CFH in cancer cells sensitizes them to complement attack which can inhibit their growth in vitro and in vivo (Ajona, et al., 2007). To the extent that the patient's response to anti-CTLA4 therapy is related to a complement-mediated component of the immune response, the deletion of CFH might be a predictor of this vulnerability of the tumor.

Summary

Several dysregulated pathways with possible connections to melanoma were found: Cyclin-dependent kinase 2 (CDK2; inhibited by several drugs currently in development, including flavopiridol and CYC202), v-src sarcoma viral oncogene homolog (SRC), and lymphocyte-specific protein tyrosine kinase (LCK; both inhibited by the approved drug dasatanib). These targets all play roles in cancer-related signaling pathways, and have been specifically linked in the literature to melanoma progression. Additionally, deletion of the CFH gene, which can sensitize cells to complement attack, could possibly help explain the vulnerability of the tumor to immunotherapy.

Two drugs, flavopiridol and CYC202, targeting CDK2 are currently in clinical trials for melanoma and other cancers. Dasatanib, which targets both SRC and LCK, is approved for several leukemias, and is also in clinical trials for melanoma. Thus, while the first hypothesis (CDK2 pathway) is scientifically stronger, the key drugs that target the pathway are still in clinical trials. The pathways in the second two hypotheses (SRC and LCK) may be more easily targeted by an already approved drug.

The following steps are taken further to validate these hypotheses:

Elucidation of CDK2 pathway dysregulation at the protein level to determine the activation state of CDK2 and Rb as assessed by phosphorylation status. Thus, immunohistochemistry of tumor sections and control tissue using phospho-specific antibodies to CDK2 (Thr160) and Rb (Thr821), is performed as hypophosphorylation of CDK2 and hyperphosphorylation of Rb would support the validation of CDK2 as a target.

Elucidation of SRC pathway dysregulation at the protein level to determine if downstream effectors of SRC are hyper-activated. Thus, immunohistochemistry of tumor sections and control tissue using phospho-specific antibodies to ERK1/2, downstream effectors of SRC with respect to cell growth and proliferation, is performed as hyperphosphorylation of ERK1/2 indicates over-activation by SRC and supports the validation of SRC as a target.

Elucidation of LCK pathway dysregulation at the protein level to determine if downstream effectors of LCK are hyper-activated. Thus, immunohistochemistry of tumor sections and control tissue is performed using phospho-specific antibodies to JNK1/2/3, downstream effectors of LCK with respect to cell growth and proliferation, as hyperphosphorylation of JNK1/2/3 indicates over-activation by LCK and supports the validation of LCK as a target.

In vitro validation of the CDK2, SRC, and LCK hypotheses is performed using a cell line derived from tumor. Tumor cells from a fresh sample of tumor tissue are cultured and maintained in vitro, followed by treatment with CDK2 inhibitors, or dasatanib (SRC/LCK inhibitor), to assess anti-proliferative effects of these agents. Measured endpoints are cell proliferation (using, e.g., ATP charge) and apoptosis (using one of several readily available assays).

In vivo validation of the CDK2, SRC, and LCK hypotheses is performed using xenograft models, such as a mouse xenograft model derived from cultured tumor cells (described above). This model is used to test CDK2 inhibitors and dasatanib for anti-tumor effects, using change in tumor size as the measured endpoint.

These are the complete networks of interacting genes generated from the filtered list of up- and down-regulated genes. The Score column represents the overall level of interconnectedness within each network, and the Top Functions column describes cellular functions that are over-represented (relative to chance) in each network, as determined by the individual annotation of each gene in the network.

TABLE 4

Regulated Networks from Melanoma Tumor Sample

| ID | Molecules in Network | Score | Focus Molecules | Top Functions |
|---|---|---|---|---|
| 1 | ADPRH, C11ORF67, C19ORF42, C1ORF163, C4ORF19, C6ORF123, C6ORF208, CCDC115, CRYZL1, DDX47, HBS1L, HMGN4, HNF4A, INTS4, JTB, KIAA0409, MLF1IP, MRPL22, MRPL53, MRPS35, MRPS18C, PPP2R3C, SLC26A1, SLC7A6OS, SNX11, SPATA6, STARD7, TAPBPL, TBC1D16, TIGD6, TMEM79, TMEM63A, TRIM4, TXNDC14, ZSCAN18 | 32 | 35 | Molecular Transport, Cellular Development, Lipid Metabolism |
| 2 | ADNP, ASNS, BRD3, C19ORF12, CALCRL, CDH11, CDH16, CSH1, DYNC1H1, FADS3, FGF10, FMO2, GPR6, GPR56, GTPBP4, HOXA7, HPGD, LMO7, LOXL2, MAP7, MSI2, NADSYN1, NOTCH2NL, PSG4, PSG9, PTPN12, RBM33, S100A13, SMARCA4, ST6GALNAC4, TBX5, TEX10, TMEM123, WWTR1, ZNF143 | 32 | 35 | Reproductive System Development and Function, Gene Expression, Cancer |
| 3 | ANAPC1, BAT1, C3ORF26, CCNC, DCD, DDX52, DICER1, DIMT1L, EXOC4, HDAC6, HNRNPM, HNRPLL, LMNA, LSM11, MED6, MED12, MED13, MED16, MED17, MED22, MED25, MED31, MYBBP1A, NOC4L, NONO, PPIG, PTBP1, RAB25, RBM39, RPS15A, SFRS3, SMC4, SNRPD1, TOR1AIP1, UBTF | 32 | 35 | Gene Expression, Cell Signaling, RNA Post-Transcriptional Modification |
| 4 | C10ORF54, C11ORF58, CCND2, CIAPIN1, CREM, DAD1, DDT, DHRS1, EIF3M, ETFB, EWSR1, FAM49B, FBXL18, GLRX3, HDAC3, HPRT1, IKBKE, KIAA1683, MRPS18B, MTPN, NSUN4, PDIA6, PLSCR1, PPIB, PTRH2, RAB37, RHOB, RPL22, SPCS2, SPG7, TMEM111, TMSB4Y, TNFRSF14, ZNF638, ZNF764 | 32 | 35 | Gene Expression, Cancer, Cell Cycle |
| 5 | ALOX15B, CRKRS, DDX17, ELOVL1, FIP1L1, FMN1, FNBP4, FUS, HIST1H1C, HNRNPA1, HNRNPA2B1, KRT31, MYBPH, MYEF2, NES, P38 MAPK, PLEKHB2, PRPF40A, RNPS1, SF1, SFPQ, SFRS1, SFRS2, SFRS4, SFRS6, SFRS9, SFRS10, SFRS2IP, SNRPA1, SRPK1, TOP1, TWF1, U2AF1, ZFHX3, ZFR | 29 | 34 | RNA Post-Transcriptional Modification, Lipid Metabolism, Small Molecule Biochemistry |
| 6 | ABI2, ADAM22, ANXA11, BCOR, BPTF, C17ORF59, CBLC, CCKAR, CEP290, CHMP7, CHMP4B, CHST12, CPNE4, HNRNPH3, Mapk, MAZ, NDE1, OLIG2, PCGF1, PCM1, PCNT, PDCD6, PLSCR3, PTPN23, PTPRH, SH3KBP1, SMARCA1, SNX13, SRI, TPM2, TRIB1, TUBGCP2, UGCGL1, UGCGL2, WISP1 | 29 | 34 | Cellular Assembly and Organization, Cellular Development, Cellular Growth and Proliferation |

TABLE 4-continued

Regulated Networks from Melanoma Tumor Sample

| ID | Molecules in Network | Score | Focus Molecules | Top Functions |
|---|---|---|---|---|
| 7 | APPBP2, C21ORF113, CRABP1, CUL4B, DDIT4, DECR1, DLGAP1, DSCR3, ESR1, GRWD1, HMGN1, IQWD1, JAG2, LDLRAP1, LRP2, MFAP5, NR2C1, NR2C2, NR2C2AP, NRIP2, PRDM2, Rbp, RBP2, RBP7, RORB, SMU1, SORBS2, SYNJ2, SYNJ2BP, TAF1B, TCF7, UMODL1, WDR26, WDR61, WWC1 | 29 | 34 | Gene Expression, Cellular Assembly and Organization, Lipid Metabolism |
| 8 | BCCIP, C1ORF94, CCNA2, CCNB1, CCNB2, CCNF, CDC2, CDC25A, CDCA3, CDK2, CDKN3, CHML, Cyclin B, DNM1L, FOXM1, GOLGA2, GORASP1, GORASP2, KLK4, MAP4, MXI1, PAPOLA, PSENEN, PTMA, RAB1A, RNF17, SKI, TMED2, TMED3, TMED10, UBE2A, UBR3, USO1, WEE1, ZNF593 | 29 | 34 | Cell Cycle, Cancer, Reproductive System Disease |
| 9 | ACVR1B, ALAD, CCT2, CCT4, CCT7, CCT8, DKC1, DLX1, EEF1G, FEN1, HARS, INHBC, INSR, KLF9, LZTS1, NARG1, NAT5, NOLA1, Pseudouridylate synthase, RAD1, RAD51AP1 RAD9B, RPUSD2, SEPP1, SEZ6L2, SFRS5, SIX4, SMURF1, SNX1, SSR1, TRUB1, TXNDC9, ULK2, VPS35, ZFAND5 | 29 | 34 | Carbohydrate Metabolism, Genetic Disorder, Hematological Disease |
| 10 | AKNA, ASF1A, ATRX, C19ORF50, CBX5, CHAF1A, CYBB, DNMT3A, EDN3, EXOC5, EXOC7, GIGYF2, Hdac, HOXA10, ITGB3, KCNQ1OT1, LAMA4, MBD2, MOBKL1B, MYO10, MYT1, NCF1, NR4A3, NSL1, PAX7, RBBP4, SNRPC, SNRPN, SRP9, SUZ12, TCEB3B, TLK1, TLK2, TRIM52, ZC4H2 | 29 | 34 | Cell Cycle, Cellular Assembly and Organization, DNA Replication, Recombination, and Repair |
| 11 | APIP, ATG7, C1QBP, C1QTNF5, COIL, DCTD, DHX16, FAM115A, FAM176A, GIPC2, GSPT1, HERC3, IMPDH2, INO80C, KPNA3, LNX1, MAP1LC3A, MGEA5, NUMBL, PAICS, PIAS4, PREPL, Proteasome, PTN, PTPRZ1, RNF112, SAT1, SDC3, SHMT2, SLC25A36, TAC3, TAF1D, TNFRS F10D, WFDC2, ZNF277 | 29 | 34 | Hematological System Development and Function, Hematopoiesis, Organismal Development |
| 12 | AKR1C1, COPS6, COPS8, COPS7A, COPS7B, CUGBP1, CUL4A, DIS3L2, DPYSL3, DYNLRB1, eIF, EIF5, EIF1AX, eIF2B, EIF2B1, EIF2S1, EIF2S3, EIF3A, EIF3E, EIF3G, EIF3K, EIF4A2, EIF4B, EIF4G3, EIF5B, HAPLN1, IGF1, IMPACT, MBNL1, MPHOSPH6, NCBP2, PARN, RPS2, SGK3, VPRBP | 27 | 33 | Protein Synthesis, Gene Expression, RNA Trafficking |
| 13 | ACE2, Angiotensin II receptor type 1, ANGPT2, APLN, APLNR, CBFA2T2, CCL14, CRYBB3, GART, HEXIM1, HIF3A, HSD17B14, HTATIP2, ICA1, Integrin alpha 2 beta 1, KLHL20, MELK, MKKS, NUP133, PTGER3, PTGS1, RASGRP3, RPIA, SNRK, STARD8, STC1, STK16, SYNM, TBC1D8, TMSB10, TNPO2, VASH1, VEGFA, WDYHV1, ZNF124 | 27 | 33 | Cardiovascular Disease, Genetic Disorder, Cardiovascular System Development and Function |
| 14 | ACP5, CCDC67, Ctbp, CYP17, DDX3X, DEFA4, FAM120C, HNRNPU, IFIT3, IKZF1, IKZF4, LPCAT1, LRCH4, MC2R, MRAP, NCOR2, NR6A1, NUFIP2, NUP50, OGDH, OGT, PCSK1N, PEX5L, PML, POMC, RBAK, RREB1, SART1, SEH1L, SNW1, TRAK1, TSR1, ZC3HAV1, ZNF462, ZNF687 | 27 | 33 | Endocrine System Disorders, Genetic Disorder, Infectious Disease |
| 15 | ACE, ADRA2B, AGTR1, AGTR2, ANTXR2, BCLAF1, CLNS1A, DRD2, FREQ, Gi-coupled receptor, GRM8, HMGB1 (includes EG: 3146), HNRNPA3, HTR1D, IPO9, KCNAB1, KCND2, KCNE4, KCNIP2, KCNIP4, KCNJ1, KCNQ1, LRP4, MTUS1, NKTR, OPRM1, Pka, PPP1R9A, PPP1R9B, RPL19, RPS7, RPS19, SNPH, TNP2, WWP2 | 27 | 33 | Cardiovascular System Development and Function, Cardiac Arrhythmia, Cardiovascular Disease |
| 16 | 14-3-3(β, γ, θ, η, ζ), AHI1, ASCL2, BUB1B, CADM1, CALM3, CEP152, CRTAM, CTPS, CTSD, EMP3, EPB41L3, FRMD6, HECTD1, Hsp90, ICK, LARP1, LYST, MLXIP, NLRP1, NLRP3, P2RX7, PIH1D1, PLEKHF1, PPFIBP1, PRMT5, RPAP3, SLC4A7, SMYD2, SNCG, SSH1, SSH2, WDR77, YWHAB, YWHAG | 27 | 33 | Cell Morphology, Cellular Compromise, Molecular Transport |
| 17 | ANPEP, ATP1B1, ATP1B3, BASP1, BCAM, BMP1, CCDC80, CDH17, CDX2, CHRD, COL5A2, CTSLL3, Cyclin A, Cyclin E, DMP1, FAH, FOXC1, GZMK, HOXC10, KIAA1274, KRAS, LAMA2, LAMA5, LAMC2, LGALS3, MYBL2, NRN1, PBX2, RAB20, TBX1, TFDP1, TLL2, TPM3, VAPA, YLPM1 | 27 | 33 | Organismal Development, Cell Morphology, Skeletal and Muscular System Development and Function |
| 18 | ABCC1, ACHE, ACLY, ARNTL, BHLHB3, CLMN, DAO, ELA2, ENPP2, FOSL2, FOXA2, FXR1, GABPA, GCK, GMFB, GPAM, GPR146, HECW2, Hexokinase, HN1, IER3, MYOD1, NAP1L3, NOV, ONECUT2, PROC, SDC1, Sod, SOD1, SOD2, STAB2, TAT, THBS1, TMC1, TP73 | 27 | 33 | Cellular Compromise, Lipid Metabolism, Molecular Transport |
| 19 | Adaptor protein 1, AP1G1, AP1GBP1, AP1S1, AP1S2, ARCN1, ARMC6, BICD1, COP I, COPB1, COPB2, COPE, COPG2, CPE, CXCL14, DNASE1, GGA1, GGA3, GUSB, Hdac1/2, IL8, ING1, KIF13A, LAT2, LPAR3, M6PR, PACS2, PIGR, POLDIP2, PTGER1, SAP30, SCAMP1, STK36, TFF3, VANGL1 | 25 | 32 | Cellular Assembly and Organization, Cell Morphology, Cell-To-Cell Signaling and Interaction |

TABLE 4-continued

Regulated Networks from Melanoma Tumor Sample

| ID | Molecules in Network | Score | Focus Molecules | Top Functions |
|---|---|---|---|---|
| 20 | ADARB1, AKR7A2, BAT2, CCNO, CDC2L2, Cpsf, CPSF1, CPSF2, CTH, DCBLD2, ELOVL2, GREM1, GTF2I, HDAC10, HMG CoA synthase, HMGCS1, HSD3B7, IARS, MAGEA6, NUDT21, OMD, PDGF BB, PSMF1, QARS, RPL13, SBDS, SFRS7, SNTG1, SPTBN5, SRPRB, SSR3, SYMPK, SYNE1, TRIOBP, VAPB | 25 | 32 | RNA Post-Transcriptional Modification, Cell Death, Embryonic Development |
| 21 | AMH, CHM, CXCL2, ERC1, GDF9, LDL, MYO5A, NPC2, OSBPL6, PON2, PPFIA4, PRPS1, PTP4A2, Rab5, RAB22A, RAB27A, RAB27B, RAB4A, RAB6A, RABAC1, RABGGTB, Ribose-phosphate diphosphokinase, RPH3A, SNCB, SPTG21, ST14, STAR, SYP, SYTL2, SYTL5, TNFAIP6, TRIM2, TRIM3, UBE2K, ZFYVE20 | 25 | 32 | Cellular Assembly and Organization, Hair and Skin Development and Function, Organ Morphology |
| 22 | ABCB6, ANKHD1, APOD, ARAP1, ASXL1, BAZ2A, C5ORF34, CBX2, CRK/CRKL, DOCK1, DOT1L, DYRK3, EHMT1, ELP4, GRINL1A, Histone h3, Histone-lysine N-methyltransferase, HOXC5, JMJD6, MLL3, PARP10, PCGF2, PHC2, PHC3, RNF2, RPS9, RYBP, SCMH1, SRRM2, SYNE2, TFCP2, TM4SF18, TMEM70, XIST, ZDHHC11 | 25 | 32 | Embryonic Development, Tissue Development, Gene Expression |
| 23 | ATM, Basc, BCL11A, CDYL, COL19A1, COL9A2, COL9A3, DUSP26, EHF, EIF2AK3, FBXL11, GINS2, HDAC2, HDAC4, HDAC9, HLA-DRA, HMGB3, HSF4, Hsp70, LIG4, MDC1, MED23, Mre11, MRE11A, NBN, PDS5A, POT1, SMC3, SMC1A, TERF1, TFDP2, TP53BP1, WAPAL, XRCC5, YY1 | 25 | 32 | DNA Replication, Recombination, and Repair, Cellular Development, Hematological System Development and Function |
| 24 | ADCY10, Ant, ATF7IP, CBR1, CDT1, CKMT1B, DBN1, DTL, ERCC8, GTF2H2, GTF2H3, GUCA1A, GUCY, hCG, HTRA2, KIF5B, NIPBL, NPR1, NPR2, ODF2L, OPA1, PNOC, PPID, PRSS23, S100B, SLC25A4, SLC25A6, SLC25A13, SLC4A4, SVEP1, TMEM158, TRAPPC4, TTC3, VDAC1, ZNF518A | 25 | 32 | Cellular Assembly and Organization, Nucleic Acid Metabolism, Small Molecule Biochemistry |
| 25 | AURKA, AURKB, BTRC, CAPRIN1, CELSR2, CKAP5, CSTF3, DTYMK, E3 co-factor, FZR1, G3BP1, ID4, IDI1, KLF6, KPNA1, KRT4, LRRFIP1, PFKL, PFKM, PINK1, PTEN, PTPRN2, RAB10, RNASEH1, RRM1, RRM2, Scf, SEL1L, SERPINH1, SKP2, SMOX, SORD, TACC1, TCF12, TNFAIP1 | 25 | 33 | Cancer, Renal and Urological Disease, Nucleic Acid Metabolism |
| 26 | ANLN, ARL6IP1, ASPM, ATAD2, ATM/ATR, BLZF1, BRCC3, C14ORF106, CDC14A, CKAP2, CPOX, CTSF, EEF1E1, FIGNL1, FXYD3, HUWE1, MAGEA2, NUP85, PIGF, PIGG, PPA1, PPP4R2, PRKRIR, RCHY1, SLC19A2, SLC6A6, SNAPC5, TCN2, TEAD2, TFAM, TMEM97, TNFRSF10C, TP53, TULP4, UBA6 | 24 | 34 | Cancer, Cell Cycle, Gastrointestinal Disease |
| 27 | ADAP1, Adaptor protein 2, AGXT, AHNAK, APOBEC3C, CACNB2, CACYBP, CNBP, GABAR-A, GABRA5, GABRB3, GABRE, GABRG1, GABRG3, GABRP, GABRQ, GABRR1, GNE, GPHN, HNRNPAB, HNRNPR, IGF2BP1, KIAA1549, LAMP1, P2RX2, P2RX6, Pkc(s), PRKRA, RIF1, RPL35A, S100A12, SYNCRIP, SYT3, SYT7, TBL1X | 24 | 32 | Neurological Disease, Developmental Disorder, Psychological Disorders |
| 28 | ARIH1, CARD14, CDH22, DOK5, EDA, ETS, ICOSLG, IL1RL2, LINGO1, LTB, Lymphotoxin-alpha 1/beta 2, NFkB, NOL14, PLEC1, POU2AF1, RAB3C, RBCK1, RNF216, RNF144B, RNF19B, SDS, SIAH2, SLC11A2, SLC37A4, SPIB, STK10, TNFRSF19, TNFRSF13C, TRIM9, UBE2, UBE2C, UBE2L6, UBE2V1, WNT6, WNT10A | 24 | 31 | Humoral Immune Response, Lymphoid Tissue Structure and Development, Post-Translational Modification |
| 29 | AP4M1, AXIN2, BBX, Bcl9-Cbp/p300-Ctnnb1-Lef/Tcf, CBFB, CCL18, CD6, CD58, CD3EAP, CLEC7A, DEF6, ELAVL4, EOMES, Groucho, HIPK2, IL4, LAMP2, LEF1, LEF/TCF, Mhc ii, MVK, NFATC2IP, NKX3-1, PKIB, PTCH1, RUNX3, SLC26A2, SPDEF, SYT11, TBC1D17, TCF7L1, TLE4, TMEM131, TRA@, VTCN1 | 24 | 31 | Cell-mediated Immune Response, Hematological System Development and Function, Immune Cell Trafficking |
| 30 | ACAP1, CCL19, CCL21, CDC16, COL8A1, CSF2, Csf2ra-Csf2rb, CSF2RB, CUL3, DDX5, DDX54, EP400, EPC1, ESR2, Esr1-Esr1-estrogen-estrogen, ESRRB, EXOSC3, HNRNPD, HOOK1, ILF3, ING3, IRAK3, KHSRP, KLHL12, MAD2L1, NACC1, NR0B1, PRMT2, Rab11, RBM17, SNX20, TIA1, TIAL1, TRAP/Media, TRRAP | 24 | 31 | Antigen Presentation, Cellular Movement, Hematological System Development and Function |
| 31 | APLP2, C7ORF64, C9ORF100, CNTN1, DAZ4, DZIP1, ERK1/2, GLYAT, HN1L, ID2, KIAA0182, LRRC41, MFNG, Notch, NOTCH2, NOVA2, NRCAM, PDLIM4, POU2F2, PSEN2, PTBP2, QKI, RBPMS, RCOR3, Secretase gamma, SLC5A7, Smad1/5/8, SMUG1, STRBP, TIE1, TNR, USH1C, USH1G, XRCC6, XRCC6BP1 | 24 | 31 | Genetic Disorder, Neurological Disease, Molecular Transport |

TABLE 4-continued

Regulated Networks from Melanoma Tumor Sample

| ID | Molecules in Network | Score | Focus Molecules | Top Functions |
|---|---|---|---|---|
| 32 | ANKRD44, BAP1, Cbp/p300, CYP19A1, DUB, ENO1, GATA4, LHX9, MUC4, NR5A1, SMAD2, Sox, SOX1, SOX3, SOX11, SOX12, SOX15, TBC1D1, TBX18, UCHL1, UCHL5, Unspecific monooxygenase, USP3, USP6, USP10, USP14, USP25, USP31, USP32, USP42, USP46, USP48, USP53, ZNF653, ZNHIT6 | 24 | 31 | Organ Development, Reproductive System Development and Function, Cancer |
| 33 | CLN6, COL1A1, FLT1, FLT4, GIGYF1, GTF3A, IFI6, IFNGR2, IL20, IL23, IL12RB1, IL13RA2, IL31RA, IL8RB, NPY2R, NRP1, NRP2, OMP, PAIP2, PEG10, PLXNA3, PRELP, RGS12, Sema3, SEMA3B, SEMA3G, SOCS7, STAT3, TMF1, TMPRSS6, Vegf, Vegf Receptor, ZBTB10, ZNF197, ZNF467 | 23 | 31 | Cellular Movement, Cell-To-Cell Signaling and Interaction, Cardiac Hemorrhaging |
| 34 | ABCC9, Ahr-aryl hydrocarbon-Arnt, ALDOA, B4GALT5, CSE1L, EEF2, Esr1-Estrogen-Sp1, FAM120A, HSP90AB1, HSPH1, KLF15, L-l actate dehydrogenase, LDHA, LDHB, LDHC, MIER1, NFIA, NFIC, Nuclear factor 1, NUMA1, PKLR, PKM2, POGZ, PSAT1, RPL5, RPL7, RPS3A, RPSA, SFTPC, SFXN3, SLC11A1, SP1, TRIP12, XPO1, ZCCHC14 | 22 | 31 | Carbohydrate Metabolism, Gene Expression, Cardiovascular System Development and Function |
| 35 | ARID1A, ATF7, BATF, BATF3, BAZ1B, CEBPE, CSTA, CYSLTR1, CYSLTR2, EPB49, EVI1, FTH1, GATA1, GC-GCR dimer, HHEX, HIVEP3, Jnk dimer, JUN, JUN/JUNB/JUND, JUND, MAFF, MLLT6, MT2A, MTF1, NFE2L1, NRAP, PRRX1, PXDN, SMARCA2, SMARCC1, SMARCD1, SRGAP3, SWI-SNF, Tcf 1/3/4, TMC8 | 22 | 30 | Gene Expression, Cellular Growth and Proliferation, Hematological System Development and Function |
| 36 | ATP5B, CKAP4, CTNNA1, DNAH1, DNAJ, DNAJA1, DNAJA2, DNAJB11, DNAJC, DNAJC4, DNAJC10, DNAJC5G, Gα q, GOT2, GPRIN2, HSP, Hsp22/Hsp40/Hsp90, HSP90AA1, HSPA5, HSPA8, HSPA9, KPNB1, KRT17, MAP3K7IP1, NFE2L2, PITPNM3, PTK2B, SFN, SIL1, SYNPO2, TNPO1, TRIM29, TUBB, TXN, XPO7 | 22 | 30 | Post-Translational Modification, Protein Folding, Cellular Function and Maintenance |
| 37 | 14-3-3, ARHGEF16, C12ORF51, CBLL1, CBY1, CD74, Cofilin, FAM62A, HAT1, HLA-DPB1, HLA-DRB4, HMG20B, KIAA1429, MDM4, MHC II-β, Mhc2 Alpha, MYST3, MYST4, PABPN1, PANK2, PAPOLG, REEP6, RPL4, RPLP2, SH3BP4, SSBP1, STRAP, SUPT6H, TACC2, TPI1, TUBA4A, TUBB1, TUBB4, Tubulin, YWHAZ | 22 | 30 | Cancer, Reproductive System Disease, Neurological Disease |
| 38 | ADA, BIN1, C4A, DDX1, DMC1, Dynamin, E2f, ENG, FKBP3, FMNL1, FOLR1, GOLT1B, HMOX1, IPO5, MCM5, MND1, NADPH oxidase, OBSL1, PFN1, Pld, PLD1, PRDX6, RAD51, RAD51C, RAD51L1, RALA, RANBP2, RIN3, RPS16, SERBP1, SNCA, SYN2, TMEM126B, TYMS, tyrosine kinase | 22 | 30 | Cell Cycle, DNA Replication, Recombination, and Repair, Cell Morphology |
| 39 | ACP1, ADAM12, AFAP1L2, ANKRD11, CRLF2, DDR2, DGKA, DIAPH3, EPHA4, EPHA/B, Ephb, EPHB2, Ephb dimer, EPOR dimer, esr1/esr2, GPR172B, KBTBD2, KCNQ4, KDELR1, NCK, NCKIPSD, NEU2, PIP, PTPN13, PTPN21, SDC2, SERINC3, SH2D3C, SH3PXD2A, SKAP2, SLC16A1, SRC, TNS1, WBP5, WWOX | 20 | 29 | Cell Morphology, Cell-To-Cell Signaling and Interaction, Cellular Assembly and Organization |
| 40 | ALK, ARHGEF15, BRAP, BRD7, C11ORF49, CENPF, CHKA, CTBP2, EFNA5, ENaC, EPHA, EPHA1, EPHA10, EPHB4, H19, IGF2BP3, IRS, ITPR3, KRT74, MAPK8IP3, MARK1, MPRIP, NEFL, Pdgfra-Pdgfrb, PDLIM5, PI3K, PIK3AP1, PIK3R2, RAP1B, RGL3, Rock, SCN7A, SCNN1B, SHC3, SLC12A4 | 20 | 29 | Cancer, Cell Cycle, Cell Morphology |
| 41 | ADRA1B, ARMC2, CHMP4C, CLU, CP, Cyclooxygenase, FPR1, FPR2, GJC2, HDL, HMGA2, HPSE, IGHG1, IGKC, IL1, Interferon beta, KIAA1409, KLK3, KRT7, KRT14, KRT16, MOCOS, Neurotrophin, PAPPA, PKHD1, PNMA2, SAA1, SAA4, SAA@, SCAF1, SLC2A3, SORCS1, SORT1, SPEF2, TTPAL | 20 | 29 | Cancer, Reproductive System Disease, Free Radical Scavenging |
| 42 | ATF6, BEX2, CALR, CCR4, CD8, CREBL1, ERO1L, GATA3, GOT, GZMA, HIST1H1T, HLA-E, HMGB2, HSP90B1, Ige, IL12, IL33, IL1RAP, IL1RL1, ITM2A, LMO2, MHC Class I, NASP, NHLH2, P4HB, PDIA2, PDIA3, PDIA4, PHOX2A, POU3F1, SET, TAL2, Tap, TNFRSF25, TTLL5 | 20 | 29 | Hematological Disease, Immunological Disease, Infectious Disease |
| 43 | ACTR2, ACTR3, ACTR1A, ACTR3B, AIF1, Arp2/3, ARPC5, CDC42EP4, CFL2, CIAO1, CLCN3, CYFIP1, DIXDC1, FCGR1A/2A/3A, G-Actin, GIT2, GNL3, GOLM1, IQUB, KIAA1967, MYLK3, MYO1D, NCKAP1, NWASP, PAK1, PCDH7, PGAM1, Rac, RPL13A, TMEM33, TNFSF11, TROVE2, WAS, WASP, WIPF1 | 20 | 29 | Cell-To-Cell Signaling and Interaction, Cellular Assembly and Organization, Skeletal and Muscular System Development and Function |

TABLE 4-continued

Regulated Networks from Melanoma Tumor Sample

| ID | Molecules in Network | Score | Focus Molecules | Top Functions |
|---|---|---|---|---|
| 44 | adenylate kinase, AK2, AK7, AK3L1, Alcohol group accept or phosphotransferase, ATYPICAL PROTEIN KINASE C, CDK6, CDK4/6, COQ7, DMPK, DYRK1A, FBXO7, HIPK1, HSPE1, IRAK1, MAP2K2, MAP2K5, Map3k, MAP3K7, MAPK6, MAPK11, PAK2, PDK1, PDPK1, PKN2, PLK3, PPT1, PRKCH, PRPF4B, RPL29, Rsk, RTCD1, SH3RF3, TOMM70A, WDR68 | 20 | 29 | Amino Acid Metabolism, Post-Translational Modification, Small Molecule Biochemistry |
| 45 | 3 BETA HSD, BRF2, C2ORF47, CLEC11A, DCP2, EML4, Fcer1, HIGD1A, HSD17B11, LRPPRC, Mek, MTR, NADH dehydrogenase, NADH2 dehydrogenase, NADH2 dehydrogenase (ubiquinone), NDUFA1, NDUFA2, NDUFA4, NDUFA7, NDUFA8, NDUFA12, NDUFA13, NDUFB2, NDUFB9, NDUFB11, NDUFS1, NDUFS3, NDUFS8, NEK6, OTUD4, PTPLAD1, SFXN4, STARD9, TSC22D1, UHRF1BP1 | 20 | 29 | Free Radical Scavenging, Genetic Disorder, Neurological Disease |
| 46 | Alpha Actinin, BDNF, Calpain, CAPN6, CAPN10, CD37, CHRNA5, CHRNB2, Clathrin protein, CLTB, CTSS, CXCL10, EPN1, EPS15, EPS15L1, GAD, HLA-DQB1, JARID2, LBP, LDB3, MBP, MHC Class II, MYOZ2, MYOZ3, Nicotinic acetylcholine receptor, NTRK2, PEG3, PICALM, PTPN1, RFXAP, RPS21, SCN5A, SCT, SNAP91, VIPR1 | 20 | 29 | Cellular Assembly and Organization, Cellular Function and Maintenance, Cellular Movement |
| 47 | ADCY, ADRA1A, ADRB2, ADRB3, Beta Arrestin, BRS3, C18ORF25, CFTR, CRHR1, CXCR4, DIO2, DZIP3, Galphai, G-protein beta, GNA11, GNA12, GNA13, GNAQ, GNAS, GNB1, GNB1L, Gs-coupled receptor, HAX1, HGS, HTR6, KCNK1, PLC, PLCD3, PLEKHA6, UBE2E1, UBE2G1, UBE2I, UBE2J1, WSB1, XPNPEP3 | 20 | 29 | Cell Signaling, Nucleic Acid Metabolism, Small Molecule Biochemistry |
| 48 | C19ORF2, CCNT2, CDK9, DNA-directed DNA polymerase, DNA-directed RNA polymerase, E3 RING, HLA-DQA1, HTATSF1, MDM2, MYCN, NCL, PCNA, POLE, POLE4, POLH, POLR1D, POLR2E, POLR2J2, POLR2K, POLR3C, POLR3E, POLR3G, POLR3H, PRIM2, RAD18, RAD52, REV1, RFC3, RPA, RPL10, RPL37, RPS8, SSB, STK19, TFAP4 | 20 | 31 | DNA Replication, Recombination, and Repair, Gene Expression, Cell Cycle |
| 49 | ALP, ALPI, ALPL, ARHGEF5, BCL2L11, Bmpr1, BMPR2, CAP, CASP2, CRYM, DLX2, DLX4, DUSP14, FOXG1, FOXL1, Foxo, FSH, GAD1, GPRC5B, KRT84, LHX5, LMX1A, MAGED1, MSX2, OTP, PGRMC1, Pi4k, PI4K2A, PI4KA, Rb, SOX2, TCF3, TOX, TP53I11, UNC5A | 20 | 29 | Carbohydrate Metabolism, Lipid Metabolism, Small Molecule Biochemistry |
| 50 | ARHGAP4, ARHGAP6, ARHGAP8, ARHGAP29, ARHGDIA, ARPC2, BAIAP2, CDC42, COL10A1, COL11A2, DGKQ, DIAPH1, Erm, Gα 12/13, GRLF1, HPCA, IBSP, ICMT, KIFAP3, MCF2L, MSN, MYO9B, Phosphatidylinositol4, 5 kinase, PIP5K1B, Ras homolog, RDX, RGMA, RHOA, RhoGap, RHOH, RHOJ, SPN, srGAP, SRGAP1, SRGAP2 | 19 | 29 | Cell Signaling, Cell Morphology, Cellular Assembly and Organization |
| 51 | ATG5, ATXN3, CTSE, EMG1, Immunoproteasome Pa28/20s, KHDRBS1, LCK, MAGEA3, NAT6, PMS2, Proteasome PA700/20s, PSD2, PSMA, PSMA1, PSMA5, PSMB, PSMB2, PSMB6, PSMB7, PSMB8, PSMC, PSMC1, PSMC2, PSMC4, PSMD, PSMD4, PSMD7, PSMD14, PTPN22, SNCAIP, SNX3, SOS2, WDR48, ZDHHC17, ZDHHC18 | 19 | 29 | Cellular Assembly and Organization, Cellular Function and Maintenance, Connective Tissue Disorders |
| 52 | ACAC, ACACB, ACAT1, ADIPOQ, ADIPOR2, AMPK, Creatine Kinase, Cytochrome c, ELOVL6, ENSA, FABP, FABP2, FABP3, FABP6, FOXO3, GYS2, HMGCR, Insulin, KHK, LCP2, LIPE, MLXIPL, PLB1, POLDIP3, PRKAA, PRKAA2, PRKAB1, PRKAB2, PRKAG1, SLC25A12, STX6, STXBP4, UCP3, UQCRC2, UQCRH | 19 | 28 | Lipid Metabolism, Small Molecule Biochemistry, Carbohydrate Metabolism |
| 53 | AHSA1, ANAPC10, ANP32A, CALU, CAMK2D, Glycogen synthase, HSPD1, MAP2K1/2, MID1, Myosin light chain, NEK1, NPTX2, PFKFB2, PP1, PP1/PP2A, PP2A, PPP1CB, PPP1R11, PPP1R1A, PPP2R1A, PPP2R2A, PPP2R2C, PPP2R5A, PPP2R5B, PPP2R5C, PSME2, Pyruvate kinase, RAB18, RAB11A, RCN1, RCN2, SLC6A4, SLC8A1, TMEM43, UPF1 | 19 | 28 | Cancer, Cell Death, Reproductive System Disease |
| 54 | ABCB4, ABCG4, AP4E1, APOA1, APOC4, ARG2, CD36, CNOT1, CNOT4, Coup-Tf, CPT1, CPT1B, CTNNBL1, CYP24A1, FXR ligand-FXR-Retinoic acid-RXRα, GCN1L1, GPLD1, INSIG2, LTF, N-cor, NCOR-LXR-Oxysterol-RXR-9 cis RA, Nr1h, NR1H4, NR2F2, NUDT7, PALB2, RANBP3, RARA, RQCD1, Rxr, SGOL2, SPP1, THRB, UCP1, USF2 | 19 | 28 | Lipid Metabolism, Molecular Transport, Small Molecule Biochemistry |

TABLE 4-continued

Regulated Networks from Melanoma Tumor Sample

| ID | Molecules in Network | Score | Focus Molecules | Top Functions |
|---|---|---|---|---|
| 55 | AGMAT, Arginase, BAT3, BIRC5, Caspase, DPT, DTX3L, FGF20, FGFR3, IFT57, Ikb, JUP, KHDC1, KLF5, MAPKAP1, MST1, NGLY1, Nos, OTUD7B, PCCA, peptidase, PTPN14, RNF7, RNF130, SHFM1, STAM2, TH1L, TMPRSS11D, Tnf receptor, TTLL3, UBC, UBE2D3, Ubiquitin, UBL7, ZNRF1 | 19 | 28 | Cell Death, Metabolic Disease, Genetic Disorder |
| 56 | CD44, CSF1, CSPG4, DCN, ELN, FBN1, FCN1, FCN2, Fgf, Fibrin, GDF15, Gpcr, GPR68, Igfbp, KISS1, Mmp, MMP2, MMP7, MMP12, MMP14, MMP15, MMP16, MMP20, MMP24, NUAK1, PCDHGC3, PCOLCE, PCSK6, Plasminogen Activator, PLAU, PTPRO, SERPINE2, SPOCK3, Trypsin, VCAN | 18 | 28 | Protein Degradation, Connective Tissue Disorders, Genetic Disorder |
| 57 | ALS2CR11, CD27, CD70, CNKSR1, DUSP4, DUSP6, DUSP9, DUSP16, E4F1, ELK4, GCKs, Il3r, Jnk, Jnkk, KIAA1217, MAP1S, MAP3K2, MAP3K4, MAP4K2, MAP4K5, MAPK10, MAPK12, MEKK, MEKKs, MGAT3, MINK1, MKP1/2/3/4, NET1, PRDX4, RASSF1, RHPN1, SERPINB3, TAOK3, TEX11, TRAF | 17 | 27 | Cell Signaling, Embryonic Development, Tissue Development |
| 58 | 3',5'-cyclic-nucleotide phosphodiesterase, AKAP, AKAP1, AKAP5, AKAP10, Ap1, ARFGEF2, ARL3, C2ORF65, C3ORF15, Camk, CBFA2T3, CRX, ELL, GSS, NPHS2, NRL, OSGIN1, PADI4, Pde, PDE11A, PDE4D, PDE4DIP, PDE6 (rod), PDE6B, PDE6D, PDE6G, PDZK1, Pki, PRKAC, PRKAR2A, PRKAR2B, PTGIR, SIRT2 | 17 | 27 | Cardiovascular Disease, Visual System Development and Function, Kidney Failure |
| 59 | CARS, CBX3, CDX4, CREB1, FUSIP1, GALNT1, GALNT2, GALNT5, GALNT7, GALNT8, Glutathione peroxidase, GTF2A2, GTF2E1, GTF2F1, HPS6, MUC1, PDHA2, PEPCK, Polypeptide N-acetylgalactosaminyltransferase, RNA polymerase II, SLC18A2, SUB1, Taf, TAF1, TAF5, TAF11, TAF1L, TAF9B, TFIIA, TFIIE, TFIIH, TGS1, UPP1, VSNL1, ZEB1 | 17 | 27 | Post-Translational Modification, Gene Expression, Cellular Compromise |
| 60 | BRAF, CD3, CD247, CFLAR, CRKL, DOCK2, DST, Dynein, FKBP4, FLT3, GLMN, GRIA2, GRIA3, IKK, IL2RA, JINK1/2, MAP1B, MAP4K4, NF2, NUDCD3, OIP5, PAFAH1B1, PCDHA6, POP7, PPIL2, Ptk, Rar, RELN, RPP30, SERPINB10, SIRPA, SPIC, STAT5a/b, TCR, TUBB2B | 17 | 27 | Nervous System Development and Function, Cancer, Neurological Disease |
| 61 | ABCC3, ABCC4, ALDH, CAR ligand-CAR-Retinoic acid-RXR&alpha, CES3, CITED2, CNOT3, CREBBP, CRYAA, CRYGC, CYP2C9, EID1, GST, HIST1H4E, HOXD10, HS3ST1, HS3ST3A1, HS3ST3B1, MAST1, MIP, NCOA, Ncoa-Nr1i3-Rxra, NR1I3, PXR ligand-PXR-Retinoic acid-RXRα, Retinoic acid-RAR-RXR, SCAND1, SLC35A2, SS18L1, sulfotransferase, SULT1A3, SULT1E1, SULT4A1, ZNF434, ZNF446, ZSCAN20 | 17 | 27 | Drug Metabolism, Vitamin and Mineral Metabolism, Amino Acid Metabolism |
| 62 | AGK, BDKRB2, C16ORF14, CASD1, CD48, CHRM2, DOK4, ERK, FAU, G alpha, G alpha-G beta-GDP-G gamma, G protein beta gamma, G-protein gamma, GNA14, GNAI1, GNAL, GNG2, GNG4, GNG7, GNG12, GPER, GPR1, GPR4, KCNJ5, KLB, MPZL1, Plc beta, S1PR, S1PR2, S1PR3, S1PR5, SPRED1, TFG, TNFSF8, UBA5 | 17 | 28 | Cell Signaling, Nucleic Acid Metabolism, Small Molecule Biochemistry |
| 63 | BGN, BMP, BTF3, CDKN2B, CK1/2, COL1A2, CSNK1A1, CSNK1E, CSNK2A1, CSNK2A2, EGLN1, EID2, ENTPD5, FST, Glucocorticoid-GCR, JPH3, NAP1L1, PEX6, PURB, RFX2, RFX3, RNF111, Smad, SMAD3, SMAD4, SMAD5, Smad2/3, Smad2/3-Smad4, SSRP1, SUPT16H, TEAD1, TFE3, Tgf beta, TGFB2, YBX1 | 17 | 28 | Gene Expression, Cancer, Gastrointestinal Disease |
| 64 | ATP2A1, ATP2A3, ATP2B2, C16ORF70, Ca2 ATPase, Calmodulin, CASK, CASQ2, CTNNA3, DLG1, F11R, GPR124, Guk, HR, JAM, JAM3, KCNJ10, MLLT4, MPP4, MPP5, MPP7, PARD3, Pmca, PVRL4, RGN, Ryr, SERCA, SIPA1, SLC16A3, SSX2IP, T3-TR-RXR, TBR1, THRA, Thyroid hormone receptor, TRDN | 16 | 26 | Cell-To-Cell Signaling and Interaction, Cellular Assembly and Organization, Cellular Function and Maintenance |
| 65 | ADAM9, ADAM10, ADAM28, ADAM30, C5ORF13, CD9, CD53, COL13A1, F12, FN1, FYB, GAL3ST1, HTRA1, I kappa b kinase, ICAM2, Integrin, Integrin alpha V beta 3, Integrinα, Integrinβ, ITGA4, ITGA9, ITGAE, ITGB1, ITGB5, ITGB8, LACRT, LTBP1, LTBP3, Metalloprotease, MIA, PACSIN3, PRAP1, Talin, VTN, WASP-SLAP130-SLP76-VASP-NCK-VAV | 16 | 27 | Cancer, Cell-To-Cell Signaling and Interaction, Hematological Disease |
| 66 | Akt, CDH13, CEP55, CISH, COL4A3BP, CTF1, FKHR, IL11, IL6ST, INPP4A, IRS2, JAK, JAK1, LEPR, LIFR, LMO4, LPXN, MPL, PHIP, POM121, SCGB3A1, SEC14L2, SOCS, SOCS3, SOCS4, SOCS6, STAT, STAT1/3/5 dimer, Stat3-Stat3, TBC1D4, TPOR dimer, UXS1, VPS37A, VPS37B, WSX1-gp130 | 16 | 26 | Cellular Growth and Proliferation, Hematological System Development and Function, Inflammatory Response |

TABLE 4-continued

Regulated Networks from Melanoma Tumor Sample

| ID | Molecules in Network | Score | Focus Molecules | Top Functions |
|---|---|---|---|---|
| 67 | APOBEC3G, AZI2, BFAR, CASP1, CASP10, CD86, CELSR1, CYB561, CYLD, IFIH1, IFN ALPHA RECEPTOR, IFN Beta, Ifn gamma, IFNA4, IFNAR1, Interferon alpha, IRF, IRF8, ISGF3, NF-κ B, Oas, OAS2, PECAM1, PTGDR, RARRES3, RSAD2, SF3A1, SGSM3, SLC2A11, TANK, TGM1, Tlr, TNFAIP3, TRIB2, ZBP1 | 16 | 26 | Gene Expression, Antigen Presentation, Antimicrobial Response |
| 68 | AMD1, BLK, BRSK1, C2, C1q, C1R, CARD8, CARD16, CD22, CD300A, CD79A, Complement component 1, DLEU2, ENPP3, FCAR, Fcgr2, FCGR2A, HRG, IgG, IGHE, IGHM, IGL@, Igm, IL21, INPP5D, LILRB1, MS4A1, NUP205, PEAR1, SHC1, SHCBP1, SHIP, SHP, SYK/ZAP, TPR | 15 | 27 | Cell Death, Hematological Disease, Immunological Disease |
| 69 | ARVCF, CABP1, CaMK-II/IV, CAMK2A, CAMK2G, CaMKII, CDH2, CHRNE, CK1, Creb, EGLN3, Filamin, GPD1, GRIN, GRIN2A, GRIN2C, GRIN3B, LRRC7, MUC5AC, MYOG, NMDA Receptor, NOX5, PACSIN2, PYGM, SDHD, SIX2, SLC32A1, Succinate dehydrogenase, Top2, Wnt, WNT3, WNT11, WNT5A, WNT8B, WNT9A | 15 | 25 | Neurological Disease, Organismal Injury and Abnormalities, Respiratory Disease |
| 70 | ANKRD10, BARHL1, BAT1, C12ORF41, C3ORF26, CIRH1A, CLUAP1, CNIH, DDX52, DHX15, DIMT1L, INTS2, MAGEA11, MBOAT2, MED13, MED23, MED28, MED7 (includes EG: 9443), MIRN222 (includes EG: 407007), MYBBP1A, PNN, POLR1D, POLR2C, POLR3A, PPIG, PRKRIP1, PRPF4B, PSMC6, SFRS3, SMC4, SPRYD5, TCOF1, TFIP11, TRMT1, WTAP | 15 | 25 | Gene Expression, Auditory Disease, Cellular Compromise |
| 71 | Actin, Alpha actin, ATPase, CALD1, CASC1, CCL5, CCL16, CD163, CEACAM1, Ck2, CTSB, CXCR5, DTNA, F Actin, Mlc, MYH3, MYH7, MYH8, MYH14, MYL6, Myosin, Myosin Light Chain Kinase, NAMPT, NFKBIL2, PRKG1, SERPINB13, SQLE, STK17A, Tni, TNNI3, TNNT2, Tropomyosin, Troponin t, TUBB2A, TUBB2C | 14 | 24 | Cardiovascular System Development and Function, Skeletal and Muscular System Development and Function, Tissue Development |
| 72 | AKT3, C16ORF35, C5ORF13, CAPN6, CCNT2, FAM38B, FBN2 (includes EG: 2201), FNDC3A, GSC2, JMJD1A, KY, LGI2, LOXL3, MECP2, MIRNLET7A3, MIRNLET7F2 (includes EG: 406889), NNT, NRK, PCDH7, PTPN12, RALGPS2, RET, RNF4, SCARA3, SDK1, SLC2A3, SMARCA1, SNX25, TCIRG1, UBE2B, UBE2N, UBE2V2, UGCGL1, XPO4, ZNF215 | 14 | 24 | Nervous System Development and Function, Tissue Development, Cancer |
| 73 | AFAP1L1, AK5, C17ORF28, C7ORF26, CDK9, CEP57, COL5A2, E2F3, E2F4, E2F6, FRMD6, GCSH, H2AFX, HMGB1 (includes EG: 3146), KHDRBS1, MAGT1, MYCN, NCL, NMI, NUCKS1, PPIL5, RABIF, RBBP8 (includes EG: 5932), RBL2, RFC3, RNF114, RPL22, RPS16, RPS23, RUSC2, SRPR, TERC (includes EG: 7012), TERT, TRIM46, UBASH3B | 14 | 24 | Cell Cycle, Connective Tissue Development and Function, Gene Expression |
| 74 | ABCC1, ARSA, ARSI, ATP6V0B, BTBD7, C16ORF84, C17ORF39, C2CD2L, C5ORF25, CCDC136, CEND1, CSPG4, DCUN1D5, EMG1, EPC1, FABP3, FAM131A, IGSF9B, ILVBL, IRF8, JMJD3, LARP4, MIRN337, MIRN130B (includes EG: 406920), MIRN149 (includes EG: 406941), MIRN205 (includes EG: 406988), MIRN28 (includes EG: 407020), MUS81, RSF1, SAMD1, SFRS1, STBD1, SULF2, SUMF1, WDR44 | 14 | 24 | Lipid Metabolism, Small Molecule Biochemistry, Carbohydrate Metabolism |
| 75 | ARL17P1, C15ORF15, C20ORF43, CDK5RAP3 (includes EG: 80279), CHERP, DNAJC30, GPR39, HNF1A, HNF4A, HOOK3, KIF9, MPZL2, MRPS23, OSBPL11, PRKAB1, retinoic acid, SLC5A3, STX17, TTC25, TTC37, UFM1 | 13 | 18 | Gene Expression, Lipid Metabolism, Molecular Transport |
| 76 | B9D2, CNTN4, DCLK3, FBXO42, H2AFJ, HNF4A, INTS7, MLL5, MSRA, NAALADL2, NFYB, NFYC, PAQR5, RIMBP2, SFRS17A, SHOX2, TTC39B, TTLL9, ZNF524 | 13 | 17 | Gene Expression, Amino Acid Metabolism, Cellular Development |
| 77 | ARHGEF12, CD200R1, DOK1, FGF6, FNBP1, growth factor receptor, Il8r, KNDC1, MRAS, MTG1, NGF, NRAS, Ntrk dimer, P110, PDGF-AA, Pdgfr, Phosphatidylinositol 3-kinase, PI3K p85, PIK3CD, PIK3R3, PLCE1, PLXNB1, PTGFR, RAB3IL1, RAB3IP, Raf, Rap1, RAPGEF6, Ras, RASAL1, RASGRP2, RASSF2, RASSF4, RIN2, SSPN | 13 | 23 | Cell Signaling, Hematological System Development and Function, Cancer |
| 78 | AKR1C2, ATIC, B3GNT1, CD9, CDC7, CDH2, CDK6, COL1A2, COL6A1, COL6A2, COL6A3, CXCL10, Cyclin E, DBF4B, GAST, GGPS1, HNRPDL, Hsp27, LAMC2, MIRN362 (includes EG: 574030), MUC4, MUC5AC, NKD2, OSR2, PCSK1, PLAT, SCCPDH, SCG5, SERPINB5, SLC39A14, TGFA, TGFB1, TGM1, WISP3, ZNF236 | 13 | 23 | Genetic Disorder, Skeletal and Muscular Disorders, Dermatological Diseases and Conditions |

TABLE 4-continued

Regulated Networks from Melanoma Tumor Sample

| ID | Molecules in Network | Score | Focus Molecules | Top Functions |
|---|---|---|---|---|
| 79 | ATF7, ATP4B, B2M, CGA, COMMD4, COMMD8, COMMD1 (includes EG: 150684), CYLD, CYSLTR2, EMID2, ETS, FARS2, FOS, GABA, HMGB1 (includes EG: 3146), IL1R1, IRF8, MIRN128-2 (includes EG: 406916), NFATC1, NFKB1, NLRX1, PCNX, PSMC5, S100B, SLC36A1, SLC39A13, SPAG9, SPP1, STX1A, SV2B, TGFB2, TXLNB, UBE3C, VISA, ZNF503 | 13 | 23 | Amino Acid Metabolism, Molecular Transport, Small Molecule Biochemistry |
| 80 | ADAM10, ADAM19, ATM, CD44, CD1E, CH25H, CHI3L2, DCLRE1C, DDX5, EIF2S1, ESF1, GNL1, GPR126, GPR176, HMGB1 (includes EG: 3146), HNRNPD, IKK, LAMA3, LAMA5, LAMB3, LAMC2, MMP1 (includes EG: 4312), PLAT, PLAU, PLG, PRKDC, RELB, RTP3, SDC4, SLC35E1, TMEM49, TNF, TP73, TRIM15, ZNF330 | 12 | 24 | Endocrine System Development and Function, Nervous System Development and Function, Organ Morphology |
| 81 | ABCB10, C14ORF172, C2ORF49, CHD1L, DEM1, EIF1AD, EXOD1, HNF4A, NOL7, SEC23A, SEC23IP, SLC22A3, SLMO2, STAT1, STOML1, TMEM53, TRMT6, TTC22, ZAN | 12 | 16 | Cell Morphology, Cellular Assembly and Organization, Cellular Function and Maintenance |
| 82 | AHDC1, ATN1, ATXN1, BEND2, C17ORF81, GPATCH8, HNF4A, IL34, IPO8, KIAA0664, KIAA0913, METT11D1, MIRN135A1, MIRN135A2, MIRN135B (includes EG: 442891), MTERF, MTERFD2, NR3C1, PHPT1, RAD54L2, SLC1A6, TOX4, UNK, WNK2 | 11 | 18 | Gene Expression, Cellular Development, Lipid Metabolism |
| 83 | ABCA13, ACOT8, ARNT, AZGP1, BNIP1, BTRC, CRP, DALRD3, EPO, GATA2, GATA3, GATA4, IFNAR1, KCNH6, KIT, L3MBTL, LMO2, NOS3, NOSIP, PDLIM2, PIM1, PTPN2, RINT1, SEC22B, SLC24A1, STAT1, Stat1/3, TAL1, TCF12, TYK2, UBE2F, USE1, ZDHHC8, ZDHHC21, ZW10 | 11 | 22 | Gene Expression, Hematological System Development and Function, Cellular Development |
| 84 | Arf, CTTN, Cyclin D, EPS8L1, EPS8L2, Fgfr, FGFR4, FRS2, GAP43, Gsk3, HEY1, MCM6, MEF2, MEOX2, MTSS1, MYH11, NEK3, NFAT complex, p70 S6k, Pak, PAX1, PDAP1, Pdgf, Pdgf Ab, PDGFB, PDGFC, phosphatase, PLC gamma, PRKD1, RPS6KB2, SAMM50, SCNM1, Sos, VAV, VAV2 | 10 | 21 | Cell Morphology, Cellular Assembly and Organization, Antigen Presentation |
| 85 | ADAMTSL1, AGPAT4, ASCC3L1 (includes EG: 23020), ATP5B, BAT1, C17ORF85, CCNY, CFL1, CLASP1, CRTC1, CRTC2, DHX15, DYRK1B, EPB41, FBXO44, IL3, IL17A (includes EG: 3605), KIF1B, KRT37, MEGF10, MIRN328, MIRN205 (includes EG: 406988), MIRN211 (includes EG: 406993), NCDN, NONO, OTX2, PARD3B, RNPS1, SFRS1, SMCR7L, TOP2A, YWHAB, YWHAG, ZFP36, ZNF295 | 10 | 21 | Cellular Development, Cellular Growth and Proliferation, Hematological System Development and Function |
| 86 | ACCN4, ARIH1, C17ORF50, C1ORF9, C20ORF111, CHST11, CTSK, EIF3M, ELK1, FATE1, HNRNPU, IFIT1, KCNAB3, MED13, MIRN349, MIRN142 (includes EG: 406934), MIRN292 (includes EG: 100049711), MIRN298 (includes EG: 723832), MIZF, MYST3, OR8G1, PAFAH1B1, PCGF3, SCUBE3, SEC14L4, SGK1, SLC23A2, SPATA2, STAG2, TNIK, TRAF2, WAPAL, WDR38, XKR6, ZFHX4 | 10 | 21 | Carbohydrate Metabolism, Small Molecule Biochemistry, Vitamin and Mineral Metabolism |
| 87 | BDP1, BNC2, CBX3, CDCA7, CDK9, CDK4/6, CMAS, CSRP2, CSRP2BP, CTBS, Cyclin E, ETV3, GTF2H4, HAP1, HCG 2023776, HNRNPC, ID1, IMPAD1, MFAP1, MIRN187 (includes EG: 406963), MIRNLET7B (includes EG: 406884), MTPN, MYBL2, MYC, NEUROD1, PDGFB, RB1, RPS25, RRM2, SKP2, SLC35C1, SLITRK1, TYMS, UBAP2, ZNF691 | 10 | 21 | Cell Cycle, Gene Expression, Cancer |
| 88 | CACNA1I, CATSPER1, CATSPER2, CHIC2, EDEM2, ERGIC1, GARNL1, HAND1, KITLG (includes EG: 4254), LEF1, LRRN4, MAGEB2, MAGEE1, MDFI (includes EG: 4188), MIRN129-1 (includes EG: 406917), MIRN129-2 (includes EG: 406918), MYCN, MYF5, MYOD1, MYOG, NCL, NR4A3, PARP1, PAX3, PHOSPHO1, RABL5, RPL36A, RPS3A, TAL1, TCF3, TCF12, TCF15, USP7, ZNF423, ZNF607 | 10 | 21 | Cellular Development, Hematological System Development and Function, Hematopoiesis |
| 89 | AGTRAP, ANK1, CACNB3, Calcineurin A, Calcineurin protein(s), CASR, DHRS9, ERLIN2, GABBR1, ITPR, ITPR1, ITPR2, JUNB, MEF2D, N-type Calcium Channel, Nfat, NFAT5, NFATC1, Peptidylprolyl isomerase, PGM2L1, Pkg, PLA2G6, Pp2b, PPP3CA, RHD, SAMD4A, SCN3A, SCRIB, SPTAN1, TRP, TRPC4, TRPV6, UBE4B, VitaminD3-VDR-RXR, Voltage Gated Calcium Channel | 10 | 24 | Cell Signaling, Molecular Transport, Vitamin and Mineral Metabolism |

TABLE 4-continued

Regulated Networks from Melanoma Tumor Sample

| ID | Molecules in Network | Score | Focus Molecules | Top Functions |
|---|---|---|---|---|
| 90 | ANXA8L2, AR, CCNE1, CREBBP, CYP1A1, CYP2B6 (includes EG: 1555), CYP2D12, CYP4B1, ETV1, GAS7, GHRHR, HOXD1, IQCK, KAT2B, KLK2, MIRN202 (includes EG: 387198), MMP1 (includes EG: 4312), MYCN, NCOA3, NDN, NUCB2, PLAC2, PLUNC, PRKACA, PYCR2, retinoic acid, RPS12, SERPINA5, SERPINE1, SMARCA4, SP110, THRA, TYSND1, ZNF673 | 10 | 20 | Gene Expression, Cancer, Cellular Growth and Proliferation |
| 91 | ATP10A, ATP11A, ATP11B, ATP5B, B4GALNT4, BHLHB5, C10ORF2, C5ORF15, CAPRIN1, CDC25B, CDH20, CLIC4, CRIP3, D4S234E, EPC1, FRAS1, GATAD2B, H3F3A (includes EG: 3020), KIAA0907, Mg2+-ATPase, MIRN330, MIRN15B (includes EG: 406949), MIRN195 (includes EG: 406971), MIRN22 (includes EG: 407004), NEBL, PCOLCE, PPM1G, PRKD1, PURA, RAB28, SEMA6A, SFRS1, SPIRE1, YWHAQ (includes EG: 10971) | 10 | 20 | Cellular Growth and Proliferation, Connective Tissue Development and Function, DNA Replication, Recombination, and Repair |
| 92 | ABCD3, AFG3L2, C1ORF38, CIDEC, CTSK, CXCL9, ERAP2, FGF2, GAL3ST1, ganglioside GD1b, Gsk3, IFI44L, IFNG, IL1RN, MEST, MON2, MRAS, MTMR3, MTMR4, Nos, ODC1, PI3, PRKDC, PTCD3, RNASE7, SASH3, SDC4, SLC28A2, SPP1, TGFB2, TNFRSF11B, TNFRSF1A, VCAM1, ZFP57, ZFX | 9 | 20 | Skeletal and Muscular System Development and Function, Tissue Morphology, Tissue Development |
| 93 | ACADS, ADAMTS2, ADSL, AQP5, CD36, CDC37, CHIA, CLCN7, CLIC2, DCN, FGF7, FOXF1, FPR2, FUT3, GAB2, GATA2, HAS2, HDAC9, HOXA9, IRF8, ISG15 (includes EG: 53606), LTBP2, MAP4K5, NRXN1, NXPH3, PDZD2, SDC4, SMAD7, ST3GAL3, TGFB2, TNF, TRIP6, UACA, ZBTB11, ZNF107 | 9 | 20 | Cellular Movement, Cellular Function and Maintenance, Organ Development |
| 94 | ADM, AIFM1, BLM, CASP3, CDH2, COL4A3 (includes EG: 1285), cyclic AMP, deoxycholate, EBAG9, EIF2AK3, EMCN, EMILIN2, GALC, ganglioside GD1b, GBA, GNAS, HSPB2, HSPB6, MAP4K1, MLH1, NEFM, NFE2L2, PARG, PDE4A, phosphatidylserine, PRKD1, PRKDC, PSD3, RBM5, RXFP1, S1PR5, SGPL1, SGPP2, sphingosine-1-phosphate, ZC3H11A | 9 | 20 | Cell Death, Cell Signaling, Molecular Transport |
| 95 | BTRC, C15ORF27, CAND1, CDC34 (includes EG: 997), CDCA3, CDK9, CUL1, CUL7 (includes EG: 9820), Cyclin E, DDX4, FBXL2, FBXL3, FBXL21, FBXO2, FBXO4, FBXO6, FBXO7, FBXO10, FBXO15, FBXO18, FBXO21, FBXO41, FBXW2, FBXW8, GCM1, GEMIN8, KIAA1045, MIRN293, MIRN34B (includes EG: 407041), RC3H2, RNF7, SENP8, SKP1, SKP2, ZC3HC1 | 9 | 20 | Protein Degradation, Cancer, Immunological Disease |
| 96 | ACE, ADAMTS7, CEP135, CPN2, CTSK, FGF20, FGF22, Fgfr, FGFR1, FGFR4, Frizzled, GLI2, GPR1, heparan sulfate, heparin, KLB, LSAMP, NCAM1, NCAM2, NCAN, NDST2, PAX3, PPIB, PRELP, PRNP, PTPRZ1, SFRP1, SMAD9, SPP1, ST8SIA3, ST8SIA4, THY1, TSPY1, WNT2, ZNF587 | 9 | 20 | Carbohydrate Metabolism, Small Molecule Biochemistry, Cellular Development |
| 97 | Beta-galactosidase, BMP7, BTRC, COX17, DOM3Z, DYNC2H1, EEF1A1, EXOSC4, FAHD1, GATA4, GBA3, GLI2, GLI3, HDAC9, HIPK2, KATNAL1, LCT, LEF1, MEF2A (includes EG: 4205), PIAS2, PIAS3, PSG9, SCAPER, SENP6, SMAD2, SMAD4, SUMO1, TCTA, TMPRSS3, TRIM33, XIRP2, XPO5, XRN2, ZIC1, ZIC2 | 9 | 20 | Digestive System Development and Function, Gene Expression, Cell Signaling |
| 98 | 5'-nucleotidase, ABCA2, ABCD3, AFG3L2, Apyrase, ATP13A5, ATPase, C21ORF77, CANT1, CNKSR2, CTSK, DDX1, DHX8, DHX16, ENTPD1, ENTPD2, ENTPD3, ENTPD5, HEATR3, KIAA0494, KIAA1279, KIF20B, MIRN200C (includes EG: 406985), MOBKL2B, NT5C, NT5C2, Nucleoside-diphosphatase, PSMC1, PTP4A3, TIMM10, TIMM23, TMEM41B, TRPM3, WRNIP1, ZNF670 | 9 | 20 | DNA Replication, Recombination, and Repair, Nucleic Acid Metabolism, Small Molecule Biochemistry |
| 99 | 3-oxoacid CoA-transferase, ANKRD36B, ARL6IP5, C10ORF35, CAV1, DNAH1, DNAH5, DNAH9, DNAH10, DNAH11, DNAH14, DNAL4, DPY19L1, DTX4, ELOVL7, FBLIM1, FILIP1, FLNA, FLNC, GPSM2, HRAS, HSD17B8, JARID1B, MIRN31 (includes EG: 407035), MYOT, NEWGENE 1560614, NIPA2, OXCT1, OXCT2, PCYT1B, RPS6, RTP1, SCNN1A, TCTE3, TRIM54 | 9 | 20 | Lipid Metabolism, Small Molecule Biochemistry, Genetic Disorder |
| 100 | ABHD5, AGPAT3, ANKRD27, C7ORF42, CETN2, DPP8, FAM153A, FAM3D, FAM83H, HNF4A, LPHN3, METAP1, MIRN124-1 (includes EG: 406907), MIRN124-2 (includes EG: 406908), MIRN124-3 (includes EG: 406909), MIRN297-1, M1RN297-2, PLDN, PLOD3, RBM47, SFRS12, SFRS2B, SYPL1, TARBP1, YBX1, YBX2 | 9 | 17 | Carbohydrate Metabolism, Dermatological Diseases and Conditions, Genetic Disorder |

TABLE 5

Evidence for CDK2 pathway dysregulation

| Gene/Protein | Status | Notes |
| --- | --- | --- |
| CDK2 | Up-regulated (19-fold) | Consistent with hypothesis |
| PKCeta (PRKCH) | Deleted | Consistent with hypothesis |
| Rb | Unchanged | Neutral; activity regulated by CDK2 via phosphorylation |
| E2F | Unchanged | Neutral; activity regulated by binding of unphosphorylated Rb |

REFERENCES

Ajona D, Hsu Y-F, Corrales L, Montuenga L M, Pio, R. 2007. Down-regulation of human complement factor H sensitizes non-small cell lung cancer cells to complement attack and reduces in vivo tumor growth. *J Immunol.* 178:5991-5998.

Bertotti A, Comoglio P M, Trusolino L. 2006. Beta4 integrin activates Shp2-Src signaling pathway that sustains HGF-induced anchorage-independent growth. *J Cell Biol.* 175: 993-1003.

Chin L, Garraway L A, Fisher D E. 2006. Malignant melanoma: Genetics and therapeutics in the genomic era. *Genes & Dev.* 20:2149.

Du J, Widlund H R, Horstmann M A, Ramaswamy S, Ross K, Huber W E, Nishimura E K, Golub T R, Fisher D E. 2004. Critical role of CDK2 for melanoma growth linked to its melanocyte-specific transcriptional regulation by MITF. *Cancer Cell* 6:565-576.

Eustace A J, Crown J, Clynes M, O'Donovan N. 2008. Preclinical evaluation of dasatinib, a potent Src kinase inhibitor, in melanoma cell lines. *J Transl Med.* 6:53

Kashiwagi M, Ohba M, Watanabe H, Ishino K, Kasahara K, Sanai Y, Taya Y, Kuroki T. 2000. PKCeta associates with cyclin E/cdk2/p21 complex, phosphorylates p21 and inhibits cdk2 kinase in keratinocytes. Oncogene 54:6334-41.

Tetsu O, McCormick F. 2003. Proliferation of cancer cells despite CDK2 inhibition. *Cancer Cell* 3:233-245.

EXAMPLE 5

Melanoma Treatment

Melanoma tumor samples and control normal tissue were obtained by biopsy. Whole exome sequencing (i.e. complete sequence of all transcribed genes) was done using commercially available Illumina technology. This method also provides quantification of individual mRNAs which provides a measure of gene expression analogous to whole genome transcription profiling.

A total of 2,802 genes from transcription profiling with a fold-change of +/−1.8 were passed on to network analysis. The filtered list of 2802 genes was subjected to an algorithm (Ingenuity Systems) that finds highly interconnected networks of interacting genes (and their corresponding proteins). The networks were integrated with the sequence data for mutated genes. Protein/protein interaction is determined directly from the research literature and is incorporated into the algorithm. These findings were then further analyzed to find particularly relevant pathways, which could provide potential therapeutic targets or, if possible, clusters of interacting proteins that could be targeted in combination for therapeutic benefit.

In addition to the dynamic networks created from the filtered genes, expression and mutation data are superimposed onto static canonical networks curated from the literature in a second type of network analysis that often yields useful pathway findings.

Figure 18:
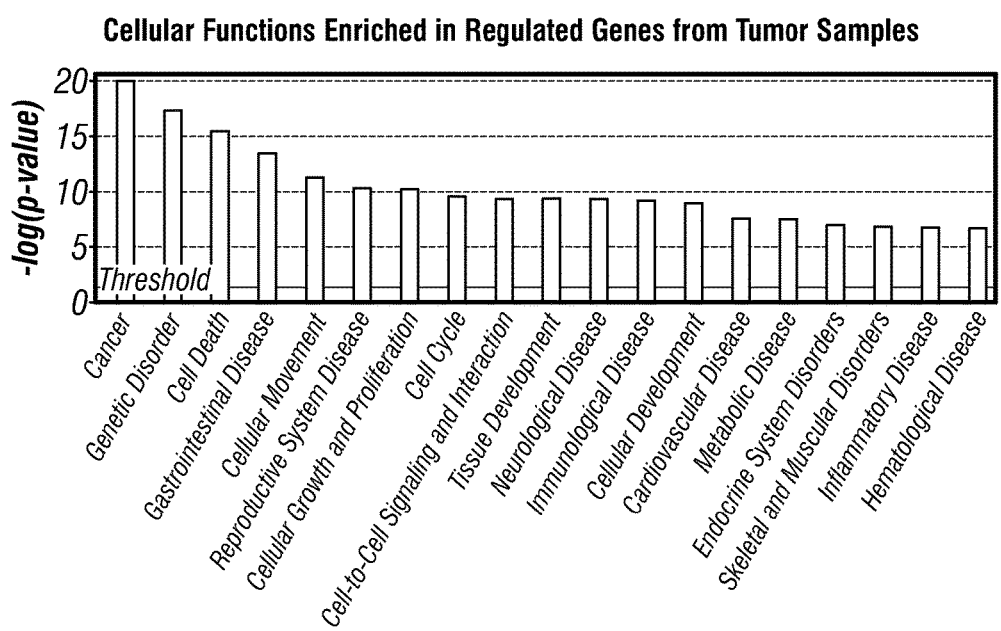
FIG. 18 is a graph showing cellular functions enriched in aberrant genes from a melanoma sample.

Before looking for potential therapeutic targets, an initial analysis was done to confirm that the global gene expression from the tumor sample was generally consistent with a priori expectations for a neoplasm of this type. The entire filtered list of genes was scored for associated cellular functions. The highest scoring category was Cancer, followed by Genetic Disorder (FIG. 18). Note also the high scoring of cell proliferative gene functions: Cell Death, Cellular Growth and Proliferation, Cell Cycle.

In addition, the networks that were assembled by the protein interaction algorithm from the filtered list of up- or down-regulated genes were analyzed with respect to the cellular and organismal functions of their individual component genes. The four top-scoring networks (with respect to the interconnectedness of their component genes) were greatly enriched in the following functions:

| | |
| --- | --- |
| Cellular Assembly and Organization | Amino Acid Metabolism |
| Post-Translational Modification | Cellular Movement |
| Hematological System Development and Function | Immune Cell Trafficking |
| Protein Synthesis | Protein Trafficking |
| Genetic Disorder | Small Molecule Biochemistry |
| Cancer | Skeletal and Muscular Disorders |
| Embryonic Development | |

This overall pattern is consistent with what one might expect from the global gene expression of a tumor sample, as compared to normal tissue. Both of these classes of findings are consistent with global gene expression patterns of tumor tissue compared with normal tissue. These are very high-level general categories and by themselves do not point towards a therapeutic class. However they help to confirm that we are looking at signals from the tumor sample and that the integrity of the gene expression milieu has been maintained. The entire list of networks and their associated functions is set forth in Table 6 at the end of this example.

Figure 19:
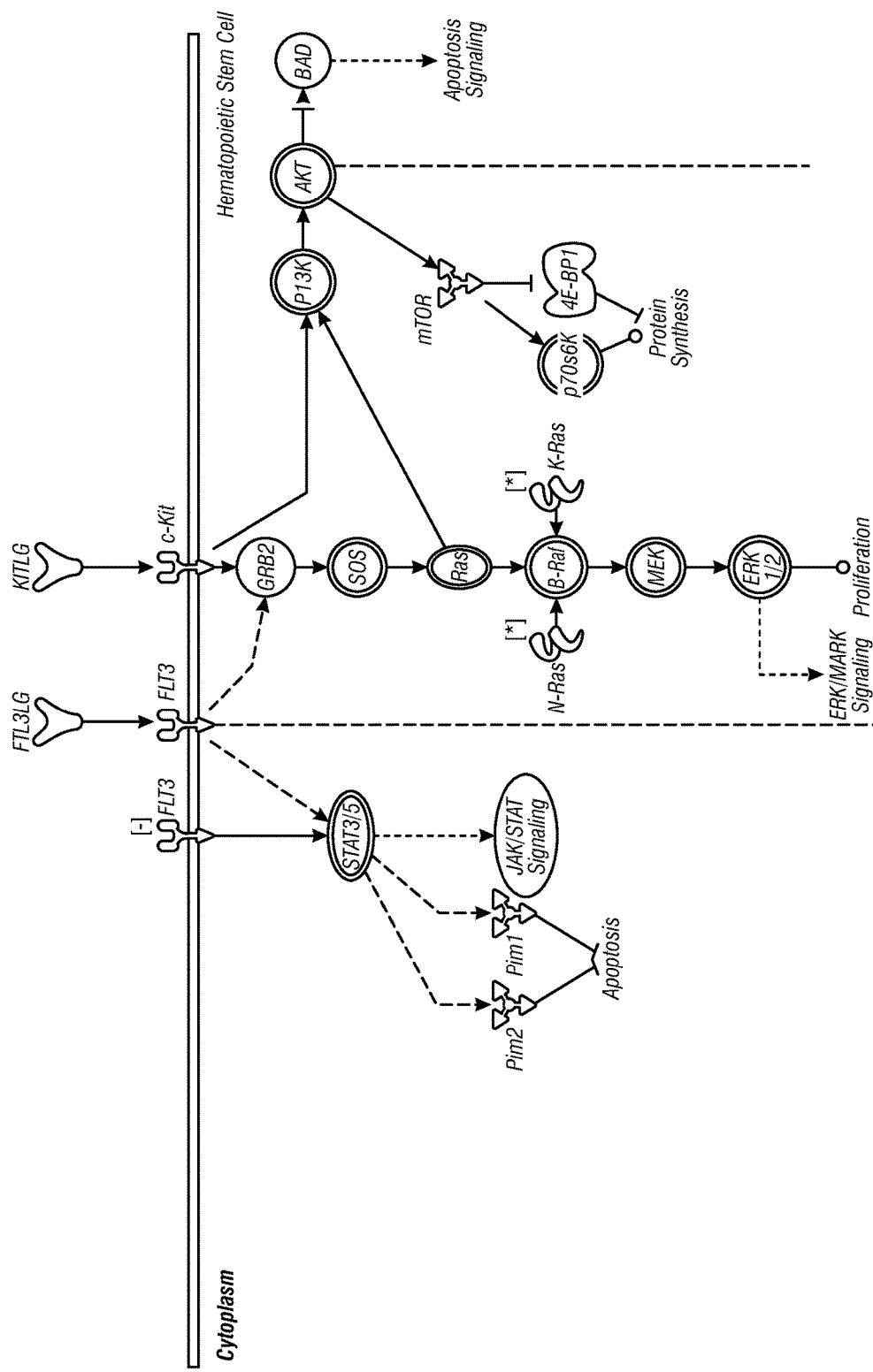
FIG. 19 is a diagram of the signaling pathway associated with B-Raf.

The sequence data revealed an activating V600E mutation in the B-Raf gene. This mutation is relatively common in melanoma (Goel, et al., 2006) and leads to constitutive activation of B-Raf and downstream MAP kinase/ERK signaling pathway, which in turn promotes cell proliferation (Schreck and Rapp, 2006). The pathway associated with this is shown in FIG. 19. B-Raf mutations are also associated with non-Hodgkin's lymphoma, colorectal cancer, thyroid carcinoma, and adenocarcinoma and non-small cell carcinoma of lung. B-Raf is targeted by the drug Sorafenib, approved for kidney cancer and liver cancer, however, results from clinical trials in melanoma have been somewhat disappointing (Dankort, et al., 2009). There is also a drug currently in trials that specifically targets the V600E mutation (PLX-4032). Activated B-Raf acts via phosphorylation of downstream MEK1/2 and subsequent activation of ERK1/2. ERK1/2 then acts via a variety of mechanisms to induce cell cycle progression and cell proliferation. Inhibiting activated B-Raf would thus be expected to inhibit cell proliferation.

Figure 20:
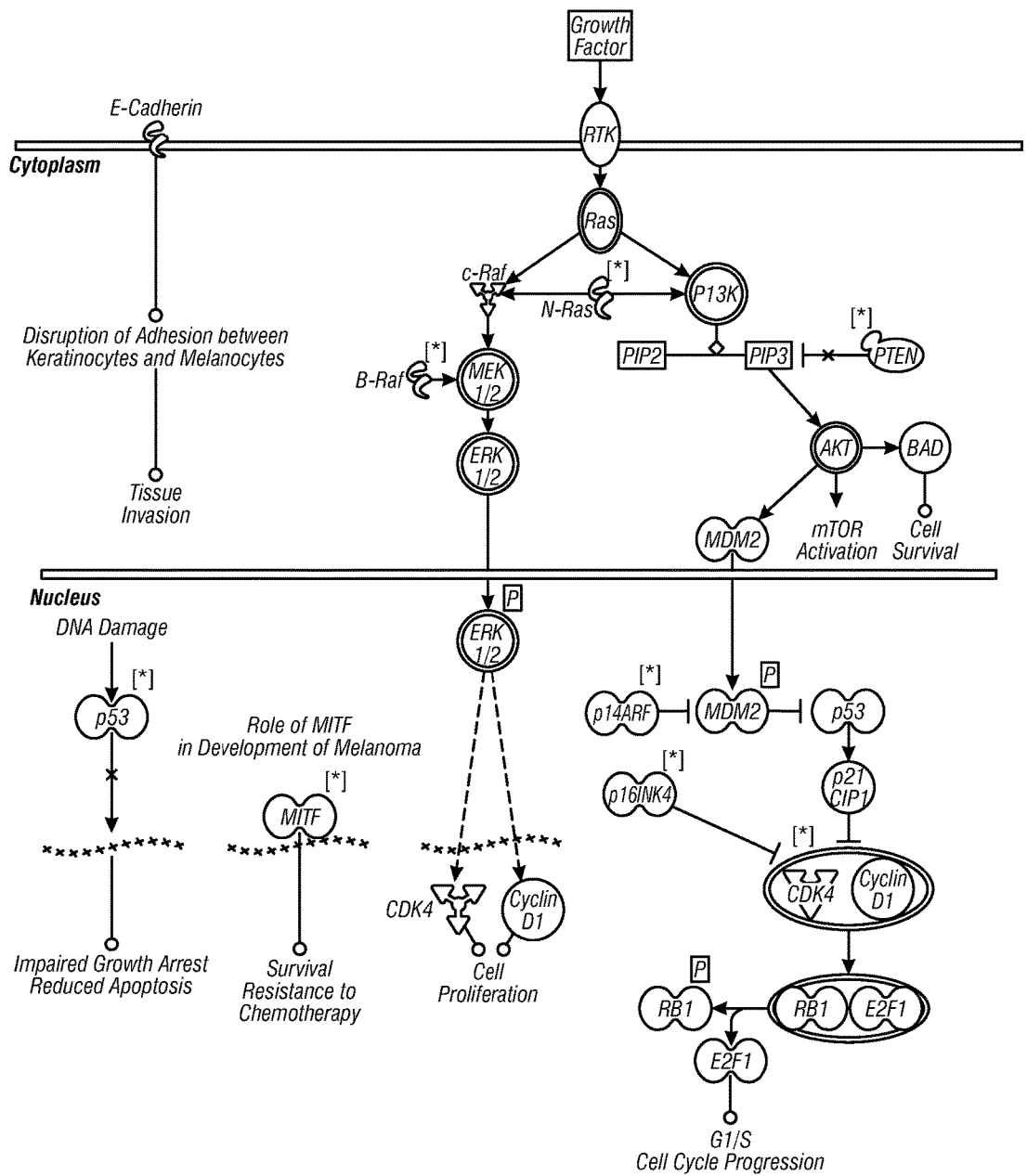
FIG. 20 is a diagram showing the pathways associated with PTEN down-regulation.

A second common finding in melanoma patients is the loss of the tumor suppressor PTEN. While PTEN was not mutated in the tumor sample, it was down-regulated approximately 5-fold. PTEN loss has been shown to activate AKT, which is also up-regulated in the tumor with subsequent activation of the mTOR pathway, a protein kinase pathway that results in the phosphorylation of p70S6K, 4EBP, RPS6 and EIF-4B. This pathway is shown in FIG. 20. These in turn stimulate translational initiation and contribute to cell growth. Dysregulation of the mTOR pathway is implicated as a contributing factor to various cancers. Inhibition of mTOR by one of the approved inhibitors (e.g., rapamycin, temsirolimus) might be expected to overcome the loss of expression of tumor suppressor PTEN and thus be beneficial. As the case with B-Raf inhibition, however, mTOR inhibition has had clinically mixed results in various cancers.

Since both pathways converge at the level of cell proliferation, and it is known that targeting these pathways individually in patients with cancer has mixed results, it might be expected that targeting both pathways would be beneficial. In fact, because of the common co-occurrence of B-Raf mutation and PTEN loss in many melanoma patients, it has long been thought that B-Raf and PTEN might co-operate in the oncogenesis of melanoma and therefore targeting either gene individually might not be as therapeutically effective as targeting both. A recent study has shown that in a mouse model, inducing both B-Raf V600E and PTEN loss very potently produced melanoma which very closely recapitulated the human disease. Each genetic manipulation by itself was not as effective at inducing melanoma. Furthermore the tumors were effectively treated by a combination of a MEK inhibitor (MEK is downstream of, and activated by, B-Raf) and an mTOR inhibitor (mTOR is downstream of, and inhibited by, PTEN). Neither drug alone was effective (Dankort, et al., 2009). This implies that in patients with both B-Raf V600E activating mutation and PTEN loss, a combination of either a MEK or B-Raf inhibitor, and an mTOR inhibitor may be efficacious, and may explain why either drug class acting alone has had disappointing results.

Thus, the integration of two different genomic data sources revealed that two distinct but interacting pathways were dysregulated, and therefore potential targets. B-Raf was mutated but not transcriptionally regulated, and conversely, PTEN was down-regulated but not mutated. Either technology by itself (gene expression profiling or sequence data) would therefore have only indicated dysregulation of one of the pathways as a likely contributor to oncogenesis and tumor growth. Furthermore, the research literature provided an animal model validation for both these pathways being critical for melanoma development, and their combined inhibition being necessary for effective treatment. This type of integration also provides for a means of drug discovery via repurposing of existing drugs, as non-obvious findings will emerge from single patients which may be generalizable to other patients with similar pathway dysregulation.

While in the literature report described above a MEK inhibitor was used to inhibit the B-Raf pathway downstream of B-Raf itself, there are currently no approved MEK inhibitors, although trials are ongoing. It may therefore be possible to use a B-Raf inhibitor in combination with an mTOR inhibitor (which is also currently approved).

Although we did not see much up-regulation of genes downstream of B-Raf or PTEN, the effects of both of these genes on their downstream pathways occur at the level of protein phosphorylation and would not necessarily be expected to be reflected in changes in the mRNA levels of these downstream effectors.

In summary, the tumor sample displayed both an activating B-Raf V600E mutation, and down-regulation of tumor suppressor PTEN. Both of these pathways lead to cell proliferation, but targeting each individually has mixed results in cancer patients. There is literature evidence that targeting both of these pathways simultaneously may be effective in treating melanoma. Furthermore, there are approved drugs available which target both B-Raf (sorafenib), and mTOR (e.g., rapamycin) which is a downstream effector of PTEN loss.

In the foregoing examples, a mutation in the NRAS gene which could have activated the PI3K pathway and thus suggested combination treatment. However, this mutation was not characterized as to whether it would result in a loss or gain of function or neither. Since the mutation was not characterized, expression data were necessary to result in the suggestion of combination treatment.

These conclusions are validated by studies elucidating B-Raf pathway dysregulation at the protein level by determining whether downstream effectors of B-Raf are hyperactivated using immunohistochemistry of tumor sections and control tissue using phospho-specific antibodies to ERK1/2 and MEK, downstream effectors of B-Raf with respect to cell growth and proliferation, wherein hyperphosphorylation of ERK1/2 and MEK indicate over-activation by B-Raf and supports the validation of B-Raf as a target. PTEN at the protein level is also elucidated by determining whether downstream proteins normally inhibited by PTEN are hyper-activated. This can be done using immunohistochemistry of tumor sections and control tissue using phospho-specific antibodies to AKT and P6SK, pro-proliferative kinases in mTOR pathway normally inhibited by PTEN, wherein hyperphosphorylation of AKT and P6SK indicate over-activation of mTOR as a result of PTEN loss and supports the validation of mTOR as a target.

These are the complete networks of interacting genes generated from the filtered list of up- and down-regulated genes. The Score column represents the overall level of interconnectedness within each network, and the Top Functions column describes cellular functions that are over-represented (relative to chance) in each network, as determined by the individual annotation of each gene in the network.

TABLE 6

Regulated Networks from Tumor Sample

| ID | Molecules in Network | Score | Focus Molecules | Top Functions |
|---|---|---|---|---|
| 1 | C6ORF48, CACYBP, CAD, CFTR, COG2, COG3, COG8, DHX29, DLG5, FAT1, GCC1, HNRNPU, HSPA6, IL1RAPL1, KDELR2, MLF1, MUC2, NDN, PDZK1, PHGDH, PHLDA2, RCN1, SDF2L1, SEC61A1, SEC61G, SH3BGRL2, SLC1A5, SRP68, SRPR, SYNGAP1, TBC1D17, TNFRSF1B, TXNDC11, XBP1, XPO1 | 31 | 35 | Cellular Assembly and Organization, Amino Acid Metabolism, Post-Translational Modification |

TABLE 6-continued

Regulated Networks from Tumor Sample

| ID | Molecules in Network | Score | Focus Molecules | Top Functions |
|---|---|---|---|---|
| 2 | ABTB2, BTN3A3, C11ORF82, CHST4, CTNNA-CTNNB1-CTNNG-CDH5, CTSF, DHRS3, ENDOG, FOXF2, KIF20A, LAMP3, LSS, MCOLN1, MCOLN3, NFRKB, NINJ1, PDZD2, PEMT, PLD3, PRKRIR, PXMP3, RASA3, SCUBE2, SERPINB8, SLC14A2, SLC16A5, SLC1A4, SLC28A2, TDRD7, TMEM49, TNF, TNFRSF21, UACA, ZNF330, ZNF365 | 30 | 34 | Cellular Movement, Hematological System Development and Function, Immune Cell Trafficking |
| 3 | AKR1B10, ANKRD35, ATXN10, C19ORF70, CDR2, CIRBP, COL24A1, EHD4, FAM113A, FOLR2, GSTK1, HIVEP3, HRK, JUN, LXN, MAFF, MAGEA6, MTHFR, OSTC, PHACTR3, PSPH, RPN2, SEC63, SERP1, SLC25A22, SNRPA1, SRPRB, SSR4, STYXL1, SVIL, TCF20, Tcf1/3/4, TNFRSF14, TSC22D1, VEPH1 | 30 | 34 | Protein Synthesis, Protein Trafficking, Genetic Disorder |
| 4 | ACTN4, ANKS1A, ASPM, CHCHD10, COL6A2, CRIP1, DZIP3, EMP3, ERBB2, ESPL1, IRX3, KRT7, LTBP3, MFNG, MICALL2, NPNT, NPTX2, NUCB2, P4HA1, P4HA2, P4HB, PDLIM4, PINK1, PMEPA1, PQLC1, Procollagen-proline dioxygenase, RAB18, SEMA7A, SH3BGRL, SHROOM3, SPAG4, SRPX, ST3GAL4, TAX1BP3, WFS1 | 30 | 34 | Amino Acid Metabolism, Post-Translational Modification, Small Molecule Biochemistry |
| 5 | AASS, BMI1, CBX2, CBX7, CELSR2, COLEC12, Dolichyl-diphosphooligosaccharide-protein glycotransferase, EXOC1, FAM45A, HIST1H4C, HIST2H2AA3, HIST2H2BE, IGF2BP2, KIAA1267, KIAA1797, KLF6, MYCBPAP (includes EG: 84073), NECAB2, PCGF6, PHF10, PHF19, PRRG2, PRUNE, PXN, RRBP1, SERPINH1, STT3A, TBL1XR1, TES, TNS1, TRIM9, TUSC3, U2AF1, VCL, VSX2 | 30 | 34 | Cancer, Skeletal and Muscular Disorders, Embryonic Development |
| 6 | ABL1, Adaptor protein 1, ANKRA2, AP1M1, APC, BST2, C20ORF46, CADM1, CBX3, CBX5, CHPF, CRTAM, DDB1, DIAPH1, DOK3, EPB41L3, FAM126A, GGA2, HDAC4, HPRT1, KIF15, LRP3, MKI67, NECAP2, NR2C1, NXPH3, PIGR, PIN1, PRTFDC1, PVRL3, SAE1, SH3BP2, TNFRSF11B, WDR40A, ZIC2 | 30 | 34 | Gene Expression, Cancer, Gastrointestinal Disease |
| 7 | ACTR10, ACTR1A, ANKS1B, CELSR3, DCTN2, DCTN3, DST, DYNC1H1, DYNC1I1, Dynein, DYNLRB1, DYNLRB2, DYNLT3, FAM96B, INA, KHDRBS3, KNTC1, LDB3, MYBPH, MZF1, NEFL, NIN, P38 MAPK, PDXDC1, PHLDA3, PNO1, RGMA, SAAL1, SFRS9, SGSM2, SPTBN2, TESC, TNNC2, TRA2A, ZW10 | 28 | 33 | Cellular Function and Maintenance, Cellular Assembly and Organization, Nervous System Development and Function |
| 8 | AP3B1, AP3M1, ARNTL, BHLHB, BHLHE40, BHLHE41, BUB1, CBLC, ETV5, KCNK3, LHX6, LMCD1, Mapk, MARCH2, NEUROG3, NKX2-1, OLIG2, PTCRA, PTPRH, PTRF, SFTPC, SGOL1, SPRY4, STRA13, STX7, STX8, THBS2, TPD52L1, TRHR, VAMP8, VPS16, WDR91, WWTR1, XPOT, ZNF148 | 28 | 33 | Cellular Assembly and Organization, Cellular Growth and Proliferation, Nervous System Development and Function |
| 9 | BLOC1S1, BRWD1, CDCA7L, CORO2A, CPS1, DEAF1, DUSP22, ELMOD2, FASTKD5, HOXB1, ING3, KIAA1279, MAL, MED4, MED25, MED30, NR3C1, PARP4, PLEKHF1, PSMG2, RABGGTB, RRAGC, SEMA5B, SLC38A1, TADA1L, TADA2L, Taf, TAF5L, TAF6L, TELO2, TNFAIP1, TPST2, TRAP/Media, TRRAP, WDR40B | 28 | 33 | Gene Expression, Cell Signaling, Amino Acid Metabolism |
| 10 | ABHD6, Adenosylhomocysteinase, AHCY, AHCYL1, AHCYL2, APEH, APOBEC3B, CMBL, CTAGE5, DCPS, DCXR, EXOSC4, FAHD1, Hydrolase, IER3IP1, IMPA2, KCTD12, LRRC8D, MLEC, MRTO4, NHP2L1, NLN, PFAS, PPM1G, PTPN7, REXO2, RHPN2, STRADB, TARSL2, TMEM51, TMPRSS3, TRAF6, TSEN15, TUBB6, ZRANB1 | 28 | 33 | Carbohydrate Metabolism, Small Molecule Biochemistry, RNA Damage and Repair |
| 11 | C17ORF70, CCL5, ECEL1, EI24, FANCD2, FANCL, FAR1, FOXC1, HOXA5, HOXB3, HOXD12, IER2, KLF10, MEIS1, MEN1, MLKL, NELF, NKX2-5, PBX1, PBX2, PHC1, PTGDS, RAD51AP1, RNA polymerase II, SETD2, SFMBT1, SLC9A8, SMARCD3, SMYD3, TARBP1, TBX1, TBX2, TSPAN7, ZDHHC7, ZNF83 | 28 | 34 | Endocrine System Development and Function, Organ Development, Organismal Development |
| 12 | ACAA2, AGPAT9, ANXA5, Apyrase, ASB13, EIF3A, EIF4EBP1, EIF4G1, ENTPD3, ENTPD6, ENTPD7, F5, FGFR3, FGFR4, GPRIN2, GRAMD3, HOXC9, KIAA0247, LAMP2, LDLRAD3, LIF, LOXL4, Nucleoside-diphosphatase, NUDT9, OSBP2, PROS1, SELENBP1, SERTAD2, SMG7, STAMBPL1, TMCC2, TRIP13, UPF2, VWF, ZFP36 | 27 | 33 | RNA Damage and Repair, Organ Development, Respiratory System Development and Function |
| 13 | AFF3, BAT2, C4ORF14, COL9A1, COL9A2, DDX20, DDX47, DICER1, EIF2C2, H1F0, HSP90AB1, HSPH1, HYOU1, Importin beta, IPO8, IRS1, L-lactate dehydrogenase, Ldh, LDHA, LDHAL6A, LDHAL6B, LDHC, LSM10, NFIB, NPAS2, PES1, PIWIL4, RAD51L1, SCML2, SND1, SNRPD1, SNRPF, SNRPG, STARD13, TNRC6B | 26 | 32 | RNA Post-Transcriptional Modification, Cancer, Respiratory Disease |

TABLE 6-continued

Regulated Networks from Tumor Sample

| ID | Molecules in Network | Score | Focus Molecules | Top Functions |
|---|---|---|---|---|
| 14 | BAAT, COL15A1, Delta/Jagged, DLL1, DLL3, EHD1, FBLN1, GIPC1, GRB10, HES1, HES6, HYAL2, ID2, IGF1R, KCNA3, KCNAB2, KLF2, LAMA4, MEGF10, MFAP5, MIB2, NOC2L, Notch, NOTCH2, NOTCH4, NOV, OLIG1, RPL24, SDC4, SH3BP4, SLC7A8, SLCO2A1, TFPI, Troponint, TYMS | 26 | 32 | Cellular Development, Cardiovascular System Development and Function, Tissue Morphology |
| 15 | ADAM19, Alpha catenin, ASAP1, BXDC2, C20ORF30, CAM, CLDN7, CLDN12, CNTNAP2, CTNNA1, DDX27, DHX57, DKC1, GNL3, KIF14, LYAR, MARCKSL1, MPDZ, NEDD9, OSTF1, PACSIN3, Pseudouridylate synthase, PSTPIP1, PTK2B, PTPN3, PUS1, PUS3, RPL28, RPUSD4, SH3KBP1, SRP14, TJP2, TJP3, TRUB1, VEZT | 26 | 32 | Cell-To-Cell Signaling and Interaction, Cellular Assembly and Organization, Cancer |
| 16 | AATF, CAMP, CCL2, CHGB, CSPG4, DAPK3, DNA-directed DNA polymerase, EYA1, EYA4, GTF2F2, HMGB2, KIAA0101, MPHOSPH6, MPZ, PAFAH1B3, PAWR, PKM2, PLEKHM1, PMP22, POLB, POLD1, POLL, POLQ, POU3F1, REV3L, SIX1, SIX4, SIX5, TFIIF, TFIIH, TLE1, TLE3, TNFAIP2, UTX, XRCC1 | 26 | 32 | DNA Replication, Recombination, and Repair, Cellular Assembly and Organization, Nervous System Development and Function |
| 17 | Alcohol group acceptor phosphotransferase, ARID2, ARID1A, ARID4B, BRAF, CDK8, EFCAB6, EVI1, GRK4, GSPT1, HDAC1, LIMK1, MAD1L1, MAP2K3, Map3k, MAP3K6, MAP3K8, MAPK9, MECP2, MEKKs, NDC80, NEK2, PAK1, PAK2, PCTK3, PRKCQ, PRKX, RCOR2, SALL1, SALL4, SAP18, SMARCE1, SPC25, TBX3, TTK | 26 | 32 | Cell Cycle, Amino Acid Metabolism, Post-Translational Modification |
| 18 | AGL, ALP, ANK3, BMP, BMP4, BMP7, BMPR2, C10ORF54, COL7A1, CXORF15, DYNC2LI1, EID2, FST, ID1, ID3, JPH1, KLHL9, KRT2, LAPTM5, NEDD4L, NELL1, PAX9, PDZRN3, PYCR2, RASD2, RSPH3, RUNX2, Smad, SMAD3, ST6GALNAC2, TAGLN, TWSG1, ZC3H7A, ZEB2, ZMIZ1 | 26 | 32 | Cell Signaling, Cell Morphology, Cellular Development |
| 19 | ADAMTS2, ADAMTS4, ADAMTS7, APH1B, ATG4C, BIRC6, BLMH, BMP1, CASP4, CASP6, COL4A1, COMP, CSF1R, CSF2RB, CTSD, Cytochrome c, DIDO1, FAP, GRN, GZMB, ICAM5, JUP, LTA4H, MDN1 (includes EG: 23195), MT1A, PCSK7, peptidase, PSEN2, PSMB5, RNF150, UBE2, UBE2E2, UBE2F, UBE2L6, UBE2S | 26 | 32 | Protein Degradation, Connective Tissue Disorders, Dermatological Diseases and Conditions |
| 20 | CITED2, CMPK1, CNPY2, DSTYK, DUB, FIBP, GZMM, ITIH5, KIF23, LHX2, MIF, MSRB2, MYCN, NMU, NMUR2, OTUB1, PARP1, PDE4DIP, PLA2, PLA2G2A, PLA2G4D, RASGRF1, TGM2, TMEM87B, TNIK, UCHL1, UCHL3, Uridine kinase, USP6, USP8, USP10, USP48, USP53, USP54, ZFAND5 | 26 | 32 | Behavior, Digestive System Development and Function, Cell Morphology |
| 21 | ANK1, BRPF1, CA2, CA3, CA7, CA14, CA5B, Carbonic anhydrase, CKS2, COPS6, CRELD1, CSRP1, CSTF3, CTDSPL, DLGAP5, DRAP1, FBP1, Fructose 2,6 Bisphosphatase, GGT1, HEXB, MAP7D1, MXD4, PFKFB2, PFKL, PFKM, PGM1, PLOD1, PTEN, PTPRZ1, PYGL, SLC4A2, SLC4A3, STK40, SURF4, TCP10L | 26 | 33 | Genetic Disorder, Renal and Urological Disease, Infectious Disease |
| 22 | ADAMTS5, AIF1, ALT, ANXA9, CARD8, CASP1, CASP5, Casp1-Casp5, CEBPG, CHST6, CP, F13A1, GM2A, GPT2, IFT57, IL1B, IL1F7, ITPA, LCP1, MIA, NALP, NLRP1, NLRP2, NLRP6, PELI1, PLA2G7, PLB1, PPHLN1, RARRES2, RNASE7, SLC25A25, SMPD1, SRGN, TPSD1, TYMP | 26 | 32 | Lipid Metabolism, Small Molecule Biochemistry, Genetic Disorder |
| 23 | 3',5'-cyclic-nucleotide phosphodiesterase, ARL2, BASP1, Calmodulin, CAMK1, CAMKK2, CCT2, CCT5, CDYL, DHX38, FAM10A4, IQCB1, LIMA1, LNX2, MAP3K3, MYO1B, MYO1D, NRGN, NUMBL, Pde, PDE1B, PDE2A, PDE5A, PDE6B, PDE6D, PDE7B, PDE8B, PPP4C, RAI14, RIPK3, RPH3AL, SCIN, TRPM2, TRPV4, UNC13B | 26 | 32 | DNA Replication, Recombination, and Repair, Nucleic Acid Metabolism, Small Molecule Biochemistry |
| 24 | APPL2, BAT5, C19ORF10, DTX3L, GPRC5C, IFI27, IFIT2, IFIT3, IFITM1, Immunoproteasome Pa28/20s, KPNA5, LY6E, NCAPD3, NCAPH2, ODF2L, PARP9, PDLIM2, PILRB (includes EG: 29990), PRSS23, PSMA2, PSMA6, PSMB, PSMB7, PSMB8, PSME2, RNF5 (includes EG: 6048), SCP2, Soat, SOAT1, SOAT2, SP110, STAT1, STAT2, TMEM147, TMEM222 | 25 | 32 | Gene Expression, Lipid Metabolism, Small Molecule Biochemistry |
| 25 | ABL2, ALOX5AP, Ant, Basc, BCL2L1, BCL2L10, BLM, BNIPL, BRIP1, CEBPZ, CHEK1, CHTF18, DSCC1, ERCC1, Mre11, PAXIP1, RAD50, RAD9A, RFC2, RFC3, RPA, RPA3, RTKN, SEMA6A, SIVA1, SORBS2, SRPK2, TERF2, TERF2IP, TIMELESS, TIMP4, TP53BP1, WISP1, XRCC5, XRCC6 | 25 | 31 | Cellular Function and Maintenance, DNA Replication, Recombination, and Repair, Cell Cycle |
| 26 | ADARB1, ADD3, AXIN2, CCNO, CTH, CXCR7, DTNA, ELOVL2, GDF15, GHR, GREM1, growth factor receptor, HSD3B7, KCNJ12, MCFD2, MT1E, MTHFD2, NOX4, PDGFBB, PDGF-AA, PLEKHA1, PRRX2, PSAT1, RND3, SLC1A1, SNTA1, SNTB1, SNTB2, SNURF, Sphk, SYNC, SYNE1, TRIB3, UCK1, VAPB | 25 | 31 | Amino Acid Metabolism, Small Molecule Biochemistry, Cell Death |

TABLE 6-continued

Regulated Networks from Tumor Sample

| ID | Molecules in Network | Score | Focus Molecules | Top Functions |
|---|---|---|---|---|
| 27 | ASB9, C4ORF17, CDC14B, CKB, CKM, Creatine Kinase, ENO1, ENO2, Enolase, GTF2IRD1, HERC5, KRT78, MAP1B, MEF2C, MYOM2, NEBL, NGF, RANBP1, ROR1, RUSC1, SCG2, SERPINF, SERPINF1, SERPINF2, SH3PXD2A, SIGIRR, SIRT2, SNX22, STK38, SYNPO2, TRAF3IP1, TUBA4A, Tubulin, VGLL4, ZYX | 25 | 31 | Small Molecule Biochemistry, Cell-To-Cell Signaling and Interaction, Cellular Assembly and Organization |
| 28 | AKAP6, ALS2CR12, BCLAF1, Cdc2, CLK1, Cyclin B, DARS, DNA-directed RNA polymerase, FKBP5, FKBP6, FKBP11, FLNB, GALK1, HMG20B, KIF4A, LATS2, LPHN1, LPHN2, Peptidylprolyl isomerase, PIK3R1, PIN4, POLR1B, POLR1E, POLR2D, POLR2F, POLR3A, PPIG, PPIL3, QRICH1, ROS1, SFRS4, SHANK2, TACC2, TAF1C, TCOF1 | 25 | 31 | Gene Expression, Cell Cycle, Cell Morphology |
| 29 | BCL10, BIRC3, BIRC8, BRCA1, C11ORF9, C9ORF89, CARD10, Caspase, CCNG1, CD80/CD86, CHST1, CTCFL, DLAT, E3 RING, HERPUD1, HIST1H2BC, KHDC1, LSP1, MLXIP, MX1, NT5DC2, NUFIP1, P2RX1, PDCD6, PKC(β, θ), PLAG1, PLSCR4, STC1, SUGT1, TNFRSF18, TNFRSF19, TRAF1, WEE1, WIT1, ZNF350 | 25 | 31 | Cell Death, Cancer, Cell Cycle |
| 30 | CD34, CRYAB, CTSL2, CUBN, DUSP6, Dynamin, ENC1, FSH, FSHR, GATA2, GPRC5B, HAS2, hCG, HPSE, HSD17B, HSD17B1, HSD17B4, HSPB2, LHCGR, LRRC32, MAMLD1, MARCH3, MT1H, MT1X, MYO1E, PLA1A, RGS5, SETX, SLC20A1, STEAP1, STK17A, TF, TFRC, TSHB, VGF | 25 | 31 | Organ Development, Reproductive System Development and Function, Developmental Disorder |
| 31 | ADRB2, BSCL2, C9ORF46, CHD3, Ck2, Clathrin, COL1A1, COL1A2, CSPG5, CUX1, DNASE2, DRD5, DSPP, FAM134A, FAM176A, FAM86C, Gs-coupled receptor, Hat, IRF4, NEIL2, ODC1, PAM, PLA2R1, PRDX5, RBM17, SAT1, STARD10, TGFB3, TNP1, TOP2A, TSC22D3, TSPAN13, UBQLN3, YBX1, YBX2 | 25 | 31 | Cancer, Tumor Morphology, Molecular Transport |
| 32 | APP, ATOX1, ATP7A, C9ORF75, CLIC1, CLSTN1, ETHE1, EVI5L, FAM160A2, GLUL, HSD17B14, KCTD13, Na-k-atpase, NUDT18, PCBD1, PDIA6, PERP, Plasminogen Activator, PPME1, PPP1R13B, RAB38, RAB33A, RABAC1, RENBP, RTN2, RTN3, SDPR, SNX15, SORL1, SPON1, SRGAP3, TM2D1, TP53BP2, TP53I3, ZBED1 | 24 | 33 | Cellular Function and Maintenance, Small Molecule Biochemistry, Molecular Transport |
| 33 | ALAD, ARID1B, BBS1, BBS7, CCL8, CCL23, CCR1, EDEM1, FLOT1, GNA14, HES5, HSCB, IFI30, IFI35, IFITM2, IL23, IL24, IL11RA, IL20RA, MAN2A1, MAN2A2, Mannosidase Alpha, NIPSNAP3A, NMI, PCM1, PCNT, PLP2, RNASE1, RRP12, SOX10, STAT3, STAT1/3/5/6, THY1, TRIP10, WASP | 24 | 31 | Cellular Assembly and Organization, Developmental Disorder, Genetic Disorder |
| 34 | ANTXR1, ATF5, BATF, BATF3, BCL11A, BRD7, CEBPB, CREB5, CREB3L4, Ctbp, DBP, DDIT3, DFF, ELL3, F8, F8A1, FOSB, FTH1, HIPK2, LCN2, MAGEH1, NFIL3, NR4A2, ORM1, PER3, Pias, PIAS3, PML, SATB2, SLK, TDG, TM4SF1, Top2, TP53INP1, UPP1 | 24 | 31 | Gene Expression, Cancer, Hematological Disease |
| 35 | ACP1, AK3L1, ARSB, ARSG, ARSH, ARSJ, ARSK, Aryl Sulfatase, BCAT2, CST2, ENSA, GART, HEY2, HIF3A, JAG1, KCTD15, NCK, Pak, Pdgf Ab, PDGF-CC, PDGFC, PDGFD, PDGFRB, PPA1, PPP1R15B, SEMA3B, SMTN, ST5, STARD8, SULF1, SULF2, SYNM, TBC1D8, VEGFA, WIPI1 | 23 | 30 | Cellular Movement, Skeletal and Muscular System Development and Function, Gastrointestinal Disease |
| 36 | Acid Phosphatase, ACP5, ACP6, AHCTF1, CENPF, CPNE2, CPNE4, DHCR7, IBSP, KNDC1, LIMS1, LIMS2, Mi2, MYCBP2, MYO1C, NUP133, NUP160, NUP214, NUPL1, PARVG, PKC (α, β, γ, δ, ε, ι), POU3F2, POU3F4, PQBP1, RAD21, Ras, RASAL1, RDX, RGS10, RSU1, SEC13, SGPP1, SMOC2, Tap, TM7SF4 | 23 | 30 | Molecular Transport, RNA Trafficking, Cellular Growth and Proliferation |
| 37 | ABCC6, ABCD3, ACTC1, adenylate kinase, AFG3L2, AK1, AK5, ATP11B, ATP13A5, ATP1B1, ATP5D, ATP5G1, ATP6V0A2, ATP6V1E2, ATP6V1G2, ATP6V1H, ATPase, BAX, COX7A1, CTSK, Cytochrome c oxidase, ETNK2, H+-exporting ATPase, H+-transporting two-sector ATPase, HTR2B, MFN1, MYH1, MYH6, MYL1, MYO9B, NOMO1, PSMD6, SMARCA4, TNNI2, TRIM63 | 23 | 30 | Energy Production, Nucleic Acid Metabolism, Small Molecule Biochemistry |
| 38 | ACACB, AMPK, ANGPT2, ANP32B, APOB, CCNG2, CDH1, CSNK2A2, FKBP4, GTSE1, Hsp27, HSP90AA1, HSPA2, HSPA5, HSPA1A, HSPA1B, KCNMA1, KLK3, KLK6, LOXHD1, NAP1L4, Ndpk, NME1, NME2P1, Nos, PA2G4, PRKAA, RBM4B, RPL30, RRM2, TMEM132A, TTL4, TXNDC3, ZBTB33, ZEB1 | 23 | 30 | Cellular Function and Maintenance, Cellular Compromise, Cell-To-Cell Signaling and Interaction |

TABLE 6-continued

Regulated Networks from Tumor Sample

| ID | Molecules in Network | Score | Focus Molecules | Top Functions |
|---|---|---|---|---|
| 39 | 3 BETA HSD, ALOX5, ASCC2, ASS1, CHUK, CLEC11A, DHH, EGR2, EGR3, FAM118B, GJB1, GLI1, Gli-Kif7-Stk36-Sufu, GMFG, HHIP, IDS, KIF7, LASS4, Mek, NAB1, NCL, NDRG1, NXPH4, Patched, PPP2R2B, PPT2, S100A9, SELE, SH3D19, SHMT2, SNX10, STK36, Tnf receptor, TNFSF13B, TUBB4 | 23 | 30 | Cell Signaling, Cell-mediated Immune Response, Cellular Development |
| 40 | ALS2CR11, BRD8, CCDC5, CCDC76, CDC45L, CDCA4, CDT1, CREG1, CSDE1, DUOX2, E2f, E2F2, EP400, ERRFI1, HIST1H3H, L3MBTL, MCM3, MCM4, MCM5, MCM6, MCM7, MCM10, MCPH1, MTSS1, NASP, NOM1, NRD1, NUSAP1, OIP5, Pdgf, PNKP, Rb-E2F transcription repression, SETD8, TCEB3B, ZBTB43 | 23 | 32 | Cell Cycle, DNA Replication, Recombination, and Repair, Gene Expression |
| 41 | ADH4, AIFM1, BSN, C6, C8, CAPN1, CAPN6, CAPN9, CAST, CDK5R1, CDK5R2, CTSC, CYB5R1, CYB5R2, DHRS1, DHRSX, Electron-transferring-flavoprotein dehydrogenase, ETFDH, IRF2, LPA, MAPRE2, MLPH, Oxidoreductase, P2RY2, PDIA5, RDH, RDH5, RDH8, RDH11, RETSAT, RIMS1, SLC35C2, SLC9A3R1, TBC1D10A, VCAM1 | 22 | 31 | Lipid Metabolism, Small Molecule Biochemistry, Vitamin and Mineral Metabolism |
| 42 | AHSG, AKT1, ARL15, BPGM, BRSK1, C1QC, CCDC106, CDCA3, CRMP, CRMP1, DDX18, Dihydropyrimidinase, DPYS, DPYSL3, DPYSL5, FES, FXYD5, HNRNPH3, KIAA1199, LRRC1, MICAL1, MYT1, NUAK1, PKC ALPHA/BETA, Plexin A, PLXNA1, PLXNA2, PLXNA3, PRPSAP1, Sema3, SEMA3C, SEMA3F, SIK1, STRADA, UBE4B | 22 | 30 | Nucleic Acid Metabolism, Cell Morphology, Renal and Urological System Development and Function |
| 43 | CABLES1, CDK2, CKS1B, Glutathione peroxidase, Glutathione transferase, GMFB, GPX8, GSTA2, GSTM1, GSTM2, GSTM4, GSTO1, GSTO2, GSTP1, GSTT1, IGSF21, Laminb, LMNA, LMNB1, MGST2, MGST3, MRFAP1L1, MYH8, NPDC1, PDCD11, PKC (α, β, ε, γ), PKC (α, ε, θ), PRKCA, PRKCH, RAB17, S100A8, Sod, TAGLN2, TSNAX, UNC84A | 21 | 29 | Cell Morphology, Genetic Disorder, Hepatic System Disease |
| 44 | ALDH2, ANAPC13, APC, AURKA, BCKDHA, BCKDHB, CD3EAP, CDC20, Creb, CSN3, ETV1, FBXO5, GALNT3, GALNT8, GALNT11, GALNT12, GALNTL4, GRIN, GRIN2C, GRIN2D, HSPE1, KRT1, MAPK11, MSK1/2, MUC5AC, NOX5, PKMYT1, Polypeptide N-acetylgalactosaminyltransferase, PRKD1, PTTG1, RPS6KA2, RPS6KA4, Rsk, STEAP3, UBE2C | 21 | 29 | Cell Cycle, Embryonic Development, Cell-mediated Immune Response |
| 45 | Ahr-aryl hydrocarbon-Arnt, ANXA4, ARMET, CYP1A1, CYP2J2, CYP4A22, CYP4F11, CYP4F12, ELF4, EPHX1, GPC1, MYO10, NADH dehydrogenase, NADH2 dehydrogenase, NADH2 dehydrogenase (ubiquinone), NDUFA4L2, NDUFB6, NDUFB7, NDUFB8, NDUFC2, NDUFS3, NDUFS4, NDUFS5, NDUFS7, NDUFS8, NDUF V1, NDUFV2, NDUFV3, NOS3, NOSTRIN, Nuclear factor 1, TACC3, TRIP11, TUBA1A, Unspecific monooxygenase | 21 | 29 | Cardiovascular Disease, Genetic Disorder, Neurological Disease |
| 46 | ADPGK, AKAP12, ALPHA AMYLASE, AMY1B, AMY2B, CCNE1, CD38, CDKN1C, CTSH, Cyclin A, Cyclin D, Cyclin E, DMXL1, E2F5, EPAS1, FRAP1, GAL3ST1, GBE1, IL6R, LGALS3, LYZL1, MB, MEF2, NRAS, NRN1, NUDT10, OMA1, Pld, PLEK2, PRR5, RASSF1, RIN2, SKP2, SLC16A3, ZBTB17 | 21 | 29 | Cell Cycle, Cancer, Reproductive System Disease |
| 47 | 14-3-3, ADARB2, CRABP2, CXCL10, CXCR4, DHDDS, EMID1, GAD1, GPR1, IL17R, IL17RA, INTS3, LCT, LRRC37A3, MAP2K1/2, MARK1, MYH2, NRIP1, PAX3, PRAME (includes EG: 23532), PRDM5, PSG2, PTPRJ, RARA, RARB, Rbp, RBP5, RBP7, SLC26A4, STAT5a/b, SYNCRIP, TG, TGM1, TNFRSF10B, Transferase | 21 | 29 | Embryonic Development, Tissue Morphology, Dermatological Diseases and Conditions |
| 48 | ABR, ARHGAP27, ARHGDIB, Arp2/3, BAIAP2, CNTN1, CNTNAP1, DEF6, DOCK2, EFNB3, EPB41L2, EPS8, EVI5, FCGR1A/2A/3A, Integrin alpha V beta 3, ITGB5, PARD6G, Phosphatidylinositol4,5 kinase, PIP4K2A, PIP5K1A, Plexin B, PLXNB1, PREX1, PTPRB, Rac, RAC1, RAC2, RAPGEF1, RASSF2, RGL2, RIT1, RRAS, SEMA4D, TIAM2 (includes EG: 26230), TNK2 | 21 | 29 | Cellular Assembly and Organization, Nervous System Development and Function, Cell Morphology |
| 49 | BGN, BMS1, C2, C1q, C1QA, C1S, CCNB2, Collagen(s), Complement component 1, DCN, FBN1, FMOD, FSTL1, Igm, KIAA1191, LAMA3, LSM4, NCR3, NOL12, PLEKHA5, PTS, RCBTB1, RORC, SF3B3, SFRS15, SFTPD, SLC25A38, SNRNP70, SNRPB2, SNRPN, Tgf beta, TGFBI, TLL1, TLL2, WBP4 | 20 | 30 | Cell-To-Cell Signaling and Interaction, Connective Tissue Development and Function, Skeletal and Muscular System Development and Function |

TABLE 6-continued

Regulated Networks from Tumor Sample

| ID | Molecules in Network | Score | Focus Molecules | Top Functions |
|---|---|---|---|---|
| 50 | B4GALT1, B4GALT4, B4GALT5, B4GALT6, CD9, CD81, CDC42EP5, CSF3R, DUSP10, DUSP16, Erm, ETV4, Galactosyltransferase beta 1,4, Gm-Csf Receptor, GPR56, Integrin alpha 3 beta 1, Jnk, KLHL2, LGALS8, MSN, MT1G, MTF1, NET1, phosphatase, PI4KA, PRDX4, PTGFRN, RNASEL, ROR2, SACM1L, TMC6, TMC8, TNN, TSPAN, TSPAN4 | 20 | 28 | Dermatological Diseases and Conditions, Genetic Disorder, Carbohydrate Metabolism |

REFERENCES

Dankort D, Curley D P, Cartlidge R A Nelson B, Karnezis A N, Damsky W E Jr, You M J, DePinho R A, McMahon M, Rosenberg M. 2009. Braf V600E cooperates with Pten loss to induce metastatic melanoma. *Nat Genet.* 41(5):544-52.

Goel V K, Lazar A J F, Warneke C L, Redston M S, Haluska F G. 2006. Examination of Mutations in BRAF, NRAS, and PTEN in primary cutaneous melanoma. *J Invest Dermatol.* 126:154-160.

Schreck R, Rapp U R. 2006. Raf kinases: Oncogenesis and drug discovery. *Int J Cancer.* 119: 2261-2271.

The invention claimed is:

1. A method to identify at least one therapeutic target in an individual cancer patient, which method consists essentially of:
   (a) assaying multiple characteristics of the genome and/or multiple characteristics of the molecular phenotype in a biopsy of the cancer afflicting said patient to obtain one or more first data sets wherein each data set consists of a single type of characteristic and assaying said characteristics in normal tissue from said individual patient to obtain one or more second data sets, wherein said multiple characteristics represent a sufficient fraction of the networks of interacting genes and their corresponding proteins in any said patient to permit identification of at least one dysregulated pathway;
   (b) identifying characteristics from (a) in said one or more first data sets which differ from those in said one or more second data sets to obtain differentiated characteristics; and
   (c) matching said differentiated characteristics of (b) to pathways to identify one or more pathways dysregulated in said cancer biopsy as compared to normal tissue for therapeutic intervention wherein
      (i) each pathway comprises a multiplicity of interacting proteins curated from the literature;
      (ii) the differentiated characteristics are used to identify dysregulated pathways by applying statistical approaches based on triangulation to each pathway as a whole; and
      (iii) whereby one or more pathways is determined to be dysregulated in said individual patient's cancer as compared to the patient's normal tissue; and
   (d) identifying at least one therapeutic target wherein interaction with said target would overcome dysregulation of said pathway;
   wherein step (b) and/or the step (c) is performed by a computer; and
   wherein each said identified dysregulated pathway contains a sufficient number of independent data points to overcome statistical limitations of one or two samples and exhibits a coherent pattern whereby gene products are dysregulated in accordance with the pathway itself; and
   said target is responsive to approved or investigational drugs or biologics.

2. The method of claim 1, wherein said pathways in step (c) (i) are curated by accessing at least one database describing pathways exhibited by gene products.

3. The method of claim 1, wherein said pathways are metabolic pathways and/or signal transduction pathways.

4. The method of claim 1, wherein characteristics of the genome are selected from the group consisting of single nucleotide polymorphisms (SNPs), copy number variants (CNVs), loss of heterozygosity (LOH), gene methylation, and sequence information.

5. The method of claim 1, wherein characteristics of the molecular phenotype are selected from the group consisting of overexpression or underexpression of genes, proteomic data, and protein activity data.

6. The method of claim 1, wherein said triangulating is used to assess validity of the ascertained pathways as compared to noise.

7. The method of claim 1, wherein said triangulating applies one or more of algorithms 1a, 2a, 3a, 1b, 2b and 3b.

8. The method of claim 1, wherein at least two datasets which are different with respect to the type of characteristics are obtained from each of said cancer biopsy and normal tissue of said individual patient and said method further includes integrating the identified differentiated characteristics from said at least two datasets to identify patterns that are ascertainable only from concurrent matching of said different characteristics to said pathways.

9. The method of claim 1, which further includes extrapolating the identified differentiated characteristics to characteristics that have not been measured.

10. The method of claim 1, which further includes designing a treatment protocol using drugs and/or biologics that interact with said at least one target.

11. The method of claim 10, which further includes formulating said designed treatment protocol into pharmaceutical compositions.

12. The method of claim 10, which further includes treating said patient with the designed treatment protocol.

13. The method of claim 10, which further includes applying the identified differentiated characteristics and treatment protocol design to diagnostic and therapeutic discovery protocols.

* * * * *